(12) United States Patent
Deaton et al.

(10) Patent No.: US 12,005,087 B2
(45) Date of Patent: Jun. 11, 2024

(54) **PROBIOTIC (*BACILLUS SUBTILIS*) SUPPLEMENTATION FOR IMPROVEMENT OF BODY COMPOSITION IN FEMALE ATHLETES**

(71) Applicant: Deerland Enzymes, Inc., Kennesaw, GA (US)

(72) Inventors: John Deaton, Kennesaw, GA (US); Ana Maria Cuentas, Woodstock, GA (US)

(73) Assignee: Deerland Enzymes, Inc., Kennesaw, GA (US)

( * ) Notice: Subject to any disclaimer, the term of this patent is extended or adjusted under 35 U.S.C. 154(b) by 0 days.

(21) Appl. No.: 17/354,208

(22) Filed: Jun. 22, 2021

(65) Prior Publication Data

US 2021/0315945 A1 Oct. 14, 2021

Related U.S. Application Data

(63) Continuation-in-part of application No. 16/141,591, filed on Sep. 25, 2018, now abandoned.

(60) Provisional application No. 62/562,887, filed on Sep. 25, 2017.

(51) Int. Cl.
*A61K 35/742* (2015.01)
*A61K 9/00* (2006.01)
*A61K 35/00* (2006.01)
*A61P 3/04* (2006.01)

(52) U.S. Cl.
CPC .......... *A61K 35/742* (2013.01); *A61K 9/0053* (2013.01); *A61P 3/04* (2018.01); *A61K 2035/115* (2013.01)

(58) Field of Classification Search
None
See application file for complete search history.

(56) References Cited

U.S. PATENT DOCUMENTS

| | | | | |
|---|---|---|---|---|
| 2013/0064927 A1* | 3/2013 | Davis | .................. | C12N 1/205 435/252.5 |
| 2017/0296608 A1* | 10/2017 | Lin | .................. | A23L 33/40 |
| 2018/0094327 A1 | 4/2018 | Penet et al. | | |

FOREIGN PATENT DOCUMENTS

| | | | |
|---|---|---|---|
| CN | 107912607 A | | 4/2018 |
| KR | 20120116802 | * | 10/2012 |

OTHER PUBLICATIONS

Eng.MT—Lim, et al. Korean Patent Application Publication No. KR20120116802. Fermented soybean containing *Bacillus subtilis* subsp. *inaquosorum* FA 0305 enhanced functionality of anti-diabetes and method thereof. Pub. Date: Oct. 19, 2012, pp. 1-8; specif. pp. 4, 7.*
Ito, H. et al. 2004. Excess accumulation of body fat is related to dyslipidemia in normal-weight subjects. International Journal of Obesity 28: 242-247; specif. pp. 242, 246.*
Heming, A. 2016. 8 Rules for fat loss training. T Nation. Datasheet [online]. Retrieved on Dec. 8, 2020; Downloaded from the internet at: https://www.t-nation.com/training/8-rules-for-fat-loss-training; pp. 1-6; specif. pp. 1, 2, 3, 4, 5.*
Poliquin Group. 2014. The ultimate but practical guide to achieving optimal body composition. Poliquin Group. Retrieved on Nov. 1, 2021; Downloaded from the internet at: https://www.poliquin.group.com/ArticlesMultimedia/Articles/PrinterFriendly.aspx?ID=1231&lang=EN. pp. 1-5; specif. pp. 1, 2, 3, 4.*
Rooney, A.P. et al. 2009. Phylogeny and molecular taxonomy of the *Bacillus subtilis* species complex and description of *Bacillus subtilis* subsp. *inaquosorum* subsp. *nov*. International Journal of Systematic and Evolutionary Microbiology 59: 2429-2436; specif. p. 2433.*
Townsend, J.R. et al. Sep. 12, 2017. The effect of probiotic supplementation on body composition, muscle thickness, and athletic performance in Division I collegiate athletes. Journal of the International Society of Sports Nutrition 14(Suppl. 2)(31): 1-28; specif. pp. 24-25, Abstract P53. Conf. held Jun. 22-24.*
Derosa, G. et al. 2012. Alpha-glucosidase inhibitors and their use in clinical practice. Archives of Medical Science 8(5): 899-906; specif. pp. 903, 903.*
Townsend, J.R. et al. 2018. Effects of probiotic (Bacillus subtilis DE111) supplementation on immune function, hormonal status, and physical performance in Division I baseball players. Sports 6(70): 1-18; specif. pp. 1, 9, 10.*
Brochu, M. et al. 2000. Obesity, body fat distribution, and coronary artery disease. Journal of Cardiopulmonary Rehabilitation 20(2): 96-108; specif. p. 96.*
Natural Products Insider. Jun. 6, 2017. DE111 probiotic provides benefits for body fat percentage and athletic performance. Datasheet [online]. Retrieved from the internet: <https://www.naturalproductsinsider.com/probiotics/de111-probiotic-provides-benefits-body-fat-percentage-and-athletic-performance> pp. 1-3.*
Andrea T. Borchers, et al., "Probiotics and Immunity," 44 J. Gastroenterology 26 (2009).
Allison Clark & Nuria Mach, "The Crosstalk between the Gut Microbiota and Mitochondria during Exercise," 8 Frontiers in Physiology Article 319 (2017).
Erick Prado De Oliveira, et al., "Gastrointestinal Complaints During Exercise: Prevalence, Etiology, and Nutritional Recommendations," 44 (Suppl. 1) Sports Medicine S79 (2014).
M.V. Franchi, et al., "Muscle thickness correlates to muscle cross-sectional area in the assessment of strength training-induced hypertrophy," 28 Scandinavian J. Medicine & Science in Sports 846 (2018).
M. Gleeson, et al., "Daily probiotic's (lactobacillus casei shirota) reduction of infection incidence in athletes," 21 Int'l J. Sport Nutrition & Exercise Metabolism 55 (2011).

(Continued)

*Primary Examiner* — Adam Weidner
*Assistant Examiner* — Sharon M. Papciak
(74) *Attorney, Agent, or Firm* — Amin Wasserman Gurnani LLP; George M. Carrera, Jr.; Valerie Neymeyer-Tynkov

(57) ABSTRACT

The present invention relates to methods of improving body composition and reducing body fat percentage in an individual. The present invention relates to methods comprising administering to an individual a *Bacillus subtilis* composition wherein the individual's body fat percentage is reduced.

11 Claims, 2 Drawing Sheets

(56) References Cited

OTHER PUBLICATIONS

A. Hanifi, et al., "Evaluation of Bacillus subtilis R0179 on gastrointestinal viability and general wellness: a randomised, double-blind, placebo-controlled trial in healthy adults," 6 Beneficial Microbes 19 (2015).
Jay R. Hoffman, et al., "Efficacy of phosphatidic acid ingestion on lean body mass, muscle thickness and strength gains in resistance-trained men," 9 J. Int'l Soc'y of Sports Nutrition 47 (2012).
Ralf Jager, et al., "Probiotic *Streptococcus thermophilus* FP4 and Bifidobacterium breve BR03 Supplementation Attenuates Performance and Range-of-Motion Decrements Following Muscle Damaging Exercise," 8 Nutrients 642 (2016).
Ralf Jager, et al., "Probiotic Bacillus coagulans GBI-30, 6086 reduces exercise-induced muscle damage and Increases recovery," 4 PEERJ e2276 (2016).
Ralf Jager, et al., "International Society of Sports Nutrition Position Stand: protein and exercise," 14 J. Int'l Soc'y of Sports Nutrition 20 (2017).
Adam R. Jajtner, et al., "Performance and Muscle Architecture Comparisons Between Starters and Nonstarters in National Collegiate Athletic Association Division I Women's Soccer," 27 J. of Strength & Conditioning Research 2355 (2013).
Reiner Jumpertz, et al., Energy-balance studies reveal associations between gut microbes, caloric load, and nutrient absorption in humans, 94 Am. J. Clinical Nutrition 58 (2011).
Y. Kadooka, et al., "Regulation of abdominal adiposity by probiotics (Lactobacillus gasseri SBT2055) in adults with obese tendencies in a randomized controlled trial," 64 Eur. J. Clinical Nutrition 636 (2010).
Jurgen Karczewski, et al., "Regulation of human epithelial tight junction proteins by Lactobacillus plantarum in vivo and protective effects on the epithelial barrier," 298 Am. J. Physiology Gastrointestinal Liver Physiology G851 (2010).
A.J.H. Maathuis, et al., "Survival and metabolic activity of the GanedenBC30 strain of Bacillus coagulans in a dynamic in vitro model of the stomach and small intestine," 1 Benefical Microbes 31 (2010).
Nuria Mach & Dolors Fuster-Botella, Endurance exercise and gut microbiota: A review, 6 J. Sport & Health Sci. 179 (2017).
Megan A. McCrory, et al., "Body composition by air-displacement plethysmography by using predicted and measured thoracic gas volumes," 84 J. Applied Physiology 1475 (1998).
M.M. Minett, et al., "Changes in body composition and bone of female collegiate soccer players through the competitive season and off-season," 17 J. Musculoskeletal & Neuronal Interactions 386 (2017).
Jaclyn M. Omar, et al., "Lactobacillus fermentum and Lactobacillus amylovorus as probiotics alter body adiposity and gut microflora in healthy persons," 5 J. Functional Foods 116 (2013).
Kristin L. Osterberg, et al., "Probiotic Supplementation Attenuates Increases in Body Mass and Fat Mass During High-Fat Diet in Healthy Young Adults," 23 Obesity 2364 (2015).
Marina Sanchez, et al., "Effect of Lactobacillus rhamnosus CGMCC1. 3724 supplementation on weight loss and maintenance in obese men and women," 111 British J. Nutrition 1507 (2014).
Lotta K. Stenman, et al., "Probiotic With or Without Fiber Controls Body Fat Mass, Associated With Serum Zonulin, in Overweight and Obese Adults—Randomized Controlled Trial," 13 Ebiomedicine 190 (2016).
Kim Van Wijck, et al., "Exercise-Induced Splanchnic Hypoperfusion Results in Gut Dysfunction in Healthy Men," 6 PLOS One e22366 (2011).
Kim Van Wijck, et al., "Dietary protein digestion and absorption are impaired during acute postexercise recovery in young men," 304 American J. Physiology. Regulatory, Integrative & Comparative Physiology R356 (2013).
M. Veldhorst, et al., "Protein-induced satiety: Effects and mechanisms of different proteins," 94 Physiology & Behavior 300 (2008).
Nicholas P. West, et al., "Lactobacillus fermentum (PCC) supplementation and gastrointestinal and respiratory-tract illness symptoms: a randomised control trial in athletes," 10 Nutrition J. 30 (2011).
Nicholas P. West, et al., "Probiotic supplementation for respiratory and gastrointestinal illness symptoms in healthy physically active individuals," 33 Clinical Nutrition 581 (2014).
Colin D. Wilborn, et al., "The Effects of Pre- and Post-Exercise Whey vs. Casein Protein Consumption on Body Composition and Performance Measures in Collegiate Female Athletes," 12 J. Sports Sci. & Nutrition 74 (2013).
Parra, V. et al. 2010. "Modification of the fat composition of the Iberian pig using Bacillus licheniformis and Bacillus subtilis." European Journal of Science and Technology 112: 720-726. specif. pp. 720, 721, 723, 724.
Prince J. Jul. 14, 2017. Nutritional Outlook. Datasheet [online]. Retrieved: Apr. 20, 2020. Retrieved from the internet: <https://www. n utriti onaloutl ook. com/digestive-health/ spore-forming-probiotic-may-reduce-body-fat-and-improve-athletic-performance-new-study-suggests> pp. 1-5. specif. pp. 2-3.
Vilareal, D.T. et al. May 18, 2017. "Aerobic or resistance exercise, or both, in dieting obese older adults." The New England Journal of Medicine 376: 1943-1955. specif. pp. 1943, 1945, 1949, 1954.
Heming, A. Jan. 22, 2016. "8 rules for fat loss training." T Nation. Datasheet [online]. Retrieved on Dec. 8, 2020. Downloaded from the internet: https://www.t-nation.com/training/8-rules-for-fat-loss-training, pp. 1-6. specif. pp. 1, 2, 3, 4, 5.
Anisha, A.H.N. et al. 2015. "Evaluation of *Bacillus* spp as dough starters for Adhirasam—a traditional rice based fermented food of southern India." Brazilian Journal of Microbiology 46(4): 1183-1191. specif. pp. 1183, 1184, 1185, 1187, 1188.
Dunlap et al., "Promotion of *Bacillus subtilis* subsp. *inaquosorum, Bacillus subtilis* subsp. *spizizenii* and *Bacillus subtilis* subsp. *stercoris*. to species status", Antonie Van Leeuwenhoek, Jan. 2020; 113(1):1-12 (Abstract only).
Han et al., "Effects of Coleus forskohlii on Fat Storage in Ovariectomized Rats" The Pharmaceutical Society of Japan Yakugaku Zasshi 125(5):449-453 (2005).
The Johns Hopkins Patient Guide to Diabetes "Alpha Glucosidase Inhibitors" https:/hopkinsdiabetesinfo.org/medications-for-type-2-diabetes-alpha-glucosidase-inhibitors/ (Mar. 23, 2016) (2 pages).
Kamohara et al., "A Coleus forskohlii extract improves body composition in healthy volunteers: An open-label trial" Personalized Medicine Universe 2:25-27 (Jul. 2013) (presented over 6 pages).
Kamohara et al., "An evidence-based review: Anti-obesity effects of Coleus forskohlii" Personalized Medicine Universe 5:16-20 (Jul. 2016) (presented over 7 pages).
Yi et al., "Genomic insights into the taxonomic status of the three subspecies of *Bacillus subtilis*" Systematic and Applied Microbiology 37:95-99 (2014).

* cited by examiner

PROBIOTIC (*BACILLUS SUBTILIS*) SUPPLEMENTATION FOR IMPROVEMENT OF BODY COMPOSITION IN FEMALE ATHLETES

This application is a Continuation-in-Part of U.S. application Ser. No. 16/141,591, filed on Sep. 25, 2018, which claims the benefit of U.S. Provisional Application No. 62/562,887, filed on Sep. 25, 2017. The disclosures of the prior applications are each incorporated herein by reference in their entireties for all purposes.

TECHNICAL FIELD OF THE INVENTION

The present disclosure relates to methods of improving body composition in a human subject, such as an athlete, with *Bacillus subtilis*-containing composition(s). The *Bacillus subtilis*-containing composition(s) can be used as probiotic supplementation.

BACKGROUND

Interaction between the gut microbiota and host play an important role in the regulation of a multitude of physiological processes. Current evidence suggests that gut-host communication effects cognition, epithelial protection, mitochondrial function, and may shape metabolic and immune network activity. See, e.g., S. Misra & B. Medhi, *Role of probiotics as memory enhancer*, 45 INDIAN J. PHARMACOLOGY 311 (2013); A. Clark & N. Mach, *The crosstalk between the gut microbiota and mitochondria during exercise*, 8 FRONTIERS IN PHYSIOLOGY (2017); N. Mach & D. Fuster-Botella, *Endurance exercise and gut microbiota: a review*, J. SPORT & HEALTH SCI. (2016); each of which is incorporated by reference herein in its entirety.

Strenuous exercise leads to physical stress, which has an impact on the individuals' immune system. Although moderate exercise has a beneficial effect on the immune system, compared with a sedentary lifestyle, excessive amounts of prolonged high-intensity exercise can impair immune function, leading to higher risk of upper respiratory tract infections ("URTIs"). See, e.g., Danica M. Michalickova, et al., *Lactobacillus helveticus Lafti L10 Supplementation Modulates Mucosal and Humoral Immunity in Elite Athletes: A Randomized, Double-Blind, Placebo-Controlled Trial*, 31 J. STRENGTH & CONDITIONING RES. 62 (2017); N. P. Walsh, et al., *Position statement. Part one: Immune function and exercise*, 17 EXERCISE IMMUNOLOGY REV. 6 (2011); each of which is incorporated by reference herein in its entirety. Upper respiratory tract infect occurs in the period of strenuous exercise, particularly during winter months, thus negatively influencing athletes' training and consequently impairing performance during competitions. See, e.g., P. Hellard, et al., *Training-related risk of common illnesses in elite swimmers over a 4-yr period*, 47 MEDICINE & SCI. IN SPORTS & EXERCISE 698 (2015), incorporated by reference herein in its entirety.

Mucosal immunity impairment has been suggested to be a key risk factor for higher URTI incidence in elite athletes. See, e.g., N. P. Walsh, et al., 2011. Secretory IgA is reported to play a multifunctional role in mucosal immunity, including host protection by neutralizing bacterial, viral, and fungal antigens and modulation of epithelial cells. See, e.g., B. Corthesy, et al., *Heliobacter pylori urease B subunit partially protects against challenge with Heliobacter felis*, 192 J. INFECTIOUS DISEASES 1441 (2005); T. S. Kemgang, et al., *Cross-talk between probiotic lactobacilli and host immune system*, 117 J. APPLIED MICROBIOLOGY 303 (2014); each of which is incorporated by reference herein in its entirety. It is generally considered that salivary IgA level decreases in response to high-intensity exercise, especially if it lasts over longer periods of time (>6 months). See, e.g., M. Gleeson, et al., *The missing links in exercise effects on mucosal immunity*, 10 EXERCISE IMMUNOLOGY REV. 107 (2004), incorporated by reference herein in its entirety. Nevertheless, certain discrete dietary changes could compensate for the detrimental effects of strenuous exercise on mucosal immunity. See, e.g., M. Gleeson, et al., 2004. Recent studies suggested that probiotic supplementation could help better mucosal immunity maintenance, or even induce its enhancement. See, e.g., M. Gleeson, et al., *Daily probiotic's (Lactobacillus casei Shirota) reduction of infection incidence in athletes*, 21 INT'L J. OF SPORT NUTRITION & EXERCISE METABOLISM 235 (2012); K. Shimizu, et al., *The effects of Lactobacillus pentosus strain b240 and appropriate physical training on salivary secretory IgA levels in elderly adults with low physical fitness: A randomized, double-blind, placebo-controlled trial*, 54 J. CLINICAL BIOCHEMISTRY & NUTRITION 61 (2014); E. Tiollier, et al., *Effect of a probiotics supplementation on respiratory infections and immune and hormonal parameters during intense military training*, 172 MILITARY MEDICINE 1006 (2007); Y. Wang, et al., *Efficacy of probiotic therapy in full-term infants with critical illness*, 23 ASIA PACIFIC J. CLINICAL NUTRITION 575 (2014); each of which is incorporated by reference herein in its entirety.

As part of immune modulation because of the consumption of probiotics, systemic humoral immune responses could be induced as well. Several studies confirmed that immunoglobulins, main mediators of humoral immunity, were influenced by oral probiotic administration. See, e.g., T. S. Kemgang, et al., 2014; A. C. Ouwehand, et al., *Lactobacillus acidophilus supplementation in human subjects and their resistance to enterotoxigenic Escherichia coli infection*, 111 BRITISH J. NUTRITION 465 (2014); D. Paineau, et al., *Effects of seven potential probiotic strains on specific immune responses in healthy adults: A double-blind, randomized, controlled trial*, 53 FEMS IMMUNOLOGY & MEDICAL MICROBIOLOGY 107 (2008); K. N. Sindhu, et al., *Immune response and intestinal permeability in children with acute gastroenteritis treated with Lactobacillus rhamnosus GG: A randomized, double-blind, placebo-controlled trial*, 58 CLINICAL INFECTIOUS DISEASES 1107 (2014); each of which is incorporated by reference herein in its entirety. In addition, enhancement of specific humoral response would be of special interest for professional athletes in terms of prevention of bacterial infections and minimization of their detrimental impact on training and performance.

In performance sports there is a high prevalence of GI complaints among endurance athletes like runners and triathletes. See, e.g., M. Lamprecht, *Probiotic supplementation affects markers of intestinal barrier, oxidation, and inflammation in trained men; a randomized, double-blinded, placebo-controlled trial*, 9 J. INT'L SOC'Y SPORTS NUTRITION 45 (2012); N. J. Rehrer, et al., *Physiological changes and gastro-intestinal symptoms as a result of ultra-endurance running*, 64 EUR. J. APPLIED PHYSIOLOGY & OCCUPATIONAL PHYSIOLOGY 1 (1992); each of which is incorporated by reference herein in its entirety. These problems are attributed to changed blood flow, which is shunted from the viscera to skeletal muscle or the heart. See, e.g., M. I. Qarnar & A. E. Read, *Effects of exercise on mesenteric blood flow in man*, 28 GUT 583 (1987), incorporated by reference herein in its entirety. Such exercise-induced reductions in intestinal blood flow as well as exercise-linked thermal damage to the intestinal mucosa can cause intestinal barrier disruption, followed by an inflammatory response. See, e.g., G. P. Lambert, *Stress-induced gastrointestinal barrier dysfunction and its inflammatory effects,* 87 (E. Suppl.) J. ANIMAL SCI. E101 (2009), incorporated by reference herein in its entirety. Symptoms described are nausea, stomach and intestinal cramps, vomiting, and diarrhea. The increased permeability of the intestinal wall leads to endotoxemia, and results in increased susceptibility to infectious- and autoimmune diseases, due to absorption of pathogens/toxins into tissue and blood stream. See, e.g., N. P. West, et al., *Probiotics, immunity and exercise: a review,* 15 EXERCISE IMMUNOLOGY REV. 107 (2009); A. Fasano, *Leaky gut and autoimmune diseases,* 42 CLINICAL REVS. IN ALLERGY & IMMUNOLOGY 71 (2012); E. P. DeOliveira & R. C. Burini, *Food-dependent, exercise-induced gastrointestinal distress,* 8 J. INT'L SOC'Y SPORTS NUTRITION 12 (2011); each of which is incorporated by reference herein in its entirety. Thus, to reduce exercise-induced GI permeability and its associated symptoms and illnesses, nutritional solutions like probiotic supplementation may be of relevance for athletes and also a real challenge for the probiotic industry to develop bioeffective products.

Tight junctions are protein structures that represent the major barrier within the intestinal paracellular pathway. Tight junctions seal the paracellular space between epithelial cells and regulate the movement of fluid, macromolecules, and leukocytes between the bloodstream and the intestinal lumen, and vice versa. See, e.g., A. Fasano, *Pathological and therapeutical implications of macro-molecule passage through the tight junction, in* TIGHT JUNCTIONS 697 (2d ed., M. Cereijido & J. Anderson, eds., CRC Press 2001), incorporated by reference herein in its entirety. Tight junctions consist of more than 50 proteins and are regarded to be key factors of GI permeability. See, e.g., D. Ulluwishewa, et al., *Regulation of tight junction permeability by intestinal bacteria and dietary components,* 141 J. NUTRITION 769 (2011), incorporated by reference herein in its entirety. Commensal and probiotic strains modulate the amount of tight junction proteins at the cell boundaries and can prevent or reverse adverse effects of pathogens. Several probiotic strains such as *Lactobacillus plantarum, Bacteroides thetaiotaomicron* ATCC29184, *Escherichia coli* Nissle 1917, *Bifidobacterium longum* SP 07/3, and *Lactobacillus rhamnosus* GG revealed beneficial impacts on tight junction and intestinal barrier function. See, e.g., H. Qin, et al., *L. plantarum prevents enteroinvasive Escherichia coli-induced tight junction proteins changes in intestinal epithelial cells,* 9 BMC MICROBIOLOGY 63 (2009); R. C. Anderson, et al., *Lactobacillus plantarum DSM 2648 is a potential probiotic that enhances intestinal barrier function,* 309 FEMS MICROBIOLOGY LETTERS 184 (2010); J. Karczewski, et al., *Regulation of human epithelial tight junction proteins by Lactobacillus plantarum in vivo and protective effects on the epithelial barrier,* 298 AM. J. PHYSIOLOGY-GASTROINTESTINAL & LIVER PHYSIOLOGY G851 (2010); S. Resta-Lenert & K. E. Barrett, *Probiotics and commensals reverse TNF-alpha- and IFN-gamma-induced dysfunction in human intestinal epithelial cells,* 130 GASTROENTEROLOGY 731 (2006); S. N. Ukena, et al., *Probiotic Escherichia coli Nissle 1917 inhibits leaky gut by enhancing mucosal integrity,* 12 PLOS ONE e1308 (2007); D. Ghadimi, et al., *Effect of natural commensal-origin DNA on toll-like receptor 9 (TLR9) signaling cascade, chemokine IL-8 expression, and barrier integrity of polarized intestinal epithelial cells,* 16 INFLAMMATORY BOWEL DISEASES 410 (2010); each of which is incorporated by reference herein in its entirety. Moreover, various dietary components like polyphenols, proteins, or amino acids are postulated to regulate epithelial permeability by modifying expression and localization of tight junction proteins in the paracellular space. See, e.g., D. Ulluwishewa, et al., 2011.

Strenuous physical exertion elicits both localized muscular disruptions as well as systemic physiological stress. Evidence suggests that high-intensity exercise may be linked to an impaired gut barrier, resulting in endotoxin translocation, pro-inflammatory cytokine production, and impaired nutrient absorption. Exercise is known to cause gastrointestinal injury and gut barrier dysfunction, reflected by increased small intestinal permeability, bacterial translocation, and inflammation after exercise. See, e.g., T. Marchbank, et al., *The nutraceutical bovine colostrum truncates the increase in gut permeability caused by heavy exercise in athletes,* 300 AM. J. PHYSIOLOGY-GASTROINTESTINAL & LIVER PHYSIOLOGY G477 (2011); O. Oktedalen, et al., *Changes in the gastrointestinal mucosa after long-distance running,* 27 SCANDINAVIAN J. GASTROENTEROLOGY 270 (1992); K. L. Pals, et al., *Effect of running intensity on intestinal permeability,* 82 J. APPLIED PHYSIOLOGY 571 (1997); A. T. Bosenberg, et al., *Strenuous exercise causes systemic endotoxemia,* 65 J. APPLIED PHYSIOLOGY 106 (1988); A. E. Jeukendrup, et al., *Relationship between gastro-intestinal complaints and endotoxemia, cytokine release and the acute-phase reaction during and after a long-distance triathlon in highly trained men,* 98 CLINICAL SCI. 47 (2000); each of which is incorporated by reference herein in its entirety. It has been demonstrated that one hour of exercise induced small intestinal injury, leading to gut barrier dysfunction in healthy young athletes. See, e.g., K. van Wijck, et al., *Exercise-induced splanchnic hyperfusion results in gut dysfunction in healthy men,* 6 PLOS ONE e22366 (2011), incorporated by reference herein in its entirety. Especially during prolonged running or cycling, athletes can experience abdominal pain, and (bloody) diarrhea, which points towards compromised gastrointestinal functioning, but only few studies have looked at exercise-induced intestinal mucosal lesions in man. See, e.g., H. P. Peters, et al., *Gastrointestinal symptoms in long-distance runners, cyclists, and triathletes: prevalence, medication, and etiology,* 94 AM. J. GASTROENTEROLOGY 1570 (1999); O. Oktedalen, et al., 1992; S. C. Choi, et al., *The role of gastrointestinal endoscopy in long-distance runners with gastrointestinal symptoms,* 13 EUR. J. GASTROENTEROLOGY & HEPATOLOGY 1089 (2001); each of which is incorporated by reference herein in its entirety.

For people actively involving physical exercise, for example, athletes, maintenance of the gut barrier is of great interest, as gastrointestinal dysfunction and impaired nutrient absorption may adversely affect acute exercise performance and blunt subsequent training adaptations. See, e.g., Erick Prado de Oliveira, et al., *Gastrointestinal Complaints During Exercise: Prevalence, Etiology, and Nutritional Recommendations,* 44 (Suppl. 1) SPORTS MEDICINE S79 (2014), incorporated by reference herein in its entirety. Gastrointestinal distress is a pervasive problem, especially in ultra-endurance events; nausea, vomiting, abdominal cramping, and diarrhea have been reported in 37-89% of runners participating in races 67-161 kilometers long, and fecal blood loss indicating gastrointestinal hemorrhage was reported in 85% of participants in a 161-kilometer ultra-marathon. See, e.g., R. S. Baska, et al., *Gastrointestinal bleeding during an ultramarathon,* 35 DIGESTIVE DISEASES & SCIS. 276 (1990); M. D. Hoffman & K. Fogard, *Factors related to successful completion of a 161-km ultramarathon,* 6 INT'L J. SPORTS PHYSIOLOGY & PERFORMANCE 25 (2011); N. J. Rehrer, et al., *Physiological changes and gastro-intestinal symptoms as a result of ultra-endurance running,* 64 EUR. J.

APPLIED PHYSIOLOGY 1 (1992); K. J. Suempfle, et al., *Gastrointestinal distress in ultramarathoners is associated with race diet*, 23 INT'L J. SPORTS NUTRITION & EXERCISE METABOLISM 103 (2013); each of which is incorporated by reference herein in its entirety. A recent study investigated gastrointestinal problems in a group of ultra-marathon runners, and observed that 9 of 15 runners experienced gastrointestinal distress, including nausea (89%), abdominal cramps (44%), diarrhea (44%), and vomiting (22%). See, e.g., K. J. Suempfle, et al., 2013. The prevalence of symptoms varies considerably depending on the event, the environmental conditions, and the level of the athlete. Severe gastrointestinal distress ranging from 4% in marathon running and cycling up to 32% in Ironman races has been reported. See, e.g., B. Pfeiffer, et al., *Nutritional intake and gastrointestinal problems during competitive endurance events*, 44 MEDICINE & SCI. IN SPORTS & EXERCISE 344 (2012), incorporated by reference herein in its entirety. Gastrointestinal symptoms can also affect performance and, in extreme cases, have longer-term health implications. In one study, 43% of triathletes reported serious gastrointestinal problems, and 7% abandoned the race because of gastrointestinal problems. See, e.g., A. E. Jeukendrup, et al., 2000. In two 161-kilometer ultra-marathons, nausea and/or vomiting were the main reasons for dropping out among non-finishers and were the second most common problem impacting race performance among finishers. See, e.g., M. D. Hoffman, et al., 2011.

The term "probiotics" can refer to live microorganisms which when administered in adequate amounts confer a health benefit on the host. See, e.g., FAO/WHO, *Health and Nutrition Properties of Probiotics in Food including Powder Milk with Live Lactic Acid Bacteria Report of a Joint FAO/WHO Expert Consultation on Evaluation of Health and Nutritional Properties of Probiotics in Food including Powder Milk with Live Lactic Acid Bacteria*, Report 2001, Cordoba, Argentina, 1-4 Oct. 2001, Report No. 0254-4725, incorporated by reference herein in its entirety. *Lactobacillus* and *Bifidobacterium* are the most commonly used bacterial probiotics.

Probiotics employ benefits to their hosts primarily by supporting the proliferation of beneficial gut microflora. The intestinal microbiota is the largest source of microbial stimulation that has potential for both harmful as well as beneficial impact in human health and sickness. See, e.g., Anil Minocha, *Probiotics for Preventive Health*, 24 NUTRITION IN CLINICAL PRACTICE 227 (2009), incorporated by reference herein in its entirety. About 60-80% of immune system components can be found in the gut. As such, attention has been focused on the role of probiotics in boosting immunity to prevent or treat infections, chronic inflammatory diseases, and allergic disorders. Numerous animal studies have documented the immune-boosting properties of probiotics. It has been demonstrated that formula acidified with live *Lactococcus lactis* formula provided superior protection against pulmonary and GI bacterial colonization as well as translocation in rabbits. See, e.g., M. R. McVay, et al., *Formula fortified with live probiotic culture reduces pulmonary and gastrointestinal bacterial colonization and translocation in a newborn animal model*, 43 J. PEDIATRIC SURGERY 25 (2008), incorporated by reference herein in its entirety. When children attending child care centers take probiotics, it reduces infections, suggesting that probiotics impede the spread of infections. See, e.g., Z. Weizman, et al., *Effect of a probiotic infant formula on infections in child care centers: comparison of two probiotic agents*, 115 PEDIATRICS 5 (2005); C. W. Binns, et al., *The CUPDAY study: prebiotic probiotic milk product in 1-3-year-old children attending childcare centres*, 96 ACTA PAEDIATRICA 1646 (2007); each of which is incorporated by reference herein in its entirety. There is potential for a 20% reduction in the duration of winter infections in the elderly as a result of probiotic therapy. See, e.g., P. Turchet, et al., *Effect of fermented milk containing the probiotic Lactobacillus casei DN-114001 on winter infections in free-living elderly subjects: a randomized, controlled pilot study*, 7 J. NUTRITION HEALTH & AGING 75 (2003), incorporated by reference herein in its entirety. Regular intake of probiotics can reduce potentially pathogenic bacteria in the upper respiratory tract, suggesting a linkage of the lymphoid tissue between the gut and the upper respiratory tract. See, e.g., U. Gluck & J. O. Gebbers, *Ingested probiotics reduce nasal colonization with pathogenic bacteria (Staphylococcus aureus, Streptococcus pneumoniae, and beta-hemolytic streptococci)*, 77 AM. J. CLINICAL NUTRITION 517 (2003), incorporated by reference herein in its entirety.

Further, probiotics are reported to exert their beneficial effects by producing bacteriostatic or bactericidal agents, competitively excluding pathogenic bacteria, or regulating immunomodulatory effects. See, e.g., P. M. Sherman, et al., *Probiotics Reduce Enterohemorrhagic Escherichia coli O157:H7- and Enteropathogenic E. coli O127:H6-Induced Changes in Polarized T84 Epithelial Cell Monolayers by Reducing Bacterial Adhesion and Cytoskeletal Rearrangements*, 73 INFECTION & IMMUNITY 5183 (2005); S. C. Corr, et al., *Bacteriocin production as a mechanism for the antiinfective activity of Lactobacillus salivarius UCC118*, 104 PROCEEDINGS NAT'L ACADEMY SCIS. 7617 (2007); M. Takahashi, et al., *The effect of probiotic treatment with Clostridium butyricum on enterohemorrhagic Escherichia coli O157:H7 infection in mice*, 41 FEMS IMMUNOLOGY & MEDICAL MICROBIOLOGY 219 (2004); K. Madsen, et al., *Probiotic bacteria enhance murine and human intestinal epithelial barrier function*, 121 GASTROENTEROLOGY 580 (2001); S. Resta-Lenert & K. E. Barrett, 2006; each of which is incorporated by reference herein in its entirety.

Furthermore, probiotics modulate the frequency of the tight junction proteins that act as a barrier in the intestinal paracellular pathway. See, e.g., John R. Kelly, et al., *Breaking down the barriers: the gut microbiome, intestinal permeability and stress-related psychiatric disorders*, 9 FRONTIERS IN CELLULAR NEUROSCIENCE 392 (2015), incorporated by reference herein in its entirety. *B. lactis* augmented formula, fed to preterm infants, resulted in decreased intestinal permeability as measured by the lactulose/mannitol ratio at two, seven, and thirty days post birth. See, e.g., Z. Stratiki, et al., *The effect of a bifidobacter supplemented bovine milk on intestinal permeability of preterm infants*, 83 EARLY HUMAN DEVELOPMENT 575 (2007), incorporated by reference herein in its entirety. In a double-blinded, placebo-controlled, crossover study *L. rhamnosus* 19070-2 and *L. reuteri* DSM 12246 were administered for six weeks to 41 children with moderate and severe atopic dermatitis, decreasing associated GI symptoms and influencing small intestinal permeability as measured by the lactulose-mannitol test. See, e.g., V. Rosenfeldt, et al., Effect of probiotics on gastrointestinal symptoms and small intestinal permeability in children with atopic dermatitis, 145 *J. PEDIATRICS* 612 (2004), incorporated by reference herein in its entirety. Some of the strongest evidence for the clinical role of probiotics comes from studies in patients with the brain-gut-axis disorder, IBS. See, e.g., K. Whelan & E. M. Quigley, *Probiotics in the management of irritable bowel syndrome and inflammatory bowel disease*, 29 CURRENT OPINION IN GASTROENTEROLOGY 184 (2013); R. Orel & T. Kamhi Trop, *Intestinal microbiota,*

*probiotics and probiotics in inflammatory bowel disease*, 20 WORLD J. GASTROENTEROLOGY 11505 (2014); each of which is incorporated by reference herein in its entirety. A number of probiotics and commensal organisms, primarily lactic acid bacteria, have been shown to ameliorate certain IBS symptoms. See, e.g., N. Hoveyda, et al., *A systematic review and meta-analysis: probiotics in the treatment of irritable bowel syndrome*, 9 BMC GASTROENTEROLOGY 15 (2009); G. Clarke, et al., *Review article: probiotics for the treatment of irritable bowel syndrome focus on lactic acid bacteria*, 35 ALIMENTARY PHARMACOLOGY & THERAPEUTICS 403 (2012); M. Ortiz-Lucas, et al., *Effect of probiotic species on irritable bowel syndrome symptoms: a bring up to date meta-analysis*, 105 REVISTA ESPAÑOLA DE ENFERMEDADES DIGESTIVAS 19 (2013); J. S. Yoon, et al., *Effect of multi-species probiotics on irritable bowel syndrome: a randomized, double-blind, placebo-controlled trial*, 29 J. GASTROENTEROLOGY & HEPATOLOGY 52 (2014); T. Didari, et al., *Effectiveness of probiotics in irritable bowel syndrome: updated systematic review with meta-analysis*, 21 WORLD J. GASTROENTEROLOGY 3072 (2015); each of which is incorporated by reference herein in its entirety. Some beneficial effects of probiotics on IBS symptoms may, at least, relate to the anti-inflammatory effects of particular organisms. See, e.g., L. O'Mahony, et al., *Lactobacillus and Bifidobacterium in irritable bowel syndrome: symptom responses and relationship to cytokine profiles*, 128 GASTROENTEROLOGY 541 (2005), incorporated by reference herein in its entirety. Moreover, probiotics in accordance with pre-clinical evidence can improve intestinal barrier function under pathological conditions in human populations. In a randomized single blind placebo controlled study, a fermented milk drink containing *Streptococcus thermophiles, L. bulgaricus, L. acidophilus*, and *B. longum* decreased small intestinal permeability, though colonic permeability was unaltered. See, e.g., J. Zeng, et al., *Clinical trial: effect of active lactic acid bacteria on mucosal barrier function in patients with diarrhea-predominant irritable bowel syndrome*, 28 ALIMENTARY PHARMACOLOGY & THERAPEUTICS 994 (2008), incorporated by reference herein in its entirety.

By enhancing intestinal barrier function, probiotics serve as preventative agents to defend against adverse effects of pathogens, promoting positive effects on digestion and immune health. See, e.g., Jurgen Karczewski, et al., 2010; M. Gleeson, et al., 2011. Certain probiotic strains have given significant and promising results in human clinical trials and experimental animal models of gastrointestinal disease. The enhancement of epithelial barrier function is one of the proposed mechanisms by which certain probiotic organisms may confer beneficial activities. See, e.g., I. Dotan & D. Rachmilewitz, *Probiotics in inflammatory bowel disease: possible mechanisms of action*, 21 CURRENT OPINION IN GASTROENTEROLOGY 426 (2005), incorporated by reference herein in its entirety. Some probiotic studies in humans have reported a decrease in intestinal permeability, whereas others have been negative or inconclusive, suggesting that this activity may depend on the probiotic strain and species as well as the target population and its resilience capacity of the intestinal mucosa. See, e.g., V. Rosenfeldt, et al., 2004; Z. Stratiki, et al., 2007; M. Gotteland, et al., *Effect of Lactobacillus ingestion on the gastrointestinal mucosal barrier alterations induced by indomethacin in humans*, 15 ALIMENTARY PHARMACOLOGY & THERAPEUTICS 11 (2001); C. E. McNaught, et al., *A prospective randomized trial of probiotics in critically ill patients*, 24 CLINICAL NUTRITION 211 (2005); each of which is incorporated by reference herein in its entirety. Evidence for probiotic effects on barrier function has also been demonstrated in rat models of chronic stress, hemorrhagic shock, and sepsis although the mechanisms have not been elucidated. See, e.g., H. L. Qin, et al., *Effect of lactobacillus on the gut microflora and barrier function of the rats with abdominal infection*, 11 WORLD J. GASTROENTEROLOGY 2591 (2005); M. Zareie, et al., *Probiotics prevent bacterial translocation and improve intestinal barrier function in rats following chronic psychological stress*, 55 GUT 1553 (2006); each of which is incorporated by reference herein in its entirety.

There is increasing evidence that probiotic supplementation, alone or in combination with other preventative agents such as prebiotics, can reduce the number, duration, and severity of acute infectious diarrhea and upper respiratory tract infections in the general population and in at-risk subgroups, such as the elderly. See, e.g., Nicholas P. West, et al., *Lactobacillus fermentum (PCC®) supplementation and gastrointestinal and respiratory-tract illness symptoms: a randomized control trial in athletes*, 10 NUTRITION J. 30 (2011); M. de Vrese & J. Schrezenmeir, *Probiotics, prebiotics, and synbiotics*, 111 ADVANCES IN BIOTECHEMICAL ENGINEERING/BIOTECHNOLOGY 1 (2008); M. de Vrese, et al., *Effect of Lactobacillus gasseri PA 16/8, Bifidobacterium longum SP 07/3, B. bifidum MF 20/5 on common cold episodes: a double blind, randomized, controlled trial*, 24 CLINICAL NUTRITION 481 (2005); S. Sazawal, et al., *Efficacy of probiotics in prevention of acute diarrhea: a meta-analysis of masked, randomized, placebo-controlled trials*, 6 LANCET INFECTIOUS DISEASES 374 (2006); E. Guillemard, et al., *Consumption of a fermented dairy product containing the probiotic Lactobacillus casei DN-114001 reduces the duration of respiratory infections in the elderly in a randomised controlled trial*, 103 BRITISH J. NUTRITION 58 (2010); each of which is incorporated by reference herein in its entirety. Three studies indicated that probiotic supplementation might be useful for enhancing immunity and reducing the duration of URTIs and gastrointestinal illnesses in endurance-based athletes, whereas probiotic supplementation by commando cadets during a training and combat course had little effect on the incidence of URTIs. See, e.g., M. Gleeson, et al., 2011; R. A. Kekkonen, et al., *The effect of probiotics on respiratory infections and gastrointestinal symptoms during training in marathon runners*, 17 INT'L J. SPORT NUTRITION & EXERCISE METABOLISM 352 (2007); A. J. Cox, et al., *Oral administration of the probiotic Lactobacillus fermentum VRI-003 and mucosal immunity in endurance athletes*, 44 BRITISH J. SPORTS MEDICINE 222 (2010); E. Tiollier, et al., *Effect of a probiotics supplementation on respiratory infections and immune and hormonal parameters during intense military training*, 172 MILITARY MEDICINE 1006 (2007); each of which is incorporated by reference herein in its entirety.

Additionally, it appears that the beneficial effects of probiotics may be strain-specific, with a majority of probiotic studies investigating *Bifidobacterium* and *Lactobacillus* strains in various special groups (i.e., diabetic, obese) of the general population. Overweight Japanese adults exhibited a significantly decreased visceral fat area, body weight, body mass index ("BMI"), and waist and hip circumferences following consumption of fermented milk containing *Lactobacillus gasseri* SBT2055 ("LG2055") at 200 g/d for 12 weeks. See, e.g., Y. Kadooka, et al., *Regulation of abdominal adiposity by probiotics (Lactobacillus gasseri SBT2055) in adults with obese tendencies in a randomized controlled trial*, 64 EUR. J. CLINICAL NUTRITION 636 (2010); Y. Kadooka, et al., *Effect of Lactobacillus gasseri SBT2055 in fermented milk on abdominal adiposity in adults in a randomized controlled trial*, 110 BRITISH J. NUTRITION 1696 (2013); each of which is incorporated by reference herein in its entirety. Small, but significant, body mass and fat mass loss has been reported in individuals with obesity following consumption of some probiotic strains. See, e.g., Kristin L. Osterberg, et al., *Probiotic Supplementation Attenuates Increases in Body Mass and Fat Mass During High-Fat Diet in Healthy Young Adults*, 23 OBESITY 2364 (2015); M. Sanchez, et al., *Effect of Lactobacillus rhamnosus CGMCC1.3724 supplementation on weight loss and maintenance in obese men and women*, 111 BRITISH J. NUTRITION 1507 (2014); each of which is incorporated by reference herein in its entirety. Less body mass and fat mass gain and prevention of insulin resistance was reported in young, healthy subjects consuming a single probiotic strain during 7 days of high-fat overfeeding. See, e.g., C. J. Hulston, et al., *Probiotic supplementation prevents high-fat, overfeeding-induced insulin resistance in human subjects*, 113 BRITISH J. NUTRITION 596 (2015), incorporated by reference herein in its entirety. Rats fed a diet containing fermented skim milk supplemented with LG2055 showed a lower maximal rate of lymphatic lipid absorption compared with rats fed a diet containing non-fermented skim milk, findings which were supported by the observation of increased fecal fatty acid excretion. See, e.g., E. M. Hamad, et al., *Milk fermented by Lactobacillus gasseri SBT2055 influences adipocyte size via inhibition of dietary fat absorption in Zucker rats*, 101 BRITISH J. NUTRITION 716 (2009), incorporated by reference herein in its entirety. Japanese hypertriacylglycerolemic subjects who consumed fermented milk containing LG2055 at 200 g/d for 4 weeks demonstrated significantly decreased postprandial serum lipid concentrations after the intake of oral fat-loading test meals. See, e.g., A. Ogawa, et al., *Lactobacillus gasseri SBT2055 reduces postprandial and fasting serum non-esterified fatty acid levels in Japanese hypertriacylglycerolemic subjects*, 13 LIPIDS IN HEALTH & DISEASE 36 (2014), incorporated by reference herein in its entirety.

Of note, probiotics of the *Bacillus* strain have been shown to be well tolerated, and have garnered attention recently for their potential beneficial effects in an active population. See, e.g., A. Hanifi, et al., *Evaluation of Bacillus subtilis R0179 on gastrointestinal viability and general wellness: a randomised, double-blind, placebo-controlled trial in healthy adults*, 6 BENEFICIAL MICROBES 19 (2014); R. Jäger, et al., *Probiotic Bacillus coagulans GBI-30, 6086 reduces exercise-induced muscle damage and increases recovery*, 4 PEERJ e2276 (2016); each of which is incorporated by reference herein in its entirety.

To date, there are limited clinical data as to the efficacy of probiotic administration in the athletic population. A bulk of the current literature shows promising effects of probiotics for prevention of acute and chronic illness in endurance athletes during times of intense training. See, e.g., *Probiotic supplementation for respiratory and gastrointestinal illness symptoms in healthy physically active individuals*, 33 CLINICAL NUTRITION 581 (2014), incorporated by reference herein in its entirety. Studies also show that probiotics may have immunomodulatory properties that could aid in the acute regenerative capacity of skeletal muscle repair and functional recovery. However, much less is known about the potential benefits probiotics may confer to athletes who regularly engage in resistance exercise. Recently, it has been reported that co-ingestion of a probiotic supplement and protein following muscle-damaging exercise resulted in a modest reduction of muscle damage markers with improved functional recovery 24- and 72-hours post-exercise. See, e.g., R. Jäger, et al., 2016.

Additionally, it was shown that 21 days of probiotic supplementation attenuated circulating IL-6 concentrations and range of motion decrements following muscle-damaging eccentric exercise. See, e.g., Ralf Jäger, et al., *Probiotic Streptococcus thermophilus FP4 and Bifidobacterium breve BRO3 Supplementation Attenuates Performance and Range-of-Motion Decrements Following Muscle Damaging Exercise*, 8 NUTRIENTS 642 (2016), incorporated by reference herein in its entirety. The training of competitive athletes involves the incorporation of unaccustomed exercise, typically comprising an eccentric component, likely to result in skeletal muscle tissue damage. See, e.g., H. Bruunsgaard, et al., *Exercise-induced increase in serum interleukin-6 in humans is related to muscle damage*, 499 J. PHYSIOLOGY 833 (1997); K. Nosaka, et al., *Effect of elbow joint angle on the magnitude of muscle damage to the elbow flexors*, 33 MEDICINE & SCI. IN SPORTS & EXERCISE 22 (2001); U. Proske, et al., *Muscle damage from eccentric exercise: Mechanism, mechanical signs, adaptation and clinical application*, 537 J. PHYSIOLOGY 333 (2001); each of which is incorporated by reference herein in its entirety. Exercise-induced muscle damage occurs as a result of the forced lengthening of active muscle, which directly causes microtears of the myofibrils, thus disrupting the integrity of the sarcolemma. The initial response, known to result in muscle soreness and swelling, and decreased forced production, is followed by a secondary inflammatory response integral to skeletal muscle repair and recovery response. See, e.g., G. Paulsen, et al., *Leucocytes, cytokines and satellite cells: What role do they play in muscle damage and regeneration following eccentric exercise*, 18 EXERCISE IMMUNOLOGY REV. 42 (2012); J. G. Tidball & S. A. Villalta, *Regulatory interactions between muscle and the immune system during muscle regeneration*, 298 AM. J. PHYSIOLOGY—REGULATORY, INTEGRATIVE, & COMPARATIVE PHYSIOLOGY R1173 (2010); each of which is incorporated by reference herein in its entirety. While inflammation appears to be an important component of muscular adaption to exercise, athletes under heavy training stress or in tournament situations may benefit from a dampening of the inflammatory response to muscle damage and an accelerated recovery period to support the performance of consequent bouts at maximal intensity. Furthermore, consistent training at competition intensity leads to an enhanced adaptation rate and performance. See, e.g., D. J. Smith, *A framework for understanding the training process leading to elite performance*, 33 SPORTS MEDICINE 1103 (2003), incorporated by reference herein in its entirety. Taken together, it appears that probiotics may have immunomodulatory properties that could aid in the acute regenerative capacity of skeletal muscle repair and functional recovery. Furthermore, while some studies have evaluated the potential benefit of probiotics on acute recovery from resistance exercise, to date no study has investigated the effects of probiotics on chronic adaptations to resistance training.

Accordingly, there exists a need for a method of administering *Bacillus subtilis* probiotic supplementation (*B. subtilis* composition) to a human subject actively involved in physical exercise, such as an athlete, to improve muscle thickness and strength, body composition, and athletic performance, and to improve acute recovery between training bouts and athletic adaptation.

SUMMARY OF THE INVENTION

In an embodiment, the present disclosure relates to a method of administration of probiotic supplements (*Bacillus subtilis*-containing composition) for improving body composition in a human subject, such as an athlete. It was unexpected to discover that probiotic supplementation (*Bacillus subtilis*-containing composition), optionally in conjunction with adequate post-workout nutrition, improved body composition in female collegiate athletes in conjunction with off-season resistance training. The probiotic supplement can optionally contain one or more additional components, such as whey protein.

In an embodiment, a method of improving body composition in an individual can include the steps of:
(a) administering orally to the individual a composition comprising *Bacillus subtilis* in a dose of from about $1 \cdot 10^8$ CFU per day to about $1 \cdot 10^{11}$ CFU per day for at least 70 days;
wherein the body fat percentage of the individual is reduced.

The process described herein effects an improvement of body composition in an individual.

In another embodiment, the composition comprises *Bacillus subtilis* in a dose of from about $1 \cdot 10^9$ CFU to about $1 \cdot 10^{10}$ CFU.

In yet another embodiment, the composition comprises *Bacillus subtilis* in a dose of about $5 \cdot 10^9$ CFU.

In yet another embodiment, the administering step of the method of improving body composition in an individual is performed for at least 90 days.

In yet another embodiment, a method of improving body composition in an individual can include the steps of:
(a) administering orally to the individual a composition comprising *Bacillus subtilis* in a dose of from about $1 \cdot 10^8$ CFU per day to about $1 \cdot 10^{11}$ CFU per day for at least 70 days; (b) submitting the individual to a resistance training program 3 days per week throughout the entire at least 70 days;
wherein the body fat percentage of the individual is reduced.

In yet another embodiment, a method of improving body composition in an individual can include the steps of:
(a) administering orally to the individual a composition comprising *Bacillus subtilis* in a dose of from about $1 \cdot 10^8$ CFU per day to about $1 \cdot 10^{11}$ CFU per day for at least 70 days; (b) submitting the individual to a resistance training program 3 days per week throughout the entire at least 70 days; (c) submitting the individual to a conditioning training program 3 days per week throughout the entire at least 70 days;
wherein the body fat percentage of the individual is reduced.

In yet another embodiment, the body fat percentage of the individual is reduced by at least 1%.

In yet another embodiment, the body fat percentage of the individual is reduced by at least 2%.

In an embodiment, a method of reducing body fat percentage in an individual can include the steps of:
(a) administering orally to the individual a composition comprising *Bacillus subtilis* in a dose of from about $1 \cdot 10^8$ CFU per day to about $1 \cdot 10^{11}$ CFU per day for at least 70 days;
wherein the body fat percentage of the individual is reduced.

The process described herein effects a reduction of body fat percentage in an individual.

In another embodiment, the composition comprises *Bacillus subtilis* in a dose of from about $1 \cdot 10^9$ CFU to about $1 \cdot 10^{10}$ CFU.

In yet another embodiment, the composition comprises *Bacillus subtilis* in a dose of about $5 \cdot 10^9$ CFU.

In yet another embodiment, the administering step of the method of improving body composition in an individual is performed for at least 90 days.

In yet another embodiment, a method of reducing body fat percentage in an individual can include the steps of:
(a) administering orally to the individual a composition comprising *Bacillus subtilis* in a dose of from about $1 \cdot 10^8$ CFU per day to about $1 \cdot 10^{11}$ CFU per day for at least 70 days; (b) submitting the individual to a resistance training program 3 days per week throughout the entire at least 70 days;
wherein the body fat percentage of the individual is reduced.

In yet another embodiment, a method of reducing body fat percentage in an individual can include the steps of:
(a) administering orally to the individual a composition comprising *Bacillus subtilis* in a dose of from about $1 \cdot 10^8$ CFU per day to about $1 \cdot 10^{11}$ CFU per day for at least 70 days; (b) submitting the individual to a resistance training program 3 days per week throughout the entire at least 70 days; (c) submitting the individual to a conditioning training program 3 days per week throughout the entire at least 70 days;
wherein the body fat percentage of the individual is reduced.

In yet another embodiment, the body fat percentage of the individual is reduced by at least 1%.

In yet another embodiment, the body fat percentage of the individual is reduced by at least 2%.

DETAILED DESCRIPTION

Figure 1:
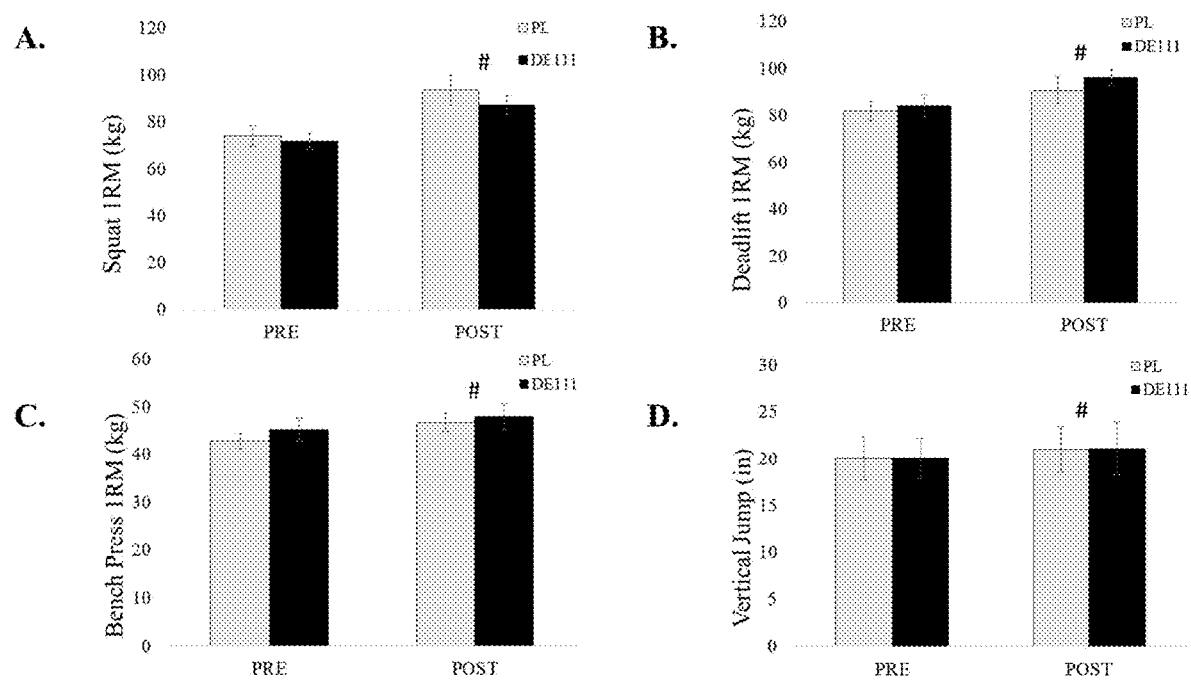
FIG. 1 depicts strength changes following ten weeks of offseason training ("1RM"=1-repetition maximum; "#"=both groups significantly increased compared to pre-values ($p<0.05$)).

In certain embodiments, the present invention relates to a novel use of a *Bacillus subtilis* (*B. subtilis*)-containing composition for probiotic supplementation in an individual. In other embodiments, the present invention relates to a novel use of *Bacillus subtilis* strain DE111 and/or its metabolites for probiotic supplementation of physically active individuals in conjunction with offseason resistance training to improve body composition, including, but not limited to, decreasing body fat percentage.

Embodiments of the present invention encompass methods of improving body composition in an individual, by administering a composition comprising (i) *Bacillus subtilis* DE111, (ii) mutants of *Bacillus subtilis* DE111, (iii) cell-free preparations of (i) or (ii), or (iv) metabolites of (i) or (ii).

As used herein, the term "GI tract" refers to the gastrointestinal tract or pathway in individuals including humans, mammals, and other domesticated animals. The GI tract includes at least the stomach and small intestine, and for test purposes, can include the alimentary canal. Passage or transit through, or residence in, the GI tract is understood to proceed starting from the mouth (via chewing, mastication, liquid delivery, or swallowing, for example), which is followed by ingestion to the stomach, and subsequently to the intestines. Colonization, growth, and maintenance of probiotic bacteria can occur in the GI tract, particularly in the intestines.

Currently, there is a rapid growth of interest in probiotics to promote better health and well-being, which shows a substantial promise to expand the food industry into new fields. Strains from genera of *Lactobacillus* and *Bifidobacterium* species, both of which are indigenous to the human intestine, are predominantly selected for use although some other species have also been used as well. Probiotics, also termed as functional foods, are commonly found in dairy products such as yogurt and cultured milk drinks or even in the form of health supplements.

Useful bacterial strains for probiotic compositions can include, but are not limited to, *Lactobacillus plantarum, Bifidobacterium bifidum, Bifidobacterium lactis, Lactobacillus rhamnosus, Lactobacillus acidophilus, Bacillus coagulans, Bacillus subtilis*, and the like.

The *Bacillus* species are rod-shaped, spore-forming, aerobic, gram-positive bacteria that are ubiquitous in nature. There is some evidence that *Bacillus subtilis* might be a part of the normal gut flora of humans. Some human intestinal biopsy samples have shown that *Bacillus subtilis* does populate the gut in humans as normal human intestinal flora. See, e.g., Junjie Qin, et al., *A human gut microbial gene catalogue established by metagenomics sequencing,* 464 NATURE 59 (2010), incorporated by reference herein in its entirety.

The *Lactobacillus* genus is extremely diverse and expanding every year. With over 230 species, it has grown into one of the biggest genera in the bacterial taxonomy. As the genus has exceeded the acceptable "normal diversity," renaming and re-classification is inevitable wherein the genus *Lactobacillus* may be split into most likely twelve new genera. Many traditional "probiotic" species with substantiated industrial importance and starter cultures may no longer eventually be called "*Lactobacillus*." Hence, a substantial communication challenge looms ahead to reduce the inevitable confusion regarding the "old commercial" and "correct scientific" nomenclature. Once the International Committee on Systematics of Prokaryotes publishes new nomenclature in their official journal, the INTERNATIONAL JOURNAL OF SYSTEMATIC AND EVOLUTIONARY MICROBIOLOGY, the changes are valid and official. The manuscript that will be submitted for publication outlining the new nomenclature of the *Lactobacillus* genus will likely be ready for submission in by the end of 2018. Meanwhile, there is a taxonomic subcommittee meeting in September 2018 to discuss the nomenclature changes and an (invite-only) expert LABIP workshop in October 2018 that will evaluate the science while considering the consequences for regulations, legal/IP, and industry.

*Bacillus subtilis* has been used abundantly in traditional ethnic food processing, for example, in East Asia. Natto, in particular, is a cheese-like food, processed by inoculating soaked and steamed soybeans with life *Bacillus* from rice straw. *Bacillus subtilis* is the main component in the alkaline fermentation of soybeans without salt. Protease and amylase produced by the bacteria decompose protein and insoluble sugar in the raw soybeans, thus increasing the nutritional value as well as the availability of the soybean foods. See, e.g., K. H. Steinkraus, *Fermentations in world food processing,* 1 COMPREHENSIVE REVIEWS IN FOOD SCI. & FOOD SAFETY 23 (2000), incorporated by reference herein in its entirety. Fermentation not only enriches the nutrients but also enhances the health-promoting effectiveness of soybeans. Compared with nonfermented soybeans, fermented soybeans contain significantly more isoflavone genestein, a chemopreventive agent against cancer. See, e.g., F. Fukutake, et al., *Quantification of genistein and genistin in soybeans and soybean products,* 34 FOOD & CHEMICAL TOXICOLOGY 457 (1996); M. J. Messina, et al., *Soy intake and cancer risk: a review of the in vitro and in vivo data,* 21 NUTRITION & CANCER 113 (1994); each of which is incorporated by reference herein in its entirety.

Gamma-polyglutamic acid ("PGA") is the main component of a stick material in Japanese fermented soybeans (natto) and increases soluble calcium in the small intestine and thereby increases the efficacy of calcium absorption. See, e.g., H. Tanimoto, et al., *Natto mucilage containing poly-gamma-glutamic acid increases soluble calcium in the rat small intestine,* 65 BIOSCIENCE, BIOTECHNOLOGY, & BIOCHEMISTRY 516 (2001), incorporated by reference herein in its entirety. PGA also acts as dietary fiber to reduce the cholesterol level in serum. See, e.g., K. Tsuji & E. Tsuji, *Effect of Natto-feeding on cholesterol level of rats,* 44 JAPAN J. NUTRITION & DIETETICS 41 (1986), incorporated by reference herein in its entirety. Natto extract exhibits antioxidative activity, anti-tumor activity, and angiotensin-I converting enzyme inhibitory activity. See, e.g., H. Esaki, et al., *Antioxidative activity of Natto,* 37 J. JAPANESE SOC'Y FOR FOOD SCI. & TECH. 474 (1990); C. Takahashi, et al., *Possible anti-tumor-promoting activity of components in Japanese soybean fermented food, Natto: effect on gap functional intercellular communication,* 16 CARCINOGENESIS 471 (1995); A. Okamoto, et al., *Angiotensin I converting enzyme inhibitory activity of various fermented foods,* 59 BIOSCIENCE, BIOTECHNOLOGY, & BIOCHEMISTRY 1147 (1995); each of which is incorporated by reference herein in its entirety.

Certain strains of *Bacillus subtilis* isolated from natto produce subtilisin NAT (formerly designated BSP, or nattokinase), which exhibits strong fibrinolytic activity. See, e.g., H. Sumi, et al., *Enhancement of the fibrinolytic activity in plasma by oral administration of natto kinase,* 84 ACTA HAEMATOLOGICA 139 (1990); M. Fujita, et al., *Thrombolytic effect of nattokinase on a chemically induced thrombosis model in rat,* 18 BIOLOGICAL & PHARM. BULLETIN 1387 (1995); each of which is incorporated by reference herein in its entirety. Subtilisin NAT-producing *Bacillus* strains have been isolated not only from natto but also from fermented soybean foods from Korea, Taiwan, and China. Dietary supplementation with natto suppresses intimal thickening and modulates the lysis of mural thrombi. See, e.g., Y. Suzuki, et al., *Dietary supplementation with fermented soybeans suppresses intimal thickening,* 19 NUTRITION 261 (2003); Y. Suzuki, et al., *Dietary supplementation of fermented soybean, natto, suppresses intimal ticking and modulates the lysis of mural thrombi after endothelial injury in rat femoral artery,* 73 LIFE SCIS. 1289 (2003); each of which is incorporated by reference herein in its entirety. Both the decrease in thrombus count and plasma euglobulin and the increase in tissue plasminogen activator are caused by oral intake of *Bacillus subtilis* BN-1 strain. See, e.g., H. Sumi, et al., *Natto Bacillus as an oral fibrinolytic agent: nattokinase activity and the ingestion effect of Bacillus subtilis natto,* 10 FOOD SCI. & TECH. RES. 17 (2004), incorporated by reference herein in its entirety. However, those two effects might partially be due to subtilisin NAT, although the mechanism for the enzyme to potentiate fibrinolysis in vivo is not yet fully understood. See, e.g., T. Urano, et al., *The profibrolytic enzyme subtilisin NAT purified from Bacillus subtilis claves and inactivates plasminogen activator inhibitor type* 1, 276 J. BIOLOGICAL CHEMISTRY 24690 (2001), incorporated by reference herein in its entirety.

"Thua nao" is a traditional fermented soybean food produced in northern Thailand. See, e.g., A. Leejeerajumnean, et al., *Volatile compounds in Bacillus-fermented soybean*, 81 J. SCI. FOOD & AGRICULTURE 525 (2001), incorporated by reference herein in its entirety. Typically, Thua nao is produced by first boiling and mashing soybeans, and then fermenting the soybeans in banana leaves for 2-3 days at ambient temperature. Alternatively, boiled, mashed soybeans are dried outdoors in the sun. Sun-dried Thua nao can be stored for several months at room temperature. See, e.g., P. Chantawannakul, et al., *Characterization of protease of Bacillus subtilis strain 38 isolated from traditionally fermented soybean in Northern Thailand*, 28 SCI. ASIA 241 (2002), incorporated by reference herein in its entirety. Similar sun-dried fermented soybean foods are also produced in Nepal, in Yunnan province of China, and in northern Laos and Myanmar. See, e.g., Y. Inatsu, et al., *Characterization of Bacillus subtilis strains isolated from fermented soybean foods in southeast Asia: comparison with B. subtilis (natto) starter strains*, 36 JAPAN AGRICULTURAL RES. QUARTERLY 525 (2001), incorporated by reference herein in its entirety. Thua nao and other naturally fermented soybean foods are thought to harbor *Bacillus subtilis* strains, which exhibit high potential for producing enzymes such as amylase and protease, and for producing health-promoting compounds such as PGA and protease NAT. Thua nao has been demonstrated to possess a diversity of *Bacillus subtilis*. See, e.g., Y. Inatsu, et al., *Characterization of Bacillus subtilis strains in Thua nao, a traditional fermented soybean food in northern Thailand*, 43 LETTERS IN APPLIED MICROBIOLOGY 237 (2006), incorporated by reference herein in its entirety.

Although the cultural history of *Bacillus subtilis* fermentation is well known, research on modern uses and consumption of *Bacillus subtilis* is comparatively very recent. Clinical trials have shown that *Bacillus subtilis* is safe for consumption, and beneficial for digestive health. *Bacillus subtilis* displays immunostimulating properties and antagonizes gastrointestinal pathogen infection by producing antimicrobial substances such as amicoumacins. See, e.g., Marie Lefevre, et al., *Probiotic strain Bacillus subtilis CU1 stimulates immune system of elderly during common infectious disease period: a randomized, double-blind placebo-controlled study*, 12 IMMUNITY & AGEING 24 (2015), incorporated by reference herein in its entirety.

The term "probiotic" means "for life" in Greek. It was first used in 1965 to name microorganisms that are beneficial to consume. The general health benefits of consuming probiotics have been shown in both animal and human studies. As a component of the human microbiome, *Bacillus subtilis* has the ability to promote gastrointestinal health, including helping its host in digestion, making it an ideal probiotic.

The term "probiotic," as used herein, can refer to viable microorganisms that promote or support a beneficial balance of the autochthonous microbial population of the gut. Alternatively, probiotics can refer to "live microorganisms that may confer a health benefit on the host." These bacterial strains are becoming extremely popular, not only in alternative circles, but also within the scientific community. Scientists have discovered that the microbes that live within animal intestines are important to their health. Animal and human species host at least 1000 different species of bacteria and fungi, and maintaining the right populations of each species is essential. Therefore, maintaining intestinal flora with probiotics is a logical step.

The notion of probiotics evolved from a theory first proposed by Elie Matchnikoff (Nobel laureate), who associated longevity with the consumption of fermented milk products. He postulated that the *Bacillus* present could positively modify the bacterial community structure of the colon, thus contributing to human health status. While not intending to be bound by any theory, the present disclosure is in general agreement with the current understanding of probiotics as used in foods and nutritional/dietary supplements for animals and humans.

The microbial population of the intestine is a highly dynamic and complex ecosystem having an estimated $10^{14}$ microorganisms representing more than 400 bacterial species. It has many functions in humans, including providing enzymes necessary for assimilation and/or synthesis of some nutrients, as well as in detoxifying certain harmful dietary compounds. In addition, the gastrointestinal flora provides a natural barrier against pathogens and can stimulate bowel motility and the immune system.

Probiotic formulations and blends should be able to recover and compete with established microflora in the colon to provide colonization and benefits for the host. For this purpose, they can use help from prebiotics such as inulin.

The gut microbiome influences myriad host functions, including nutrient acquisition, immune modulation, brain development, and behavior. Although human gut microbiota are recognized to change as we age, information regarding the structure and function of the gut microbiome during childhood is limited. A study using 16S rRNA gene and shotgun metagenomics sequencing characterized the structure, function, and variation of the healthy pediatric gut microbiome in a cohort of school-aged, pre-adolescent children (ages 7-12 years). The results showed a difference in the microbiome of the children vs. adults on many strains of bacteria. Children were enriched in *Bifidobacterium* spp., *Faecalibacterium* spp., and members of the Lachnospiraceae, while adults harbored greater abundances of *Bacteroides* spp. From a functional perspective, significant differences were detected with respect to the relative abundances of genes involved in vitamin synthesis, amino acid degradation, oxidative phosphorylation, and triggering mucosal inflammation. Children's gut communities were enriched in functions which may support ongoing development, while adult communities were enriched in functions associated with inflammation, obesity, and increased risk of adiposity. See, e.g., Hollister, et al., *Structure and function of the healthy pre-adolescent pediatric gut microbiome*, 3 MICROBIOME 36 (2016), incorporated by reference herein in its entirety.

Recently, probiotics therapy, evidenced by numerous randomized clinical trials ("RCTs") followed by meta analyses and Cochran reviews, has generated a great deal of renewed interest, due to its significant therapeutic effect on rotavirus-associated diarrhea in children in developed countries. The most commonly used strains of probiotics belong to the genera *Lactobacillus* and *Bifidobacterium*, *L. rhamnosus* GG, *Saccharomyces boulardii*, *Bacillus clausii*, mix of *L. delbrueckii* var *bulgaricus*, *Streptococcus thermophiles*, *L. acidophilus*, and *Bifidobacterium bifidum*, or *Enterococcus faecium* SF 68. The median duration of diarrhea was significantly shorter and the frequency was lower only in those children who received mixes of four bacterial strains. See, e.g., Dutta, et al., *Randomised controlled clinical trial of Lactobacillus sporogenes (Bacillus coagulans), used as a probiotic in clinical practice, on acute watery diarrhea in children*, 16 TROPICAL MED. INT'L HEALTH 555 (2011), incorporated by reference herein in its entirety.

Furthermore, the issue of the safe application of probiotics is not new or specific to older populations; however, there are aspects that are particular to this age group and that need to be addressed. As has been reviewed of late, the safety of application/consumption of a probiotic is linked to the potential vulnerability of the consumer to specific disease states. See, e.g., Rijkers, et al., *Guidance for substantiating the evidence for beneficial effects of probiotics: current status and recommendations for future research*, 140 J. NUTRITION 671S (2010), incorporated by reference herein in its entirety.

Older people are by definition more likely to present "at-risk" factors, which include immune compromise, central venous catheter, impaired intestinal barrier function, or consumption of broad-spectrum antibiotics to which the probiotic is resistant. See, e.g., Boyle, at al., *Probiotic use in clinical practice: what are the risks?*, 83 J. AM. CLINICAL NUTRITION 1256 (2006), incorporated by reference herein in its entirety. Probiotics have been consumed safely for a long time by the general population, exemplified by the incidence of only one case of *lactobacillus* septicemia among 10 million consumers in France over the course of a century. See, e.g., Bernardeau, et al., *Beneficial lactobacilli in food and feed: long-term use, biodiversity and proposals for specific and realistic safety assessments*, 30 FEMS MICROBIOLOGY REVS. 487 (2006), incorporated by reference herein in its entirety.

Nevertheless, the suitability of therapeutic application of probiotics in older subjects, as distinct from consumption of foods containing probiotic bacteria, should be considered individually and focus on specific needs. Compared with younger adults, populations of older adults consume a complex array of medications, ranging from antibiotics through to pharmaceutical compounds with potential but unknown effects upon the complex bacterial community in the intestine. For example, in the first 360 subjects enrolled in the ELDERMET project, 95 subjects had consumed antibiotics in the 4 weeks prior to their baseline microbiota determination, and 98% had consumed a recognized medicinal compound. See Rijkers, et al., 2010. Probiotics have recognized utility to mitigate the diarrheal side effects of antibiotics and to reduce the incidence of *Clostridium difficile*-associated colitis. See, e.g., Hickson, et al., *Use of probiotic Lactobacillus preparation to prevent diarrhea associated with antibiotics: randomized double blind placebo controlled trial*, 355 BMJ 80 (2007); C. M. Surawicz, et al., *Role of probiotics in antibiotic-associated diarrhea, Clostridium difficile-associated diarrhea, and recurrent Clostridium difficile-associated diarrhea*, 42 (Suppl. 2) J. CLINICAL GASTROENTEROLOGY S64 (2008); each of which is incorporated by reference herein in its entirety. Lifting the burden of infectious disease would be particularly beneficial in older populations.

Several recent comprehensive reviews have summarized the major benefits associated with probiotic consumption in older adults, and such benefits include increased levels of bifidobacteria, reduced constipation, enhanced innate immunity, and reduced inflammation. See, e.g., Pitkala, et al., *Fermented cereal with specific bifidobacteria normalizes bowel movements in elderly nursing home residents. A randomized, controlled trial*, 11 J. NUTRITION, HEALTH, & AGING 305 (2007); Gill, et al., *Enhancement of immunity in the elderly by dietary supplementation with the probiotic Bifidobacterium lactis HNO19*, 74 AM. J. CLINICAL NUTRITION 833 (2001); Ouwehand, et al., *Bifidobacterium microbiota and parameters of immune function in elderly subjects*, 53 FEMS IMMUNOLOGY & MEDICAL MICROBIOLOGY 18 (2008); each of which is incorporated by reference herein in its entirety. Administration of yoghurt fermented by *L. bulgaricus* to older people (n=142; a median age of 74.5 years) significantly reduced the incidence and severity of winter colds and general upper respiratory symptoms. This improvement was accompanied by an increase in natural killer cell activity in the subjects receiving the yoghurt. See, e.g., Makino, et al., *Reducing the risk of infection in the elderly by dietary intake of yoghurt fermented with Lactobacillus delbrueckii ssp. Bulgaricus OLL1073R-1*, 104 BR. J. NUTRITION 998 (2010), incorporated by reference herein in its entirety.

Preclinical validation of beneficial effects in in vitro systems or animal models may thus be beneficial for strain selection, but obviously cannot replace human trials. Older adults as a group in society will typically span a greater range in health status (from healthy and independent to frail and dependent upon assistance). Older adults are known to have microbiota in flux that various significantly more between individuals than in a younger adult population. These factors should be borne in mind when designing clinical trials.

Recent analyses of the microbiota of older adults in Ireland confirmed that the prevalence of the genus *Faecalibacterium* varied significantly between individuals, supporting the notion that levels of this organism might be suitable for therapeutic intervention in older people with intestinal inflammation. Administration of prebiotics, or by administering probiotics that target competing elements in the microbiota, is conceptual at this time. See, e.g., S. Cusack, et al., *How Beneficial is the Use of Probiotic Supplements for the Aging Gut?*, 7 AGING HEALTH 179 (2011), incorporated by reference herein in its entirety.

Furthermore, domesticated animals and/or pet animals can benefit from probiotics. Pet animals may include small or large domestic mammals, for example, but are not limited to, dogs, cats, horses, sheep, cows, cattle, other bovine species, pigs, goats, rabbits, and the like. Also contemplated are small rodent species, including rats, mice, hamsters, gerbils, guinea pigs, and the like.

All dogs can benefit from probiotics, which aid digestion and modulate the immune system. Probiotics produce short-chain fatty acids ("SCFAs"), which inhibit the growth and activity of harmful bacteria, such as *E. coli, Salmonella*, and *Clostridium perfringens*, as well as provide other benefits to the intestines. Human studies have documented the effectiveness of certain strains in treating diarrhea, irritable bowel syndrome, and intestinal inflammation. Probiotics used in dogs may help prevent urinary tract infections, and can even reduce allergic reactions by decreasing intestinal permeability and controlling inflammation.

Research looking at the effectiveness of probiotics in dogs is not nearly as extensive as research of the effectiveness in humans. Still, there are studies that suggest that probiotics can improve or maintain the health of dogs. The diseases that have been investigated so far to determine the effectiveness of probiotics in dogs are acute diarrhea and contact dermatitis (skin allergy).

Acute diarrhea in dogs is diarrhea that starts suddenly and usually results on its own. Probiotics have been tested on several types of acute diarrhea, specifically diarrhea caused by dietary sensitivity and diarrhea caused by the ingestion of an intestinal pathogen. In dogs with dietary sensitivity, treatment with *Lactobacillus acidophilus* in combination with the diarrhea-provoking food led to some improvement in bowel movements. Better results, however, were observed when probiotics were applied as treatments for acute diarrhea caused by a stomach virus.

Probiotic species known to benefit dogs include *Bacillus coagulans*. *Bifidobacterium animalis* has been shown to reduce the time for acute diarrhea to resolve in dogs. *Lactobacillus acidophilus* improved frequency and quality of stools in sensitive dogs. *Lactobacillus rhamnosus* strain GG ("LGG") is effective in preventing and treating diarrhea in humans, and may benefit dogs as well.

*Bifidobacterium animalis* has been studied more in detail. *Bifidobacterium animalis* was chosen for further research because initial studies showed that *Bifidobacterium animalis* had an above-average ability to bind to the gut, a characteristic often associated with beneficial bacteria. Initial studies in dogs showed that *Bifidobacterium animalis* could reduce the pathogenicity of *Salmonella typhiurium* and *Clostridia difficile*, which are bacteria known to induce acute diarrhea. And later, during a treatment study, it was found that *Bifidobacterium animalis* could help acute diarrhea resolve faster.

Dermatitis usually caused by a skin allergy. To treat the dermatitis, one needs to address the underlying immune problems. During allergic responses, the immune system considers a normally harmless substance as a threat. In dogs with a skin allergy, contact of the allergen on the skin causes an immune reaction leading to the classic symptoms of inflammation: itching, redness, and heat. Unfortunately, dogs that develop allergies are usually genetically predisposed to the condition. This means that prevention has to happen at a young age or even when a puppy is still in the womb.

Scientists looked at the ability of *L. rhamnosus* to change the course of allergy in dogs with a genetic predisposition towards allergy. *L. rhamnosus* was given during pregnancy to the mother and to the puppies during weaning. Unfortunately, while there were some significant changes in immunological parameters, the puppies had no real improvements, but a follow-up study performed three years later in the grownup puppies showed that there were differences in the long-term. The immune system was geared towards anti-inflammatory reactions, and the dogs had less dermatitis.

Additionally, many products on the market are of dubious quality. A study testing 19 commercial pet foods, all claiming to contain probiotics, determined that none of the feeds contained what was written on the packages. Only 53% of the tested commercial pet foods contained at least one of the probiotics species listed, and 26% of the tested commercial pet foods had no live bacteria. These results would suggested that using pet food fortified with probiotics is not the wisest route for providing one's pet dog with beneficial bacteria. The recommendation would be to seek out a quality probiotic with the help of a veterinarian.

Probiotics are measured by colony forming units ("CFUs"). Few studies have been done to determine effective dosages, but effective dosages are usually in the hundreds of millions of CFUs or higher. If probiotics are being used to help with digestion, probiotics should be taken with meals, but otherwise the probiotics may survive better if taken between meals, particularly if taken with liquids that help to dilute stomach acid and move the probiotics more quickly into the digestive tract (for example, given after the dog takes a big drink). Probiotics may be given short-term or long-term.

Several studies have revealed that some probiotics products in the market have deficiencies in the viabilities of probiotic strain(s), especially in products containing Bifidobacteria. These deficiencies in viability may be due to storage, manufacturing, or food technology setbacks, such as inappropriate packing materials that could affect probiotic stability through variations in oxygen permeability. In the past two decades, there has been renewed interest in the study of the nutritional and therapeutic aspects of the mentioned products. It is widely accepted that probiotics may exert positive influence on the host through modulation of the endogenous ecosystem and stimulation of the immune system, as well as maintenance of healthy intestinal microflora. However, research suggests that health benefits can be strain-specific and vary by amount ingested and duration administered, even in pets.

One useful *Bacillus subtilis*-containing composition is DE111® ("DE111"), available from Deerland Enzymes, Inc. (Kennesaw, Georgia, United States). DE111 is an isolated strain of *Bacillus subtilis* subspecies *inaquosorum* having accession number NRRL B-67989. The *Bacillus subtilis* subspecies *inaquosorum* (DE111) strain was deposited with the Agricultural Research Service Culture Collection (NRRL), an International Depositary Authority, 1815 N. University Street, Peoria, Illinois, 61604, United States) under the Budapest Treaty on the International Recognition of the Deposit of Microorganisms, on Sep. 28, 2020 and was accepted and found to be viable on Sep. 28, 2020, and assigned accession number NRRL B-67989. The DE111 strain is a biologically pure culture prepared by a proprietary process.

The *Bacillus subtilis* DE111 strain has certain properties, which, surprisingly, have been found to make the strain well-suited for use as a probiotic. Spores of *Bacillus subtilis* are viable under a wide temperature and pH range. Without being bound by any particular theory, it is thought that the ability of *Bacillus subtilis* DE111 to form spores that protect the microbes from harsh conditions until they enter an environment ripe for germination, such as the GI tract, makes *Bacillus* particularly well-suited for use as a probiotic.

In one aspect of the invention, compositions administered to patients in need thereof according to the methods of the present disclosure comprise mutants of *Bacillus subtilis* DE111 having all the identifying characteristics of *Bacillus subtilis* DE111. Such mutants may have DNA sequence identity to *Bacillus subtilis* DE111 of at least about 90%, at least about 91%, at least about 92%, at least about 93%, at least about 94%, at least about 95%, at least about 96%, at least about 97%, at least about 98%, or at least about 99%. In some embodiments, mutants are spontaneous mutants. The teen spontaneous mutant refers to mutants that arise from *Bacillus subtilis* DE111 without the intentional use of mutagens. Such spontaneous mutants may be obtained by classical methods, such as growing the *Bacillus subtilis* DE111 strain in the presence of a certain antibiotic to which the parent is susceptible, and testing any resistant mutants for improved biological activity or, in this application, ability to improve the body composition of an individual. Other methods for identifying spontaneous mutants will be known to those of ordinary skill in the art.

All references in this application to *Bacillus subtilis* DE111 or its mutants refer to bacteria that have been isolated from nature and are grown by humans, for example, in the laboratory or under industrial conditions.

*Bacillus subtilis* DE111 cells may be present in the compositions administered to patients in need thereof according to the methods of the present disclosure as spores (which are dormant), as vegetative cells (which are growing), as transition state cells (which are transitioning from growth phase to sporulation phase) or as a combination of all of these types of cells. In some embodiments, the composition comprises mainly spores. In other embodiments, the composition comprises spores and metabolites produced by the cells during fermentation before they sporulate, as described below.

Compositions administered to patients in need thereof according to the methods of the present disclosure can be obtained by culturing *Bacillus subtilis* DE111 or its mutants according to methods well known in the art. Conventional large-scale microbial culture processes include submerged fermentation, solid state fermentation, or liquid surface culture. Towards the end of fermentation, as nutrients are depleted, *Bacillus subtilis* DE111 cells begin the transition from growth phase to sporulation phase, such that the final product of fermentation is largely spores, metabolites, and residual fermentation medium. Sporulation is part of the natural life cycle of *Bacillus subtilis* DE111 and is generally initiated by the cell in response to nutrient limitation. Fermentation is configured to obtain high levels of colony forming units of *Bacillus subtilis* DE111 and to promote sporulation. The bacterial cells, spores, and metabolites in culture media resulting from fermentation may be used directly or concentrated by conventional industrial methods, such as centrifugation, tangential-flow filtration, depth filtration, and evaporation. In some embodiments, the concentrated fermentation broth is washed, for example, via a diafiltration process, to remove residual fermentation broth and metabolites.

The fermentation broth or broth concentrate can be dried with or without the addition of carriers using conventional drying processes or methods such as spray drying, freeze drying, tray drying, fluidized-bed drying, drum drying, or evaporation. The resulting dry products may be further processed, such as by milling or granulation, to achieve a specific particle size or physical format. Carriers, described below, may also be added post-drying.

In embodiments in which compositions formulated separately from food or drink are administered to patients in need thereof according to the methods of the present disclosure, the concentration on a weight by weight basis (w/w) of (i) *Bacillus subtilis* DE111 or its mutants, (ii) metabolites of *Bacillus subtilis* DE111 or its mutants, or (iii) combinations of cells and metabolites in the formulated composition may be about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90%, or about 95%. In some embodiments of compositions administered to patients in need thereof according to the methods of the present disclosure, where the concentrated formulation broth has been washed and dried without heat, such as via freeze drying, the concentration of *Bacillus subtilis* DE111 or its mutants in the final composition may be from about 90% to about 100%.

In certain embodiments, compositions administered to individuals in need thereof according to the methods of the present disclosure are administered to improve body composition. An effective amount of a composition administered to an individual in need thereof according to the methods of the present disclosure is an amount effective to improve body composition in comparison to an individual who has not been administered the composition but otherwise has been administered the same diet as has an individual administered the composition according to methods of the present disclosure. In other embodiments, an effective amount of a composition administered to an individual in need thereof according to the methods of the present disclosure is an amount effective to reduce body fat percentage in comparison to an individual who has not been administered the composition but otherwise has been administered the same diet as has an individual administered the composition according to the methods of the present disclosure.

Thus, in line with the above, embodiments of the present disclosure are directed to methods of improving body composition, and/or reducing body fat percentage, by administering to an individual in need thereof a composition comprising *Bacillus subtilis* DE111, a mutant of *Bacillus subtilis* DE111, metabolites of *Bacillus subtilis* DE111 or its mutants, or combinations of *Bacillus subtilis* DE111 or a mutant and metabolites of *Bacillus subtilis* DE111 or its mutants.

Without wishing to be bound by any particular theory, it is thought that increases to beneficial bacteria may be caused by stimulating growth of such bacteria or simply by selectively decreasing pathogenic bacteria, thereby giving the beneficial bacteria more space to grow and to attach to the gut wall and/or more efficient access to nutrients and growth factors. In addition, or alternatively, beneficial bacteria may modify the virulence factors of pathogenic bacteria, thus decreasing the virulence of the pathogenic bacteria. Harmful, disease-causing bacteria that may be decreased by the methods of the present disclosure include *Clostridia* spp. (such as *perfringens* and *dificille*), *Listeria* spp. (such as *Moncytogenes*, *seeligeri*, and *welshimeri*), *Salmonella* spp. (such as *enterica*, *arizonae*, *typhirium*, *enteridis*, and *bonglori*), *E. coli*, *Enterococus* spp. (such as *faecalis* and *faecium*), *Camphylobacter*, *Aeromonas* spp., *Staphylococcus aureus*, *Shigella dysenteria*, and *Vibrio* spp. In some embodiments, harmful, disease-causing microorganisms may be reduced by about 0.5 log, about 1 log, about 2 log, about 3 log, about 4 log, or about 5 log.

In another aspect, compositions administered according to methods of the present disclosure comprising *Bacillus subtilis* DE111, its mutants, and/or metabolites of *Bacillus subtilis* DE111 and/or its mutants may further include or be administered with other probiotics, such as other bacterial spore formers. Examples of probiotics are provided in H. A. Hong, et al., *The use of bacterial spore formers as probiotics*, 29 FEMS MICROBIOLOGY REVS. 813 (2005), incorporated by reference herein in its entirety.

In yet another aspect, compositions administered according to methods of the present disclosure may include or be administered with (either at the same time or at different times) anti-diarrheal agents, anti-gas agents, dietary fibers, antibiotics, such as methotrexate, anti-inflammatory drugs, amino acids, electrolytes, vitamins, and minerals.

In embodiments in which the compositions administered according to methods of the present disclosure comprise *Bacillus subtilis* DE111 or its mutants, the bacteria should be administered in an amount that is effective to improve body composition and/or reduce body fat percentage. In embodiments in which the compositions are being administered to improve body composition and/or reduce body fat percentage, the compositions should be administered at effective total daily doses of from about $1 \cdot 10^3$ CFU *Bacillus subtilis* DE111 to about $1 \cdot 10^{15}$ CFU *Bacillus subtilis* DE111. In other embodiments in which the compositions are being administered to improve body composition and/or reduce body fat percentage, the compositions should be administered at effective total daily doses of from about $1 \cdot 10^4$ CFU *Bacillus subtilis* DE111 to about $1 \cdot 10^{14}$ CFU *Bacillus subtilis* DE111. In yet other embodiments in which the compositions are being administered to improve body composition and/or reduce body fat percentage, the compositions should be administered at effective total daily doses of from about $1 \cdot 10^5$ CFU *Bacillus subtilis* DE111 to about $1 \cdot 10^{13}$ CFU *Bacillus subtilis* DE111. In yet other embodiments in which the compositions are being administered to improve body composition and/or reduce body fat percentage, the compositions should be administered at effective total daily doses of from about $1 \cdot 10^6$ CFU *Bacillus subtilis* DE111 to about $1 \cdot 10^{12}$ CFU *Bacillus subtilis* DE111. In yet other embodiments in which the compositions are being administered to improve body composition and/or reduce body fat percentage, the compositions should be administered at effective total daily doses of from about $1 \cdot 10^8$ CFU *Bacillus subtilis* DE111 to about $1 \cdot 10^{11}$ CFU *Bacillus subtilis* DE11. In yet other embodiments, a preferred effective total daily dose range is from about $1 \cdot 10^9$ CFU *Bacillus subtilis* DE111 to about $1 \cdot 10^{11}$ CFU *Bacillus subtilis* DE111. In yet another embodiment, *Bacillus subtilis* DE111 can be provided in a daily dose of about $5 \cdot 10^9$ CFU for several weeks, up to a total of about 10 weeks.

In an embodiment, administration of a *Bacillus subtilis* DE111 dose at about 5 billion CFU per day statistically improved body composition and/or statistically reduced body fat percentage of an individual. In contrast, the testing group administered placebo composition did not generate similar improvements.

In certain embodiments, the compositions administered according to the methods of the present disclosure may also include one or more excipients, most preferably one or more nutraceutical or pharmaceutical excipients. Compositions containing one or more excipients and incorporating one or more probiotics can be prepared by procedures known in the art. Optionally, compositions can include one or more adjuvants, excipients, carriers, buffers, diluents, and/or other customary pharmaceutical auxiliaries. For example, probiotics can be formulated into tablets, capsules, powders, suspensions, solutions for oral administration, solutions for parenteral administration including intravenous, intradermal, intramuscular, and subcutaneous administration, and solutions for application onto patches for transdermal application with common and conventional barriers, binders, diluents, and excipients.

In certain embodiments, nutraceutical compositions administered according to the methods of the present disclosure may be administered in combination with a pharmaceutically acceptable carrier. In certain embodiments, the active ingredients in such formulations may comprise from about 1% by weight to about 99% by weight. In other embodiments, the active ingredients in such formulations may comprise from about 0.1% by weight to about 99.9% by weight. "Pharmaceutically acceptable carrier" means any carrier, diluent, or excipient that is compatible with the other ingredients of the formulation and not deleterious to the user. Useful excipients include, but are not limited to, microcrystalline cellulose, magnesium stearate, calcium stearate, any acceptable sugar (e.g., mannitol, xylitol), and the like, and for cosmetic use, an oil-base is preferred.

Methods of Improving Body Composition and/or Reducing Body Fat Percentage

In an embodiment, a method of improving body composition in an individual can include the steps of:
(a) administering orally to the individual a composition comprising *Bacillus subtilis* in a dose of from about $1 \cdot 10^8$ CFU per day to about $1 \cdot 10^{11}$ CFU per day for at least 70 days;
wherein the body fat percentage of the individual is reduced.

The method described herein effects an improvement of body composition in an individual.

In another embodiment, a method of improving body composition in an individual can include the steps of:
(a) administering orally to the individual a composition comprising *Bacillus subtilis* in an in a dose of from about $1 \cdot 10^8$ CFU per day to about $1 \cdot 10^{11}$ CFU per day for at least 90 days;
wherein the body fat percentage of the individual is reduced.

The method described herein effects an improvement of body composition in an individual.

In yet another embodiment, a method of improving body composition in an individual can include the steps of:
(a) administering orally to the individual a composition comprising *Bacillus subtilis* in a dose of from about $1 \cdot 10^9$ CFU per day to about $1 \cdot 10^{10}$ CFU per day for at least 70 days;
wherein the body fat percentage of the individual is reduced.

The method described herein effects an improvement of body composition in an individual.

In yet another embodiment, a method of improving body composition in an individual can include the steps of:
(a) administering orally to the individual a composition comprising *Bacillus subtilis* in a dose of from about $1 \cdot 10^9$ CFU per day to about $1 \cdot 10^{10}$ CFU per day for at least 90 days;
wherein the body fat percentage of the individual is reduced.

The method described herein effects an improvement of body composition in an individual.

In yet another embodiment, a method of improving body composition in an individual can include the steps of:
(a) administering orally to the individual a composition comprising *Bacillus subtilis* in a dose of about $5 \cdot 10^9$ CFU per day for at least 70 days;
wherein the body fat percentage of the individual is reduced.

The method described herein effects an improvement of body composition in an individual.

In yet another embodiment, a method of improving body composition in an individual can include the steps of:
(a) administering orally to the individual a composition comprising *Bacillus subtilis* in a dose of about $5 \cdot 10^9$ CFU per day for at least 90 days;
wherein the body fat percentage of the individual is reduced.

The method described herein effects an improvement of body composition in an individual.

In yet another embodiment, a method of improving body composition in an individual can include the steps of:
(a) administering orally to the individual a composition comprising *Bacillus subtilis* in a dose of from about $1 \cdot 10^8$ CFU per day to about $1 \cdot 10^{11}$ CFU per day for at least 70 days;
wherein the body fat percentage of the individual is reduced by at least 1%.

The method described herein effects an improvement of body composition in an individual.

In yet another embodiment, a method of improving body composition in an individual can include the steps of:
(a) administering orally to the individual a composition comprising *Bacillus subtilis* in a dose of from about $1 \cdot 10^8$ CFU per day to about $1 \cdot 10^{11}$ CFU per day for at least 90 days;

wherein the body fat percentage of the individual is reduced by at least 1%.

The method described herein effects an improvement of body composition in an individual.

In yet another embodiment, a method of improving body composition in an individual can include the steps of:
(a) administering orally to the individual a composition comprising *Bacillus subtilis* in a dose of from about $1·10^9$ CFU per day to about $1·10^{10}$ CFU per day for at least 70 days;
wherein the body fat percentage of the individual is reduced by at least 1%.

The method described herein effects an improvement of body composition in an individual.

In yet another embodiment, a method of improving body composition in an individual can include the steps of:
(a) administering orally to the individual a composition comprising *Bacillus subtilis* in a dose of from about $1·10^9$ CFU per day to about $1·10^{10}$ CFU per day for at least 90 days;
wherein the body fat percentage of the individual is reduced by at least 1%.

The method described herein effects an improvement of body composition in an individual.

In yet another embodiment, a method of improving body composition in an individual can include the steps of:
(a) administering orally to the individual a composition comprising *Bacillus subtilis* in a dose of about $5·10^9$ CFU per day for at least 70 days;
wherein the body fat percentage of the individual is reduced by at least 1%.

The method described herein effects an improvement of body composition in an individual.

In yet another embodiment, a method of improving body composition in an individual can include the steps of:
(a) administering orally to the individual a composition comprising *Bacillus subtilis* in a dose of about $5·10^9$ CFU per day for at least 90 days;
wherein the body fat percentage of the individual is reduced by at least 1%.

The method described herein effects an improvement of body composition in an individual.

In yet another embodiment, a method of improving body composition in an individual can include the steps of:
(a) administering orally to the individual a composition comprising *Bacillus subtilis* in a dose of from about $1·10^8$ CFU per day to about $1·10^{11}$ CFU per day for at least 70 days;
wherein the body fat percentage of the individual is reduced by at least 2%.

The method described herein effects an improvement of body composition in an individual.

In yet another embodiment, a method of improving body composition in an individual can include the steps of:
(a) administering orally to the individual a composition comprising *Bacillus subtilis* in a dose of from about $1·10^8$ CFU per day to about $1·10^{11}$ CFU per day for at least 90 days;
wherein the body fat percentage of the individual is reduced by at least 2%.

The method described herein effects an improvement of body composition in an individual.

In yet another embodiment, a method of improving body composition in an individual can include the steps of:
(a) administering orally to the individual a composition comprising *Bacillus subtilis* in a dose of from about $1·10^9$ CFU per day to about $1·10^{10}$ CFU per day for at least 70 days;
wherein the body fat percentage of the individual is reduced by at least 2%.

The method described herein effects an improvement of body composition in an individual.

In yet another embodiment, a method of improving body composition in an individual can include the steps of:
(a) administering orally to the individual a composition comprising *Bacillus subtilis* in a dose of from about $1·10^9$ CFU per day to about $1·10^{10}$ CFU per day for at least 90 days;
wherein the body fat percentage of the individual is reduced by at least 2%.

The method described herein effects an improvement of body composition in an individual.

In yet another embodiment, a method of improving body composition in an individual can include the steps of:
(a) administering orally to the individual a composition comprising *Bacillus subtilis* in a dose of about $5·10^9$ CFU per day for at least 70 days;
wherein the body fat percentage of the individual is reduced by at least 2%.

The method described herein effects an improvement of body composition in an individual.

In yet another embodiment, a method of improving body composition in an individual can include the steps of:
(a) administering orally to the individual a composition comprising *Bacillus subtilis* in a dose of about $5·10^9$ CFU per day for at least 90 days;
wherein the body fat percentage of the individual is reduced by at least 2%.

The method described herein effects an improvement of body composition in an individual.

In yet another embodiment, a method of improving body composition in an individual can include the steps of:
(a) administering orally to the individual a composition comprising *Bacillus subtilis* in a dose of from about $1·10^8$ CFU per day to about $1·10^{11}$ CFU per day for at least 70 days; and
(b) submitting the individual to a resistance training program 3 days per week throughout the entire at least 70 days;
wherein the body fat percentage of the individual is reduced.

The method described herein effects an improvement of body composition in an individual.

In yet another embodiment, a method of improving body composition in an individual can include the steps of:
(a) administering orally to the individual a composition comprising *Bacillus subtilis* in a dose of from about $1·10^8$ CFU per day to about $1·10^{11}$ CFU per day for at least 90 days; and
(b) submitting the individual to a resistance training program 3 days per week throughout the entire at least 90 days;
wherein the body fat percentage of the individual is reduced.

The method described herein effects an improvement of body composition in an individual.

In yet another embodiment, a method of improving body composition in an individual can include the steps of:

(a) administering orally to the individual a composition comprising *Bacillus subtilis* in a dose of from about $1 \cdot 10^9$ CFU per day to about $1 \cdot 10^{10}$ CFU per day for at least 70 days; and (b) submitting the individual to a resistance training program 3 days per week throughout the entire at least 70 days;

wherein the body fat percentage of the individual is reduced.

The method described herein effects an improvement of body composition in an individual.

In yet another embodiment, a method of improving body composition in an individual can include the steps of:

(a) administering orally to the individual a composition comprising *Bacillus subtilis* in a dose of from about $1 \cdot 10^9$ CFU per day to about $1 \cdot 10^{10}$ CFU per day for at least 90 days; and (b) submitting the individual to a resistance training program 3 days per week throughout the entire at least 90 days;

wherein the body fat percentage of the individual is reduced.

The method described herein effects an improvement of body composition in an individual.

In yet another embodiment, a method of improving body composition in an individual can include the steps of:

(a) administering orally to the individual a composition comprising *Bacillus subtilis* in a dose of about $5 \cdot 10^9$ CFU per day for at least 70 days; and (b) submitting the individual to a resistance training program 3 days per week throughout the entire at least 70 days;

wherein the body fat percentage of the individual is reduced.

The method described herein effects an improvement of body composition in an individual.

In yet another embodiment, a method of improving body composition in an individual can include the steps of:

(a) administering orally to the individual a composition comprising *Bacillus subtilis* in a dose of about $5 \cdot 10^9$ CFU per day for at least 90 days; and (b) submitting the individual to a resistance training program 3 days per week throughout the entire at least 90 days;

wherein the body fat percentage of the individual is reduced.

The method described herein effects an improvement of body composition in an individual.

In yet another embodiment, a method of improving body composition in an individual can include the steps of:

(a) administering orally to the individual a composition comprising *Bacillus subtilis* in a dose of from about $1 \cdot 10^8$ CFU per day to about $1 \cdot 10^{11}$ CFU per day for at least 70 days; and (b) submitting the individual to a resistance training program 3 days per week throughout the entire at least 70 days;

wherein the body fat percentage of the individual is reduced by at least 1%.

The method described herein effects an improvement of body composition in an individual.

In yet another embodiment, a method of improving body composition in an individual can include the steps of:

(a) administering orally to the individual a composition comprising *Bacillus subtilis* in a dose of from about $1 \cdot 10^8$ CFU per day to about $1 \cdot 10^{11}$ CFU per day for at least 90 days; and (b) submitting the individual to a resistance training program 3 days per week throughout the entire at least 90 days;

wherein the body fat percentage of the individual is reduced by at least 1%.

The method described herein effects an improvement of body composition in an individual.

In yet another embodiment, a method of improving body composition in an individual can include the steps of:

(a) administering orally to the individual a composition comprising *Bacillus subtilis* in a dose of from about $1 \cdot 10^9$ CFU per day to about $1 \cdot 10^{10}$ CFU per day for at least 70 days; and (b) submitting the individual to a resistance training program 3 days per week throughout the entire at least 70 days;

wherein the body fat percentage of the individual is reduced by at least 1%.

The method described herein effects an improvement of body composition in an individual.

In yet another embodiment, a method of improving body composition in an individual can include the steps of:

(a) administering orally to the individual a composition comprising *Bacillus subtilis* in a dose of from about $1 \cdot 10^9$ CFU per day to about $1 \cdot 10^{10}$ CFU per day for at least 90 days; and (b) submitting the individual to a resistance training program 3 days per week throughout the entire at least 90 days;

wherein the body fat percentage of the individual is reduced by at least 1%.

The method described herein effects an improvement of body composition in an individual.

In yet another embodiment, a method of improving body composition in an individual can include the steps of:

(a) administering orally to the individual a composition comprising *Bacillus subtilis* in a dose of about $5 \cdot 10^9$ CFU per day for at least 70 days; and (b) submitting the individual to a resistance training program 3 days per week throughout the entire at least 70 days;

wherein the body fat percentage of the individual is reduced by at least 1%.

The method described herein effects an improvement of body composition in an individual.

In yet another embodiment, a method of improving body composition in an individual can include the steps of:

(a) administering orally to the individual a composition comprising *Bacillus subtilis* in a dose of about $5 \cdot 10^9$ CFU per day for at least 90 days; and (b) submitting the individual to a resistance training program 3 days per week throughout the entire at least 90 days;

wherein the body fat percentage of the individual is reduced by at least 1%.

The method described herein effects an improvement of body composition in an individual.

In yet another embodiment, a method of improving body composition in an individual can include the steps of:

(a) administering orally to the individual a composition comprising *Bacillus subtilis* in a dose of from about $1 \cdot 10^8$ CFU per day to about $1 \cdot 10^{11}$ CFU per day for at least 70 days; and (b) submitting the individual to a resistance training program 3 days per week throughout the entire at least 70 days;

wherein the body fat percentage of the individual is reduced by at least 2%.

The method described herein effects an improvement of body composition in an individual.

In yet another embodiment, a method of improving body composition in an individual can include the steps of:
  (a) administering orally to the individual a composition comprising *Bacillus subtilis* in a dose of from about $1·10^8$ CFU per day to about $1·10^{11}$ CFU per day for at least 90 days; and
  (b) submitting the individual to a resistance training program 3 days per week throughout the entire at least 90 days;
  wherein the body fat percentage of the individual is reduced by at least 2%.

The method described herein effects an improvement of body composition in an individual.

In yet another embodiment, a method of improving body composition in an individual can include the steps of:
  (a) administering orally to the individual a composition comprising *Bacillus subtilis* in a dose of from about $1·10^9$ CFU per day to about $1·10^{10}$ CFU per day for at least 70 days; and
  (b) submitting the individual to a resistance training program 3 days per week throughout the entire at least 70 days;
  wherein the body fat percentage of the individual is reduced by at least 2%.

The method described herein effects an improvement of body composition in an individual.

In yet another embodiment, a method of improving body composition in an individual can include the steps of:
  (a) administering orally to the individual a composition comprising *Bacillus subtilis* in a dose of from about $1·10^9$ CFU per day to about $1·10^{10}$ CFU per day for at least 90 days; and
  (b) submitting the individual to a resistance training program 3 days per week throughout the entire at least 90 days;
  wherein the body fat percentage of the individual is reduced by at least 2%.

The method described herein effects an improvement of body composition in an individual.

In yet another embodiment, a method of improving body composition in an individual can include the steps of:
  (a) administering orally to the individual a composition comprising *Bacillus subtilis* in a dose of about $5·10^9$ CFU per day for at least 70 days; and
  (b) submitting the individual to a resistance training program 3 days per week throughout the entire at least 70 days;
  wherein the body fat percentage of the individual is reduced by at least 2%.

The method described herein effects an improvement of body composition in an individual.

In yet another embodiment, a method of improving body composition in an individual can include the steps of:
  (a) administering orally to the individual a composition comprising *Bacillus subtilis* in a dose of about $5·10^9$ CFU per day for at least 90 days; and
  (b) submitting the individual to a resistance training program 3 days per week throughout the entire at least 90 days;
  wherein the body fat percentage of the individual is reduced by at least 2%.

The method described herein effects an improvement of body composition in an individual.

In yet another embodiment, a method of improving body composition in an individual can include the steps of:
  (a) administering orally to the individual a composition comprising *Bacillus subtilis* in a dose of from about $1·10^8$ CFU per day to about $1·10^{11}$ CFU per day for at least 70 days; and
  (b) submitting the individual to a conditioning training program 3 days per week throughout the entire at least 70 days;
  wherein the body fat percentage of the individual is reduced.

The method described herein effects an improvement of body composition in an individual.

In yet another embodiment, a method of improving body composition in an individual can include the steps of:
  (a) administering orally to the individual a composition comprising *Bacillus subtilis* in a dose of from about $1·10^8$ CFU per day to about $1·10^{11}$ CFU per day for at least 90 days; and
  (b) submitting the individual to a conditioning training program 3 days per week throughout the entire at least 90 days;
  wherein the body fat percentage of the individual is reduced.

The method described herein effects an improvement of body composition in an individual.

In yet another embodiment, a method of improving body composition in an individual can include the steps of:
  (a) administering orally to the individual a composition comprising *Bacillus subtilis* in a dose of from about $1·10^9$ CFU per day to about $1·10^{10}$ CFU per day for at least 70 days; and
  (b) submitting the individual to a conditioning training program 3 days per week throughout the entire at least 70 days;
  wherein the body fat percentage of the individual is reduced.

The method described herein effects an improvement of body composition in an individual.

In yet another embodiment, a method of improving body composition in an individual can include the steps of:
  (a) administering orally to the individual a composition comprising *Bacillus subtilis* in a dose of from about $1·10^9$ CFU per day to about $1·10^{10}$ CFU per day for at least 90 days; and
  (b) submitting the individual to a conditioning training program 3 days per week throughout the entire at least 90 days;
  wherein the body fat percentage of the individual is reduced.

The method described herein effects an improvement of body composition in an individual.

In yet another embodiment, a method of improving body composition in an individual can include the steps of:
  (a) administering orally to the individual a composition comprising *Bacillus subtilis* in a dose of about $5·10^9$ CFU per day for at least 70 days; and
  (b) submitting the individual to a conditioning training program 3 days per week throughout the entire at least 70 days;
  wherein the body fat percentage of the individual is reduced.

The method described herein effects an improvement of body composition in an individual.

In yet another embodiment, a method of improving body composition in an individual can include the steps of:

(a) administering orally to the individual a composition comprising *Bacillus subtilis* in a dose of about $5 \cdot 10^9$ CFU per day for at least 90 days; and
(b) submitting the individual to a conditioning training program 3 days per week throughout the entire at least 90 days;
wherein the body fat percentage of the individual is reduced.

The method described herein effects an improvement of body composition in an individual.

In yet another embodiment, a method of improving body composition in an individual can include the steps of:
(a) administering orally to the individual a composition comprising *Bacillus subtilis* in a dose of from about $1 \cdot 10^8$ CFU per day to about $1 \cdot 10^{11}$ CFU per day for at least 70 days; and
(b) submitting the individual to a conditioning training program 3 days per week throughout the entire at least 70 days;
wherein the body fat percentage of the individual is reduced by at least 1%.

The method described herein effects an improvement of body composition in an individual.

In yet another embodiment, a method of improving body composition in an individual can include the steps of:
(a) administering orally to the individual a composition comprising *Bacillus subtilis* in a dose of from about $1 \cdot 10^8$ CFU per day to about $1 \cdot 10^{11}$ CFU per day for at least 90 days; and
(b) submitting the individual to a conditioning training program 3 days per week throughout the entire at least 90 days;
wherein the body fat percentage of the individual is reduced by at least 1%.

The method described herein effects an improvement of body composition in an individual.

In yet another embodiment, a method of improving body composition in an individual can include the steps of:
(a) administering orally to the individual a composition comprising *Bacillus subtilis* in a dose of from about $1 \cdot 10^9$ CFU per day to about $1 \cdot 10^{10}$ CFU per day for at least 70 days; and
(b) submitting the individual to a conditioning training program 3 days per week throughout the entire at least 70 days;
wherein the body fat percentage of the individual is reduced by at least 1%.

The method described herein effects an improvement of body composition in an individual.

In yet another embodiment, a method of improving body composition in an individual can include the steps of:
(a) administering orally to the individual a composition comprising *Bacillus subtilis* in a dose of from about $1 \cdot 10^9$ CFU per day to about $1 \cdot 10^{10}$ CFU per day for at least 90 days; and
(b) submitting the individual to a conditioning training program 3 days per week throughout the entire at least 90 days;
wherein the body fat percentage of the individual is reduced by at least 1%.

The method described herein effects an improvement of body composition in an individual.

In yet another embodiment, a method of improving body composition in an individual can include the steps of:
(a) administering orally to the individual a composition comprising *Bacillus subtilis* in a dose of about $5 \cdot 10^9$ CFU per day for at least 70 days; and
(b) submitting the individual to a conditioning training program 3 days per week throughout the entire at least 70 days;
wherein the body fat percentage of the individual is reduced by at least 1%.

The method described herein effects an improvement of body composition in an individual.

In yet another embodiment, a method of improving body composition in an individual can include the steps of:
(a) administering orally to the individual a composition comprising *Bacillus subtilis* in a dose of about $5 \cdot 10^9$ CFU per day for at least 90 days; and
(b) submitting the individual to a conditioning training program 3 days per week throughout the entire at least 90 days;
wherein the body fat percentage of the individual is reduced by at least 1%.

The method described herein effects an improvement of body composition in an individual.

In yet another embodiment, a method of improving body composition in an individual can include the steps of:
(a) administering orally to the individual a composition comprising *Bacillus subtilis* in a dose of from about $1 \cdot 10^8$ CFU per day to about $1 \cdot 10^{11}$ CFU per day for at least 70 days; and
(b) submitting the individual to a conditioning training program 3 days per week throughout the entire at least 70 days;
wherein the body fat percentage of the individual is reduced by at least 2%.

The method described herein effects an improvement of body composition in an individual.

In yet another embodiment, a method of improving body composition in an individual can include the steps of:
(a) administering orally to the individual a composition comprising *Bacillus subtilis* in a dose of from about $1 \cdot 10^8$ CFU per day to about $1 \cdot 10^{11}$ CFU per day for at least 90 days; and
(b) submitting the individual to a conditioning training program 3 days per week throughout the entire at least 90 days;
wherein the body fat percentage of the individual is reduced by at least 2%.

The method described herein effects an improvement of body composition in an individual.

In yet another embodiment, a method of improving body composition in an individual can include the steps of:
(a) administering orally to the individual a composition comprising *Bacillus subtilis* in a dose of from about $1 \cdot 10^9$ CFU per day to about $1 \cdot 10^{10}$ CFU per day for at least 70 days; and
(b) submitting the individual to a conditioning training program 3 days per week throughout the entire at least 70 days;
wherein the body fat percentage of the individual is reduced by at least 2%.

The method described herein effects an improvement of body composition in an individual.

In yet another embodiment, a method of improving body composition in an individual can include the steps of:
(a) administering orally to the individual a composition comprising *Bacillus subtilis* in a dose of from about $1 \cdot 10^9$ CFU per day to about $1 \cdot 10^{10}$ CFU per day for at least 90 days; and
(b) submitting the individual to a conditioning training program 3 days per week throughout the entire at least 90 days;

wherein the body fat percentage of the individual is reduced by at least 2%.

The method described herein effects an improvement of body composition in an individual.

In yet another embodiment, a method of improving body composition in an individual can include the steps of:
(a) administering orally to the individual a composition comprising *Bacillus subtilis* in a dose of about $5 \cdot 10^9$ CFU per day for at least 70 days; and
(b) submitting the individual to a conditioning training program 3 days per week throughout the entire at least 70 days;
wherein the body fat percentage of the individual is reduced by at least 2%.

The method described herein effects an improvement of body composition in an individual.

In yet another embodiment, a method of improving body composition in an individual can include the steps of:
(a) administering orally to the individual a composition comprising *Bacillus subtilis* in a dose of about $5 \cdot 10^9$ CFU per day for at least 90 days; and
(b) submitting the individual to a conditioning training program 3 days per week throughout the entire at least 90 days;
wherein the body fat percentage of the individual is reduced by at least 2%.

The method described herein effects an improvement of body composition in an individual.

In yet another embodiment, a method of improving body composition in an individual can include the steps of:
(a) administering orally to the individual a composition comprising *Bacillus subtilis* in a dose of from about $1 \cdot 10^8$ CFU per day to about $1 \cdot 10^{11}$ CFU per day for at least 70 days;
(b) submitting the individual to a resistance training program 3 days per week throughout the entire at least 70 days; and
(c) submitting the individual to a conditioning training program 3 days per week throughout the entire at least 70 days;
wherein the body fat percentage of the individual is reduced.

The method described herein effects an improvement of body composition in an individual.

In yet another embodiment, a method of improving body composition in an individual can include the steps of:
(a) administering orally to the individual a composition comprising *Bacillus subtilis* in a dose of from about $1 \cdot 10^8$ CFU per day to about $1 \cdot 10^{11}$ CFU per day for at least 90 days;
(b) submitting the individual to a resistance training program 3 days per week throughout the entire at least 90 days; and
(c) submitting the individual to a conditioning training program 3 days per week throughout the entire at least 90 days;
wherein the body fat percentage of the individual is reduced.

The method described herein effects an improvement of body composition in an individual.

In yet another embodiment, a method of improving body composition in an individual can include the steps of:
(a) administering orally to the individual a composition comprising *Bacillus subtilis* in a dose of from about $1 \cdot 10^9$ CFU per day to about $1 \cdot 10^{10}$ CFU per day for at least 70 days;
(b) submitting the individual to a resistance training program 3 days per week throughout the entire at least 70 days; and
(c) submitting the individual to a conditioning training program 3 days per week throughout the entire at least 70 days;
wherein the body fat percentage of the individual is reduced.

The method described herein effects an improvement of body composition in an individual.

In yet another embodiment, a method of improving body composition in an individual can include the steps of:
(a) administering orally to the individual a composition comprising *Bacillus subtilis* in a dose of from about $1 \cdot 10^9$ CFU per day to about $1 \cdot 10^{10}$ CFU per day for at least 90 days;
(b) submitting the individual to a resistance training program 3 days per week throughout the entire at least 90 days; and
(c) submitting the individual to a conditioning training program 3 days per week throughout the entire at least 90 days;
wherein the body fat percentage of the individual is reduced.

The method described herein effects an improvement of body composition in an individual.

In yet another embodiment, a method of improving body composition in an individual can include the steps of:
(a) administering orally to the individual a composition comprising *Bacillus subtilis* in a dose of about $5 \cdot 10^9$ CFU per day for at least 70 days;
(b) submitting the individual to a resistance training program 3 days per week throughout the entire at least 70 days; and
(c) submitting the individual to a conditioning training program 3 days per week throughout the entire at least 70 days;
wherein the body fat percentage of the individual is reduced.

The method described herein effects an improvement of body composition in an individual.

In yet another embodiment, a method of improving body composition in an individual can include the steps of:
(a) administering orally to the individual a composition comprising *Bacillus subtilis* in a dose of about $5 \cdot 10^9$ CFU per day for at least 90 days;
(b) submitting the individual to a resistance training program 3 days per week throughout the entire at least 90 days; and
(c) submitting the individual to a conditioning training program 3 days per week throughout the entire at least 90 days;
wherein the body fat percentage of the individual is reduced.

The method described herein effects an improvement of body composition in an individual.

In yet another embodiment, a method of improving body composition in an individual can include the steps of:
(a) administering orally to the individual a composition comprising *Bacillus subtilis* in a dose of from about $1 \cdot 10^8$ CFU per day to about $1 \cdot 10^{11}$ CFU per day for at least 70 days;
(b) submitting the individual to a resistance training program 3 days per week throughout the entire at least 70 days; and (c) submitting the individual to a conditioning training program 3 days per week throughout the entire at least 70 days;

wherein the body fat percentage of the individual is reduced by at least 1%.

The method described herein effects an improvement of body composition in an individual.

In yet another embodiment, a method of improving body composition in an individual can include the steps of:
  (a) administering orally to the individual a composition comprising *Bacillus subtilis* in a dose of from about $1 \cdot 10^8$ CFU per day to about $1 \cdot 10^{11}$ CFU per day for at least 90 days;
  (b) submitting the individual to a resistance training program 3 days per week throughout the entire at least 90 days; and
  (c) submitting the individual to a conditioning training program 3 days per week throughout the entire at least 90 days;
  wherein the body fat percentage of the individual is reduced by at least 1%.

The method described herein effects an improvement of body composition in an individual.

In yet another embodiment, a method of improving body composition in an individual can include the steps of:
  (a) administering orally to the individual a composition comprising *Bacillus subtilis* in a dose of from about $1 \cdot 10^9$ CFU per day to about $1 \cdot 10^{10}$ CFU per day for at least 70 days;
  (b) submitting the individual to a resistance training program 3 days per week throughout the entire at least 70 days; and
  (c) submitting the individual to a conditioning training program 3 days per week throughout the entire at least 70 days;
  wherein the body fat percentage of the individual is reduced by at least 1%.

The method described herein effects an improvement of body composition in an individual.

In yet another embodiment, a method of improving body composition in an individual can include the steps of:
  (a) administering orally to the individual a composition comprising *Bacillus subtilis* in a dose of from about $1 \cdot 10^9$ CFU per day to about $1 \cdot 10^{10}$ CFU per day for at least 90 days;
  (b) submitting the individual to a resistance training program 3 days per week throughout the entire at least 90 days; and
  (c) submitting the individual to a conditioning training program 3 days per week throughout the entire at least 90 days;
  wherein the body fat percentage of the individual is reduced by at least 1%.

The method described herein effects an improvement of body composition in an individual.

In yet another embodiment, a method of improving body composition in an individual can include the steps of:
  (a) administering orally to the individual a composition comprising *Bacillus subtilis* in a dose of about $5 \cdot 10^9$ CFU per day for at least 70 days;
  (b) submitting the individual to a resistance training program 3 days per week throughout the entire at least 70 days; and
  (c) submitting the individual to a conditioning training program 3 days per week throughout the entire at least 70 days;
  wherein the body fat percentage of the individual is reduced by at least 1%.

The method described herein effects an improvement of body composition in an individual.

In yet another embodiment, a method of improving body composition in an individual can include the steps of:
  (a) administering orally to the individual a composition comprising *Bacillus subtilis* in a dose of about $5 \cdot 10^9$ CFU per day for at least 90 days;
  (b) submitting the individual to a resistance training program 3 days per week throughout the entire at least 90 days; and
  (c) submitting the individual to a conditioning training program 3 days per week throughout the entire at least 90 days;
  wherein the body fat percentage of the individual is reduced by at least 1%.

The method described herein effects an improvement of body composition in an individual.

In yet another embodiment, a method of improving body composition in an individual can include the steps of:
  (a) administering orally to the individual a composition comprising *Bacillus subtilis* in a dose of from about $1 \cdot 10^8$ CFU per day to about $1 \cdot 10^{11}$ CFU per day for at least 70 days;
  (b) submitting the individual to a resistance training program 3 days per week throughout the entire at least 70 days; and
  (c) submitting the individual to a conditioning training program 3 days per week throughout the entire at least 70 days;
  wherein the body fat percentage of the individual is reduced by at least 2%.

The method described herein effects an improvement of body composition in an individual.

In yet another embodiment, a method of improving body composition in an individual can include the steps of:
  (a) administering orally to the individual a composition comprising *Bacillus subtilis* in a dose of from about $1 \cdot 10^8$ CFU per day to about $1 \cdot 10^{11}$ CFU per day for at least 90 days;
  (b) submitting the individual to a resistance training program 3 days per week throughout the entire at least 90 days; and
  (c) submitting the individual to a conditioning training program 3 days per week throughout the entire at least 90 days;
  wherein the body fat percentage of the individual is reduced by at least 2%.

The method described herein effects an improvement of body composition in an individual.

In yet another embodiment, a method of improving body composition in an individual can include the steps of:
  (a) administering orally to the individual a composition comprising *Bacillus subtilis* in a dose of from about $1 \cdot 10^9$ CFU per day to about $1 \cdot 10^{10}$ CFU per day for at least 70 days;
  (b) submitting the individual to a resistance training program 3 days per week throughout the entire at least 70 days; and
  (c) submitting the individual to a conditioning training program 3 days per week throughout the entire at least 70 days;
  wherein the body fat percentage of the individual is reduced by at least 2%.

The method described herein effects an improvement of body composition in an individual.

In yet another embodiment, a method of improving body composition in an individual can include the steps of:
(a) administering orally to the individual a composition comprising *Bacillus subtilis* in a dose of from about $1·10^9$ CFU per day to about $1·10^{10}$ CFU per day for at least 90 days;
(b) submitting the individual to a resistance training program 3 days per week throughout the entire at least 90 days; and
(c) submitting the individual to a conditioning training program 3 days per week throughout the entire at least 90 days;
wherein the body fat percentage of the individual is reduced by at least 2%.

The method described herein effects an improvement of body composition in an individual.

In yet another embodiment, a method of improving body composition in an individual can include the steps of:
(a) administering orally to the individual a composition comprising *Bacillus subtilis* in a dose of about $5·10^9$ CFU per day for at least 70 days;
(b) submitting the individual to a resistance training program 3 days per week throughout the entire at least 70 days; and
(c) submitting the individual to a conditioning training program 3 days per week throughout the entire at least 70 days;
wherein the body fat percentage of the individual is reduced by at least 2%.

The method described herein effects an improvement of body composition in an individual.

In yet another embodiment, a method of improving body composition in an individual can include the steps of:
(a) administering orally to the individual a composition comprising *Bacillus subtilis* in a dose of about $5·10^9$ CFU per day for at least 90 days;
(b) submitting the individual to a resistance training program 3 days per week throughout the entire at least 90 days; and
(c) submitting the individual to a conditioning training program 3 days per week throughout the entire at least 90 days;
wherein the body fat percentage of the individual is reduced by at least 2%.

The method described herein effects an improvement of body composition in an individual.

In an embodiment, a method of reducing body fat percentage in an individual can include the steps of:
(a) administering orally to the individual a composition comprising *Bacillus subtilis* in a dose of from about $1·10^8$ CFU per day to about $1·10^{11}$ CFU per day for at least 70 days;
wherein the body fat percentage of the individual is reduced.

The method described herein effects a reduction of body fat percentage in an individual.

In another embodiment, a method of reducing body fat percentage in an individual can include the steps of:
(a) administering orally to the individual a composition comprising *Bacillus subtilis* in a dose of from about $1·10^8$ CFU per day to about $1·10^{11}$ CFU per day for at least 90 days;
wherein the body fat percentage of the individual is reduced.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1·10^9$ CFU per day to about $1·10^{10}$ CFU per day for at least 70 days;
wherein the body fat percentage of the individual is reduced.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1·10^9$ CFU per day to about $1·10^{10}$ CFU per day for at least 90 days;
wherein the body fat percentage of the individual is reduced.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of about $5·10^9$ CFU per day for at least 70 days;
wherein the body fat percentage of the individual is reduced.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of about $5·10^9$ CFU per day for at least 90 days;
wherein the body fat percentage of the individual is reduced.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1·10^8$ CFU per day to about $1·10^{11}$ CFU per day for at least 70 days;
wherein the body fat percentage of the individual is reduced by at least 1%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1·10^8$ CFU per day to about $1·10^{11}$ CFU per day for at least 90 days;
wherein the body fat percentage of the individual is reduced by at least 1%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1·10^9$ CFU per day to about $1·10^{10}$ CFU per day for at least 70 days;
wherein the body fat percentage of the individual is reduced by at least 1%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1·10^9$ CFU per day to about $1·10^{10}$ CFU per day for at least 90 days;
wherein the body fat percentage of the individual is reduced by at least 1%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of about $5·10^9$ CFU per day for at least 70 days;
wherein the body fat percentage of the individual is reduced by at least 1%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of about $5·10^9$ CFU per day for at least 90 days;
wherein the body fat percentage of the individual is reduced by at least 1%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1·10^8$ CFU per day to about $1·10^{11}$ CFU per day for at least 70 days;
wherein the body fat percentage of the individual is reduced by at least 2%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1·10^8$ CFU per day to about $1·10^{11}$ CFU per day for at least 90 days;
wherein the body fat percentage of the individual is reduced by at least 2%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1·10^9$ CFU per day to about $1·10^{10}$ CFU per day for at least 70 days;
wherein the body fat percentage of the individual is reduced by at least 2%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1·10^9$ CFU per day to about $1·10^{10}$ CFU per day for at least 90 days;
wherein the body fat percentage of the individual is reduced by at least 2%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of about $5·10^9$ CFU per day for at least 70 days;
wherein the body fat percentage of the individual is reduced by at least 2%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of about $5·10^9$ CFU per day for at least 90 days;
wherein the body fat percentage of the individual is reduced by at least 2%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1·10^8$ CFU per day to about $1·10^{11}$ CFU per day for at least 70 days; and
(b) submitting the individual to a resistance training program 3 days per week throughout the entire at least 70 days;
wherein the body fat percentage of the individual is reduced.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1·10^8$ CFU per day to about $1·10^{11}$ CFU per day for at least 90 days; and
(b) submitting the individual to a resistance training program 3 days per week throughout the entire at least 90 days;
wherein the body fat percentage of the individual is reduced.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1·10^9$ CFU per day to about $1·10^{10}$ CFU per day for at least 70 days; and
(b) submitting the individual to a resistance training program 3 days per week throughout the entire at least 70 days;
wherein the body fat percentage of the individual is reduced.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1·10^9$ CFU per day to about $1·10^{10}$ CFU per day for at least 90 days; and (b) submitting the individual to a resistance training program 3 days per week throughout the entire at least 90 days;

wherein the body fat percentage of the individual is reduced.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of about 5·10$^9$ CFU per day for at least 70 days; and
(b) submitting the individual to a resistance training program 3 days per week throughout the entire at least 70 days;

wherein the body fat percentage of the individual is reduced.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of about 5·10$^9$ CFU per day for at least 90 days; and
(b) submitting the individual to a resistance training program 3 days per week throughout the entire at least 90 days;

wherein the body fat percentage of the individual is reduced.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about 1·10$^8$ CFU per day to about 1·10$^{11}$ CFU per day for at least 70 days; and
(b) submitting the individual to a resistance training program 3 days per week throughout the entire at least 70 days;

wherein the body fat percentage of the individual is reduced by at least 1%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about 1·10$^8$ CFU per day to about 1·10$^{11}$ CFU per day for at least 90 days; and
(b) submitting the individual to a resistance training program 3 days per week throughout the entire at least 90 days;

wherein the body fat percentage of the individual is reduced by at least 1%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about 1·10$^9$ CFU per day to about 1·10$^{10}$ CFU per day for at least 70 days; and
(b) submitting the individual to a resistance training program 3 days per week throughout the entire at least 70 days;

wherein the body fat percentage of the individual is reduced by at least 1%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about 1·10$^9$ CFU per day to about 1·10$^{10}$ CFU per day for at least 90 days; and
(b) submitting the individual to a resistance training program 3 days per week throughout the entire at least 90 days;

wherein the body fat percentage of the individual is reduced by at least 1%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of about 5·10$^9$ CFU per day for at least 70 days; and
(b) submitting the individual to a resistance training program 3 days per week throughout the entire at least 70 days;

wherein the body fat percentage of the individual is reduced by at least 1%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of about 5·10$^9$ CFU per day for at least 90 days; and
(b) submitting the individual to a resistance training program 3 days per week throughout the entire at least 90 days;

wherein the body fat percentage of the individual is reduced by at least 1%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about 1·10$^8$ CFU per day to about 1·10$^{11}$ CFU per day for at least 70 days; and
(b) submitting the individual to a resistance training program 3 days per week throughout the entire at least 70 days;

wherein the body fat percentage of the individual is reduced by at least 2%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about 1·10$^8$ CFU per day to about 1·10$^{11}$ CFU per day for at least 90 days; and
(b) submitting the individual to a resistance training program 3 days per week throughout the entire at least 90 days;

wherein the body fat percentage of the individual is reduced by at least 2%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1 \cdot 10^9$ CFU per day to about $1 \cdot 10^{10}$ CFU per day for at least 70 days; and
(b) submitting the individual to a resistance training program 3 days per week throughout the entire at least 70 days;
wherein the body fat percentage of the individual is reduced by at least 2%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1 \cdot 10^9$ CFU per day to about $1 \cdot 10^{10}$ CFU per day for at least 90 days; and
(b) submitting the individual to a resistance training program 3 days per week throughout the entire at least 90 days;
wherein the body fat percentage of the individual is reduced by at least 2%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of about $5 \cdot 10^9$ CFU per day for at least 70 days; and
(b) submitting the individual to a resistance training program 3 days per week throughout the entire at least 70 days;
wherein the body fat percentage of the individual is reduced by at least 2%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of about $5 \cdot 10^9$ CFU per day for at least 90 days; and
(b) submitting the individual to a resistance training program 3 days per week throughout the entire at least 90 days;
wherein the body fat percentage of the individual is reduced by at least 2%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1 \cdot 10^8$ CFU per day to about $1 \cdot 10^{11}$ CFU per day for at least 70 days; and
(b) submitting the individual to a conditioning training program 3 days per week throughout the entire at least 70 days;
wherein the body fat percentage of the individual is reduced.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1 \cdot 10^8$ CFU per day to about $1 \cdot 10^{11}$ CFU per day for at least 90 days; and
(b) submitting the individual to a conditioning training program 3 days per week throughout the entire at least 90 days;
wherein the body fat percentage of the individual is reduced.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1 \cdot 10^9$ CFU per day to about $1 \cdot 10^{10}$ CFU per day for at least 70 days; and
(b) submitting the individual to a conditioning training program 3 days per week throughout the entire at least 70 days;
wherein the body fat percentage of the individual is reduced.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1 \cdot 10^9$ CFU per day to about $1 \cdot 10^{10}$ CFU per day for at least 90 days; and
(b) submitting the individual to a conditioning training program 3 days per week throughout the entire at least 90 days;
wherein the body fat percentage of the individual is reduced.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of about $5 \cdot 10^9$ CFU per day for at least 70 days; and
(b) submitting the individual to a conditioning training program 3 days per week throughout the entire at least 70 days;
wherein the body fat percentage of the individual is reduced.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of about $5 \cdot 10^9$ CFU per day for at least 90 days; and
(b) submitting the individual to a conditioning training program 3 days per week throughout the entire at least 90 days;
wherein the body fat percentage of the individual is reduced.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1 \cdot 10^8$ CFU per day to about $1 \cdot 10^{11}$ CFU per day for at least 70 days; and (b) submitting the individual to a conditioning training program 3 days per week throughout the entire at least 70 days;

wherein the body fat percentage of the individual is reduced by at least 1%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1·10^8$ CFU per day to about $1·10^{11}$ CFU per day for at least 90 days; and
(b) submitting the individual to a conditioning training program 3 days per week throughout the entire at least 90 days;

wherein the body fat percentage of the individual is reduced by at least 1%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1·10^9$ CFU per day to about $1·10^{10}$ CFU per day for at least 70 days; and
(b) submitting the individual to a conditioning training program 3 days per week throughout the entire at least 70 days;

wherein the body fat percentage of the individual is reduced by at least 1%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1·10^9$ CFU per day to about $1·10^{10}$ CFU per day for at least 90 days; and
(b) submitting the individual to a conditioning training program 3 days per week throughout the entire at least 90 days;

wherein the body fat percentage of the individual is reduced by at least 1%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of about $5·10^9$ CFU per day for at least 70 days; and
(b) submitting the individual to a conditioning training program 3 days per week throughout the entire at least 70 days;

wherein the body fat percentage of the individual is reduced by at least 1%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of about $5·10^9$ CFU per day for at least 90 days; and
(b) submitting the individual to a conditioning training program 3 days per week throughout the entire at least 90 days;

wherein the body fat percentage of the individual is reduced by at least 1%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1·10^8$ CFU per day to about $1·10^{11}$ CFU per day for at least 70 days; and
(b) submitting the individual to a conditioning training program 3 days per week throughout the entire at least 70 days;

wherein the body fat percentage of the individual is reduced by at least 2%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1·10^8$ CFU per day to about $1·10^{11}$ CFU per day for at least 90 days; and
(b) submitting the individual to a conditioning training program 3 days per week throughout the entire at least 90 days;

wherein the body fat percentage of the individual is reduced by at least 2%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1·10^9$ CFU per day to about $1·10^{10}$ CFU per day for at least 70 days; and
(b) submitting the individual to a conditioning training program 3 days per week throughout the entire at least 70 days;

wherein the body fat percentage of the individual is reduced by at least 2%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1·10^9$ CFU per day to about $1·10^{10}$ CFU per day for at least 90 days; and
(b) submitting the individual to a conditioning training program 3 days per week throughout the entire at least 90 days;

wherein the body fat percentage of the individual is reduced by at least 2%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of about $5·10^9$ CFU per day for at least 70 days; and
(b) submitting the individual to a conditioning training program 3 days per week throughout the entire at least 70 days;

wherein the body fat percentage of the individual is reduced by at least 2%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of about $5 \cdot 10^9$ CFU per day for at least 90 days; and
(b) submitting the individual to a conditioning training program 3 days per week throughout the entire at least 90 days;
wherein the body fat percentage of the individual is reduced by at least 2%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1 \cdot 10^8$ CFU per day to about $1 \cdot 10^{11}$ CFU per day for at least 70 days;
(b) submitting the individual to a resistance training program 3 days per week throughout the entire at least 70 days; and
(c) submitting the individual to a conditioning training program 3 days per week throughout the entire at least 70 days;
wherein the body fat percentage of the individual is reduced.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1 \cdot 10^8$ CFU per day to about $1 \cdot 10^{11}$ CFU per day for at least 90 days;
(b) submitting the individual to a resistance training program 3 days per week throughout the entire at least 90 days; and
(c) submitting the individual to a conditioning training program 3 days per week throughout the entire at least 90 days;
wherein the body fat percentage of the individual is reduced.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1 \cdot 10^9$ CFU per day to about $1 \cdot 10^{10}$ CFU per day for at least 70 days;
(b) submitting the individual to a resistance training program 3 days per week throughout the entire at least 70 days; and
(c) submitting the individual to a conditioning training program 3 days per week throughout the entire at least 70 days;
wherein the body fat percentage of the individual is reduced.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1 \cdot 10^9$ CFU per day to about $1 \cdot 10^{10}$ CFU per day for at least 90 days;
(b) submitting the individual to a resistance training program 3 days per week throughout the entire at least 90 days; and
(c) submitting the individual to a conditioning training program 3 days per week throughout the entire at least 90 days;
wherein the body fat percentage of the individual is reduced.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of about $5 \cdot 10^9$ CFU per day for at least 70 days;
(b) submitting the individual to a resistance training program 3 days per week throughout the entire at least 70 days; and
(c) submitting the individual to a conditioning training program 3 days per week throughout the entire at least 70 days;
wherein the body fat percentage of the individual is reduced.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of about $5 \cdot 10^9$ CFU per day for at least 90 days;
(b) submitting the individual to a resistance training program 3 days per week throughout the entire at least 90 days; and
(c) submitting the individual to a conditioning training program 3 days per week throughout the entire at least 90 days;
wherein the body fat percentage of the individual is reduced.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1 \cdot 10^8$ CFU per day to about $1 \cdot 10^{11}$ CFU per day for at least 70 days;
(b) submitting the individual to a resistance training program 3 days per week throughout the entire at least 70 days; and
(c) submitting the individual to a conditioning training program 3 days per week throughout the entire at least 70 days;
wherein the body fat percentage of the individual is reduced by at least 1%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1 \cdot 10^8$ CFU per day to about $1 \cdot 10^{11}$ CFU per day for at least 90 days;

(b) submitting the individual to a resistance training program 3 days per week throughout the entire at least 90 days; and
(c) submitting the individual to a conditioning training program 3 days per week throughout the entire at least 90 days;
wherein the body fat percentage of the individual is reduced by at least 1%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1·10^9$ CFU per day to about $1·10^{10}$ CFU per day for least 70 days;
(b) submitting the individual to a resistance training program 3 days per week throughout the entire at least 70 days; and
(c) submitting the individual to a conditioning training program 3 days per week throughout the entire at least 70 days;
wherein the body fat percentage of the individual is reduced by at least 1%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1·10^9$ CFU per day to about $1·10^{10}$ CFU per day for at least 90 days;
(b) submitting the individual to a resistance training program 3 days per week throughout the entire at least 90 days; and
(c) submitting the individual to a conditioning training program 3 days per week throughout the entire at least 90 days;
wherein the body fat percentage of the individual is reduced by at least 1%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of about $5·10^9$ CFU per day for at least 70 days;
(b) submitting the individual to a resistance training program 3 days per week throughout the entire at least 70 days; and
(c) submitting the individual to a conditioning training program 3 days per week throughout the entire at least 70 days;
wherein the body fat percentage of the individual is reduced by at least 1%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of about $5·10^9$ CFU per day for at least 90 days;
(b) submitting the individual to a resistance training program 3 days per week throughout the entire at least 90 days; and
(c) submitting the individual to a conditioning training program 3 days per week throughout the entire at least 90 days;
wherein the body fat percentage of the individual is reduced by at least 1%.

The method described herein effects a reduction of body fat percentage in an individual.

In yet another embodiment, a method of reducing body fat percentage in an individual can include the steps of:
(a) administering orally to the individual a composition comprising *Bacillus* subtilisin in a dose of from about $1·10^8$ CFU per day to about $1·10^{11}$ CFU per day for at least 70 days;
(b) submitting the individual to a resistance training program 3 days per week throughout the entire at least 70 days; and
(c) submitting the individual to a conditioning training program 3 days per week throughout the entire at least 70 days;
wherein the body fat percentage of the individual is reduced by at least 2%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1·10^8$ CFU per day to about $1·10^{11}$ CFU per day for at least 90 days;
(b) submitting the individual to a resistance training program 3 days per week throughout the entire at least 90 days; and
(c) submitting the individual to a conditioning training program 3 days per week throughout the entire at least 90 days;
wherein the body fat percentage of the individual is reduced by at least 2%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1·10^9$ CFU per day to about $1·10^{10}$ CFU per day for at least 70 days;
(b) submitting the individual to a resistance training program 3 days per week throughout the entire at least 70 days; and
(c) submitting the individual to a conditioning training program 3 days per week throughout the entire at least 70 days;
wherein the body fat percentage of the individual is reduced by at least 2%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of from about $1·10^9$ CFU per day to about $1·10^{10}$ CFU per day for at least 90 days;
(b) submitting the individual to a resistance training program 3 days per week throughout the entire at least 90 days; and
(c) submitting the individual to a conditioning training program 3 days per week throughout the entire at least 90 days;

wherein the body fat percentage of the individual is reduced by at least 2%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of about $5\cdot10^9$ CFU per day for at least 70 days;
(b) submitting the individual to a resistance training program 3 days per week throughout the entire at least 70 days; and
(c) submitting the individual to a conditioning training program 3 days per week throughout the entire at least 70 days;
wherein the body fat percentage of the individual is reduced by at least 2%.

The method described herein effects a reduction of body fat percentage in an individual.

In yet another embodiment, a method of reducing body fat percentage in an individual can include the steps of:
(a) administering orally to the individual a composition comprising *Bacillus subtilis* in a dose of about $5\cdot10^9$ CFU per day for at least 90 days;
(b) submitting the individual to a resistance training program 3 days per week throughout the entire at least 90 days; and
(c) submitting the individual to a conditioning training program 3 days per week throughout the entire at least 90 days;
wherein the body fat percentage of the individual is reduced by at least 2%.

The method described herein effects a reduction of body fat percentage in an individual.

In certain embodiments, as used herein, the term "resistance training program" can refer, unless otherwise stated, alone or in combination with other terms, to a linear periodized resistance training program incorporating upper body and lower body workouts centered on three core lifts (bench press, squats, and dead lifts) common referred to as the "Wendler 5/3/1." This program organizes progressions over 4 week segments (i.e., 1 week of 3 sets of 5 repetitions ("reps") on each core exercise, followed by 1 week of 3 sets of 3 reps, then 1 week of 1×5/3/1 reps). This is followed by a lighter "unloading" week of 3 sets of 5 reps. Accessory lifts followed a higher volume pattern (i.e., 3-4 sets, 8-12 reps).

In certain embodiments, as used herein, the term "conditioning training program" can refer, unless otherwise stated, alone or in combination with other terms, to conditioning, agility, jumping, and sprint exercises, with workouts consisting of approximately 30-40 minutes of sports-specific skill development and conditioning-related work.

In certain embodiments, the compositions comprising *Bacillus subtilis* can include one or more dry carriers selected from the group consisting of trehalose, maltodextrin, rice flour, microcrystalline cellulose, magnesium stearate, inositol, fructooligosaccharide, galactooligosaccharide, dextrose, and the like. In certain embodiments, the dry carrier can be added to the compositions comprising *Bacillus subtilis* in a weight percentage of from about 1% to about 95% by weight of the composition.

In certain embodiments, the compositions comprising *Bacillus subtilis* can include one or more liquid or gel-based carriers, selected from the group consisting of water and physiological salt solutions, urea, alcohols and derivatives thereof (e.g., methanol, ethanol, propanol, butanol), glycols (e.g., ethylene glycol, propylene glycol), and the like; natural or synthetic flavorings and food-quality coloring agents, all compatible with the organism; thickening agents selected from the group consisting of corn starch, guar gum, xanthan gum, and the like; one or more spore germination inhibitors selected from the group consisting of hyper-saline carriers, methylparaben, guargum, polysorbate, preservatives, and the like. In certain embodiments, the one or more liquid or gel-based carrier(s) can be added to the compositions comprising *Bacillus subtilis* in a weight/volume percentage of from about 0.6% to about 95% weight/volume of the composition. In certain embodiments, the natural or synthetic flavoring(s) can be added to the compositions comprising *Bacillus subtilis* in a weight/volume percentage of from about 3.0% to about 10.0% weight/volume of the composition. In certain embodiments, the coloring agent(s) can be added to the compositions comprising *Bacillus subtilis* in a weight/volume percentage of from about 1.0% to about 10.0% weight/volume of the composition. In certain embodiments, the thickening agent(s) can be added to the compositions comprising *Bacillus subtilis* in a weight/volume percentage of about 2% weight/volume of the composition. In certain embodiments, the one or more spore germination inhibitors can be added to the compositions comprising *Bacillus subtilis* in a weight/volume percentage of about 1% weight/volume of the composition.

Delivery System

Suitable dosage forms include tablets, capsules, solutions, suspensions, powders, gums, and confectionaries. Sublingual delivery systems include, but are not limited to, dissolvable tabs under and on the tongue, liquid drops, and beverages. Edible films, hydrophilic polymers, oral dissolvable films, or oral dissolvable strips can be used. Other useful delivery systems comprise oral or nasal sprays or inhalers, and the like.

For oral administration, probiotics may be further combined with one or more solid inactive ingredients for the preparation of tablets, capsules, pills, powders, granules, or other suitable dosage forms. For example, the active agent may be combined with at least one excipient selected from the group consisting of fillers, binders, humectants, distintegrating agents, solution retarders, absorption accelerators, wetting agents, absorbents, and lubricating agents. Other useful excipients include, but are not limited to, magnesium stearate, calcium stearate, mannitol, xylitol, sweeteners, starch, carboxymethylcellulose, microcrystalline cellulose, silica, gelatin, silicon dioxide, and the like.

In certain embodiments, the components of compositions administered according to the methods of the present disclosure, together with one or more conventional adjuvants, carriers, or diluents, may thus be placed into the form of pharmaceutical compositions and unit dosages thereof. Such forms include: solids, and in particular, tablets, filled capsules, powder and pellet forms; liquids, and in particular, aqueous or non-aqueous solutions, suspensions, emulsions, elixirs; and capsules filled with the same; all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The components of the compositions administered according to the methods of the present disclosure can be administered in a wide variety of oral and parenteral dosage forms. It will be obvious to those skilled in the art that the following dosage forms may comprise, in certain embodiments, as the active component, either a chemical compound of the present disclosure or a pharmaceutically acceptable salt of a chemical compound of the present disclosure.

For preparing pharmaceutical compositions to be administered according to the methods of the present disclosure, pharmaceutically acceptable carriers can be either solid or liquid. Solid form preparations include powders, tablets, pills, capsules, cachets, suppositories, and dispersible granules. A solid carrier can be one or more substances that may also act as diluents, flavoring agents, solubilizers, lubricants, suspending agents, binders, preservatives, tablet disintegrating agents, or encapsulating materials.

In powders, the carrier is a finely divided solid, which is in a mixture with the finely divided active component. In tablets, the active component is mixed with the carrier having the necessary binding capacity in suitable proportions and compacted in the shape and size desired.

In certain embodiments, powders and tablets administered according to methods of the present disclosure preferably may contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without additional carriers, is surrounded by a carrier, which is thus in association with it. Similarly, cachets and lozenges are included. Tablets, powders, capsules, pills, cachets, and lozenges are included. Tablets, powders, capsules, pills, cachets, and lozenges can be used as solid forms suitable for oral administration.

Liquid preparations include, but are not limited to, solutions, suspensions, and emulsions, for example, water or water-propylene glycol solutions. For example, parenteral injection liquid preparations can be formulated as solutions in aqueous polyethylene glycol solution. In certain embodiments, chemical compounds administered according to methods of the present disclosure may thus be formulated for parenteral administration (e.g., by injection, for example, bolus injection or continuous infusion) and may be presented in unit dose for administration in ampoules, pre-filled syringes, small-volume infusion, or in multi-dose containers with an added preservative. The compositions may take such forms as suspensions, solutions, or emulsions in oily or aqueous vehicles, and may contain formulation agents such as suspending, stabilizing, and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

Aqueous solutions suitable for oral use can be prepared by dissolving the active component in water and adding suitable colorants, flavors, stabilizing and thickening agents, as desired. Aqueous suspensions suitable for oral use can be made by dispersing the finely divided active component in water with viscous material, such as natural or synthetic gums, resins, methylcellulose, sodium carboxymethylcellulose, or other well-known suspending agents.

Compositions suitable for topical administration in the mouth include, but are not limited to: lozenges comprising the active agent in a flavored base, usually sucrose and acacia or tragacanth; pastilles comprising the active ingredient in an inert base such as gelatin and glycerine or sucrose and acacia; and mouthwashes comprising the active ingredient in suitable liquid carrier.

Solutions or suspensions are applied directly to the nasal cavity by conventional means, for example, with a dropper, pipette, or spray. The compositions may be provided in single or multi-dose form. In compositions intended for administration to the respiratory tract, including intranasal compositions, the compound will generally have a small particle size, for example, of the order of 5 microns or less. Such a particle size may be obtained by means known in the art, for example, by micronization.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself; or it can be the appropriate number of any of these in packaged form.

Tablets, capsules, and lozenges for oral administration and liquids for oral use are preferred compositions. Solutions or suspensions for application to the nasal cavity or to the respiratory tract are preferred compositions. Transdermal patches for topical administration to the epidermis are preferred.

Further details on techniques for formulation and administration may be found in the latest edition of REMINGTON'S PHARMACEUTICAL SCIENCES (Mack Publishing Co., Easton, PA).

Routes of Administration

The compounds may be administered by any route, including, but not limited to, oral, sublingual, buccal, ocular, pulmonary, rectal, and parenteral administration, or as an oral or nasal spray (e.g., inhalation of nebulized vapors, droplets, or solid particles). Parenteral administration includes, for example, intravenous, intramuscular, intraarterial, intraperitoneal, intranasal, intravaginal, intravesical (e.g., to the bladder), intradermal, transdermal, topical, or subcutaneous administration. Also contemplated within the scope of the invention is the instillation of a pharmaceutical composition in the body of the patient in a controlled formulation, with systemic or local release of the drug to occur at a later time. For example, the drug may be localized in a depot for controlled release to the circulation, or for release to a local site.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection, or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in the form of shaped articles, e.g., films or microcapsules.

The methods described above may be further understood in connection with the following Examples. In addition, the following non-limiting examples are provided to illustrate the invention. However, the person skilled in the art will appreciate that it may be necessary to vary the procedures for any given embodiment of the invention, e.g., vary the order or steps.

Example 1

Abstract

Background: Recent evidence suggests that probiotic supplementation may improve short-term recovery following an acute bout of resistance exercise, which may augment adaptations. Thus, the purpose of this investigation was to determine the effects of probiotic supplementation during offseason training in collegiate athletes.

Methods: Twenty-three NCAA Division I female athletes (19.6±1.0 y, 67.5±7.4 kg, 170.6±6.8 cm) from their university volleyball (n=10) and soccer (n=13) teams participated in this study and were randomized into either a probiotic (DE111; n=11) or placebo ("PL"; n=12) group. Athletes completed the same 10-week resistance training program during the offseason, which consisted of 3-4 workouts per week of upper- and lower-body exercises and sport-specific training. Athletes consumed DE111 (DE111®; 5 billion CFU per day) or PL supplement in conjunction with a recovery drink (45 g CHO, 20 g PRO, 2 g FAT) immediately following resistance and sport-specific training for the entire 10-week program. On weekend or non-training days, athletes consumed the supplement with a meal. Pre- and post-training, all athletes underwent one-repetition maximum ("1RM") strength testing (squat, deadlift, bench press), performance testing (vertical jump, pro-agility) and isometric mid-thigh pull testing ("IMTP"). Three compartment body composition estimation ("BF %") was completed via BOD POD and BIA analysis, as well as muscle thickness ("MT") measurement of the rectus femoris ("RF") and vastus lateralis ("VL") via ultrasonography. Separate repeated measures analyses of variance were used to analyze all data.

DE111 produced significantly greater (p=0.015) improvements in BF % (−2.05±1.38%) compared to PL (−0.2±1.6%), with no other group x time interactions observed. Significant improvements were observed for both groups in squat 1RM (p<0.001), deadlift 1RM (p<0.001), bench press 1RM (p<0.001), vertical jump (p<0.001), BF % (p=0.001), and RF MT (p=0.015). No significant main effects were observed for any other variable.

Conclusions: These data suggest that probiotic consumption in conjunction with adequate post-workout nutrition may improve body composition in female Division I soccer and volleyball players following offseason training. Future research is needed to elucidate potential mechanisms responsible for these findings.

Methods

Twenty-three Division I female athletes (19.6±1.0 y, 67.5±7.4 kg, 170.6±6.8 cm) from the university volleyball (n=10) and soccer (n=13) teams participated in this double-blind, placebo-controlled, randomized design study. Following an explanation of all procedures, risks, and benefits, each participant provided her informed consent prior to participation in this study. The research protocol was approved by the Institutional Review Board of the University prior to participant enrollment. Exclusion criteria included the use of medication or other probiotic supplementation, ergogenic aids, or suffering from any medical, muscular, or metabolic contraindications.

Study Protocol

Participants reported to the Human Performance Lab ("HPL") on two separate occasions at the beginning and end of the 10-week training intervention on a 10-hour overnight fast. During these visits the participants were tested for body composition, muscle architecture, and isometric power. Athletes reported to their strength and conditioning coordinator on two separate occasions pre- and post-training, to measure 1RM for bench, squat, and deadlift along with testing vertical jump and pro-agility.

Body Composition

Three-Compartment Model (3C-W)

The criterion percent body fat (% BF) was estimated using the three compartment-water (3C-W) model described by Siri. See, e.g., W. E. Siri, *The gross composition of the body*, 4 ADVANCES IN BIOLOGICAL & MEDICAL PHYSICS 239 (1956), incorporated by reference herein in its entirety. The equation includes measurements of body density from the BOD POD), TBW (from the BIA), and body mass (BM). The equation for % BF is listed below:

% BF=[(2.118/Body density)−(0.78×TBW (L)/BM (kg))−1.354]×100

Air Displacement Plethysmography

Body density was estimated using air displacement plethysmography using the BOD POD® (COSMED, Rome, Italy). Prior to each test, the BOD POD was calibrated according to the manufacturer's instructions using a two-point calibration. It was first calibrated with the chamber empty, and then with a cylinder of known volume (50.097 L). Prior to testing, athletes were instructed to wear tight-fitting compression shorts, sports bras, and swimming caps, as well as to remove all metal, including jewelry and watches. Body mass was measured to the nearest 0.01 kg using the system's calibrated scale. All athletes were instructed to sit in the chamber, breathe normally, and to minimize any movement. A minimum of two trials was performed. If measurements were not within 150 mL of each other, a third trial was conducted. Thoracic gas volume was estimated using the BOD POD software, which uses standard prediction equations and demonstrated no difference compared to measured lung volumes. See, e.g., Megan A. McCrory, et al., *Body composition by air-displacement plethysmography by using predicted and measured thoracic gas volumes*, 84 J. APPLIED PHYSIOLOGY 1475 (1998), incorporated by reference herein in its entirety. The BOD POD system utilizes the inverse relationship between pressure (P) and volume (V) (Boyle's law: $P_1V_1=P_2V_2$) to determine body volume ($V_b$). Once $V_b$ is determined, the principles of densitometry are used to determine body composition from body density ($D_b$=mass/volume). See, e.g., A. R. Behnke, et al., *The specific gravity of healthy men*, 495 J. AM. MEDICAL ASS'N 495 (1942); J. F. Brozek, et al., *Densitometric analysis of body composition: revision of some quantitative assumptions*, 110 ANNALS OF THE NEW YORK ACADEMY OF SCI. 113 (1963); each of which is incorporated by reference herein in its entirety.

A chief advantage of the BOD POD is that it represents a densitometric method that is based on air displacement rather than on water immersion; therefore, it is simpler and more rapid than hydrostatic weighing ("HW") and potentially has wider clinical application. Measurement of $D_b$ by HW typically requires determination of residual lung volume ("$V_R$") to correct for air remaining in the lungs after maximal exhalation. See, e.g., A. Keys & J. Brozek, *Body fat in adult man*, 33 PHYSIOLOGICAL REVS. 245 (1953), incorporated by reference herein in its entirety. Any air remaining in the body (e.g., in the lungs or gastrointestinal tract) will have the effect of increasing buoyancy, leading to an overestimate of $V_b$, an underestimate of $D_b$, and thus an overestimate of the percentage of body fat (% BF). Although $V_R$ can be measured accurately by numerous techniques, such as $O_2$ dilution, $N_2$ washout, and He dilution, several investigators have examined whether $V_R$ can be predicted without com-promising the accuracy of body composition measurements by HW. See, e.g., R. M. Forsyth, et al., *Residual volume as a tool in body fat prediction*, 32 ANNALS OF NUTRITION & METABOLISM 62 (1988); A. C. Hackney & D. T. Deutsch, *Accuracy of residual volume prediction—effects on body composition estimation in pulmonary dysfunction*, 10 CANADIAN J. OF APPLIED SPORT SCIS. 88 (1985); R. W. Latin & R. O. Ruhling, *Total lung capacity, residual volume and predicted residual volume in a densitometric study of older men*, 20 BR. J. SPORTS MEDICINE 66 (1986); J. R. Morrow, Jr., et al., *Accuracy of measured and predicted residual lung volume on body density measurement*, 18 MEDICINE & SCIENCE IN SPORTS & EXERCISE 647 (1986); J. H. Wilmore, *The use of actual, predicted and constant residual volumes in the assessment of body composition by underwater weighing*, 1 MEDICINE & SCIENCE IN SPORTS & EXERCISE 87 (1969); each of which is incorporated by reference herein in its entirety. Whereas group means can sometimes be predicted with accuracy, $V_R$ is usually systematically over- or underestimated, and resulting errors have been observed of up to ~4.0% BF in normal, healthy subjects. In addition, individual errors in the calculation of % BF resulting from the use of predicted $V_R$ ($V_{R,pred}$) can be unacceptably high.

Similarly, measurement of $D_b$ by air displacement requires determination of the quantity of air in the lungs during normal tidal breathing, or the average thoracic gas volume ($V_{tg}$). $V_b$ determined by Boyle's law is underestimated by 40% of the $V_{tg}$ because the air in the lungs, because of its isothermal nature, is 40% compressible than the surrounding air (adiabatic conditions). See, e.g., P. Dempster & S. Aitkens, *A new air displacement method for the determination of human body composition*, 27 MEDICINE & SCIENCE IN SPORTS & EXERCISE 1692 (1995), incorporated by reference herein in its entirety. Failure to correct for this phenomenon will result in an overestimate of $D_b$ and, consequently, an underestimate of % BF. Thus an ancillary measurement of $V_{tg}$ by the BOD POD is incorporated into the testing procedure. See, e.g., LIFE MEASUREMENT INSTRUMENTS, *BOD POD Operator's Manual* (Life Measurement Instruments 1995), incorporated by reference herein in its entirety. Alternatively, the BOD POD also offers the use of a predicted $V_{tg}$ ($V_{tg,pred}$).

Bioelectrical Impedance Analysis ("BIA")

Total body water ("TBW") was demonstrated using multi-frequency bioelectrical impedance spectroscopy ("BIS") using the InBody® 570 Body Composition Analyzer device (Biospace, Inc., Seoul, Korea). Body composition from BIA is obtained from the measures of resistance and reactance when an electrical current travels throughout the body. Prior to each assessment the participants' hands and feet were thoroughly cleansed with InBody® provided tissues. The measurement electrodes are situated beneath the athlete's feet on the platform and on the palms and thumbs attached to handles on the device. Age, height, and gender are manually entered after weight is determined by a scale positioned within the device. The participant is then instructed from the software to stand fully erect, arms extended, while not touching the sides of the body, and to refrain from moving or talking until the assessment was completed. It has previously been shown that BIA is a valid measurement tool for determining TBW when compared to a deuterium oxide technique. See, e.g., Lindsey J. Anderson, et al., *Utility of multi-frequency bioelectrical impedance compared to deuterium dilution for assessment of total body water*, 72 NUTRITION & DIETETICS 183 (2015), incorporated by reference herein in its entirety.

Total body water ("TBW") alterations occur in a variety of altered physiological states. C. Basile, et al., *Total body water in health and disease: have anthropometric equations any meaning?*, 23 NEPHROLOGY DIALYSIS TRANSPLANTATION 1997 (2008); S. Bozzetto, et al., *Bioelectrical impedance vector analysis to evaluate relative hydration status*, 25 PEDIATRIC NEPHROLOGY 329 (2010); M. S. Demirci, et al., *Relations between malnutrition-inflammation-atherosclerosis and volume status. The usefulness of bioimpedance analysis in peritoneal dialysis patients*, 26 NEPHROLOGY DIALYSIS TRANSPLANTATION 1708 (2011); M. Y. Jaffrin & H. Morel, *Body fluid volumes measurements by impedance: a review of bioimpedance spectroscopy (BIS) and bioimpedance analysis (BIA) methods*, 30 MEDICAL ENG'G & PHYSICS 1257 (2008); J. Park, et al., *Relationship between extracellular water fraction of total body water estimated by bioimpedance spectroscopy and cardiac troponin Tin chronic haemodialysis patients*, 28 BLOOD PURIFICATION 61 (2009); K. Torimoto, et al., *The relationship between nocturnal polyuria and the distribution of body fluid: assessment by bioelectric impedance analysis*, 181 J. UROLOGY 219 (2009); H. Morel & M. Y. Jaffrin, *A bridge from bioimpedance spectroscopy to 50 kHz bioimpedance analysis: application to total body water measurements*, 29 PHYSIOLOGICAL MEASUREMENT 5465 (2008); each of which is incorporated by reference herein in its entirety.

Electrolyte disturbances from inflammation, injury, surgical procedures, and acute illness can result in TBW variations, and it has been recently suggested that TBW status may provide insight into the condition of body cells for evaluation of malnutrition. See, e.g., M. Y. Jaffrin, et al., 2008; A. Diouf, et al., *Validity of impedance-based predictions of total body water as measured by 2H dilution in African HIV/AIDS outpatients*, 101 BR. J. NUTRITION 1369 (2009); D. Gupta, et al., *Bioelectrical impedance phase angle as a prognostic indicator in breast cancer*, 8 BMC CANCER 249 (2008); D. Gupta, et al., *Bioelectrical impedance phase angle in clinical practice: implications for probnosis in stage IIIB and IV non-small cell lung cancer*, 9 BMC CANCER 37 (2009); A. Walter-Kroker, et al., *A practical guide to bioelectrical impedance analysis using the example of chronic obstructive pulmonary disease*, 10 NUTRITION J. 35 (2011); each of which is incorporated by reference herein in its entirety. D2O, the reference method for measuring TBW, requires the patient to ingest deuterated water and have saliva, urine, or venous blood samples collected pre-ingestion and a few hours later, typically at two or three hours, and again at four hours post-ingestion. See, e.g., H. Morel, 2008; D. Halliday & A. G. Miller, *Precise measurement of total body water using trace quantities of deuterium oxide*, 4 BIOMEDICAL & ENVIRONMENTAL MASS SPECTROMETRY 82 (1977); C. J. Rebouche, et al., *Evaluation of nuclear magnetic resonance spectroscopy for determination of deuterium abundance in body fluids: application to measurement of total-body water in human infants*, 45 AM. J. CLINICAL NUTRITION 373 (1987); D. A. Schoeller, et al., *Use of an automated chromium reduction system for hydrogen isotope ratio analysis of physiological fluids applied to doubly labeled water analysis*, 35 J. MASS SPECTROMETRY 1128 (2000); D. A. Schoeller, et al., *Total body water measurement in humans with 18O and 2H labeled water*, 33 AM. J. CLINICAL NUTRITION 2686 (1980); each of which is incorporated by reference herein in its entirety. This method is not easily utilized because it can be invasive and expensive, and cannot measure TBW variations over shorter time periods. See, e.g., M. Y. Jaffrin, et al., 2008; H. Morel & M. Y. Jaffrin, 2008. Water in body tissue is conducting; therefore, measurement of the body's resistance to electrical flow can indirectly quantify TBW. The prevalence of indirect methods for estimating TBW using bioelectrical impedance analysis (BIA) is increasing because BIA is simple, noninvasive, and reproducible, and BIA TBW estimates have shown to be strongly correlated with TBW estimates from D2O. See, e.g., C. Basile, et al., 2008; D. Gupta, et al., 2008; D. Gupta, et al., 2009; Y. Dou, et al., *Comparison of bioimpedance methods for estimating total body water and intracellular water changes during hemodialysis*, 26 NEPHROLOGY DIALYSIS TRANSPLANTATION 3319 (2011); each of which is incorporated by reference herein in its entirety.

BIA measures the resistance of body tissues by sending electrical current through the body. This method is based on the principle that lean body mass contains virtually all the water and conducting electrolytes in the body, providing a good electrical pathway, while fat-containing tissues provide poor electrical pathways. See, e.g., M. Y. Jaffrin, et al., 2008. Most BIA devices use resistance obtained from a single frequency ("SF"), alternating sinusoidal current in combination with other variables (e.g., weight, height, and gender), to create regression equations for TBW estimation. While SFBIA has the potential for segmental analysis, this method is generally used for whole body analysis and models the human body as a single cylinder with constant resistivity; however, errors in body composition estimates increase in persons out of normal body mass index (BMI) or percent fat ranges. See, e.g., M. Y. Jaffrin, et al., 2008; K. J. Shafer, et al., *Validity of segmental multiple frequency bioelectrical impedance analysis to estimate body composition of adults across a range of body mass indexes*, 25 NUTRITION 25 (2009); each of which is incorporated by reference herein in its entirety.

Multi-frequency (MF-BIA) analyses measure resistance at various frequencies from 1 kHz to 1 MHz and are frequently, but not solely, used to model the human body with five distinct cylinders (arms, trunk, and legs) with different resistivities to obtain whole body and segmental measures. See, e.g., H. Morel & M. Y. Jaffrin, 2008. Resistances are measured separately in these cylinders, providing segmental analyses. In addition, the low-frequency impedance measures provide assessment of extracellular water in addition to TBW. Validation of the Biospace InBody MF-BIA devices for predicting TBW is necessary as these devices have the potential to provide a feasible, cost-effective method to assess body water volume. These devise are largely intended for clinical settings where simplistic diagnostic tools that do not require laborious calculations are highly favorable.

Muscle Ultrasonography

Noninvasive measurements of muscle thickness ("MT") were collected using B-mode ultrasound imaging with a 12 MHz linear probe (General Electric LOGIQ P5, Wauwatosa, WI). Measurements were taken at 50% of the distance from the anterior, inferior suprailliac spin, to the most proximal point of the patella. See, e.g., Kelly M. M. e Lima, et al., *Reliability of the rectus femoris muscle cross-sectional area measurements by ultrasonography*, 32 CLINICAL PHYSIOLOGY & FUNCTIONAL IMAGING 221 (2012), incorporated by reference herein in its entirety.

Muscle architecture can be defined as the arrangement of muscle fibres relative to the axis of strength generation. See, e.g., Y. Kawakami, *The effects of strength training on muscle architecture in humans*, 3 INT'L J. OF SPORT & HEALTH SCI. 208 (2005); R. L. Lieber, *Skeletal Muscle, Structure, Function, and Plasticity*, in THE PHYSIOLOGICAL BASIS OF REHABILITATION 26 (3d ed., E. Lupash, ed., Lippincott Williams & Wilkins 2010); each of which is incorporated by reference herein in its entirety. The organization of these fibres occurs at the macroscopic level and is an important factor in determining the contractile properties of muscle. See, e.g., Y. Kawakami, et al., *Training-induced changes in muscle architecture and specific tension*, 72 EUR. J. OF APPLIED PHYSIOLOGY & OCCUPATIONAL PHYSIOLOGY 37 (1995); Y. Kawakami & T. Fukunaga, *New Insights into in vivo Human Skeletal Muscle Function*, 34 EXERCISE & SPORT SCIS. REVS. 16 (2006); each of which is incorporated by reference herein in its entirety. The anatomical measurements most often analyzed in muscle architecture and are directly related to these properties are: anatomical cross-sectional area, physiological cross-sectional area, fascicle length, muscle thickness, and pennation angles. See, e.g., Y. Kawakami, 2005; A. J. Blazevich, et al., *Anatomical predictors of maximum isometric and concentric knee extensor moment*, 105 EUR. J. OF APPLIED PHYSIOLOGY 869 (2009); R. L. Lieber, 2010; each of which is incorporated by reference herein in its entirety. Currently, these structural changes can be assessed by various imaging techniques such as computed tomography, magnetic resonance imaging, and ultrasound. See, e.g., M. G. Bembem, *Use of diagnostic ultrasound for assessing muscle size*, 16 J. STRENGTH & CONDITIONING RES. 103 (2002); M. Miyatani, et al., *Validity of ultrasonography muscle thickness measurements for estimating muscle volume of knee extensors in humans*, 86 EUR. J. APPLIED PHYSIOLOGY 203 (2002); C. I. Morse, et al., *Changes in triceps surae architecture with sarcopenia*, 183 ACTA PHYSIOLOGICAL SCANDINAVICA 291 (2005); J. M. Seymour, et al., *Ultrasound measurement of rectus femoris cross-sectional area and the relationship with quadriceps strength in COPD*, 64 THORAX 418 (2009); J. P. Ahtiainen, et al., *Panoramic ultrasonography is a method to measure changes in skeletal muscle cross-sectional area*, 108 EUR. J. APPLIED PHYSIOLOGY 273 (2010); each of which is incorporated by reference herein in its entirety.

Specifically for anatomical cross-sectional area, computed tomography and magnetic resonance imaging are considered the "gold standards" of measurement, but have some disadvantages. See, e.g., M. G. Bembem, 2002; N. D. Reeves, et al., *Ultrasonographic assessment of human skeletal muscle size*, 91 EUR. J. APPLIED PHYSIOLOGY 116 (2004); J. P. Ahtiainen, et al., 2010; each of which is incorporated by reference herein in its entirety. Ultrasound has gained importance as a reliable and inexpensive instrument of measurement to obtain images of muscle tissue, bone, and adipose tissues. See, e.g., M. G. Bembem, 2002; M. Miyatani, et al., 2002; M. Noorkoiv, et al., *Assessment of quadriceps muscle cross-sectional area by ultrasound extended-field-of-view imaging*, 109 EUR. J. APPLIED PHYSIOLOGY 631 (2010); each of which is incorporated by reference herein in its entirety. The ultrasound B-mode stands out by allowing the two-dimensional analysis necessary to identify the anatomical cross-sectional area and having a high correlation with other imaging techniques like magnetic resonance imaging or computed tomography. J. I. Esformes, et al., *Measurement of human muscle using ultrasonography*, 87 EUR. J. APPLIED PHYSIOLOGY 90 (2002); N. D. Reeves, et al., 2004; J. P. Ahtiainen, et al., 2010; M. Noorkoiv, et al., 2010; each of which is incorporated by reference herein in its entirety.

It is observed that anatomical cross-sectional area is often analyzed in studies with strength training, showing a strong relationship with the maximum capacity of muscle force production. See, e.g., M. G. Bembem, 2002; K. Kubo, et al., *Muscle Architectural Characteristics in Woman Aged 20-79 Years*, 35 MEDICINE & SCI. IN SPORTS & EXERCISE 39 (2003); K. Masuda, et al., *The relationship between muscle cross-* sectional area and strength in various isokinetic movements among soccer players, 21 J. SPORTS SCI. 851 (2003); each of which is incorporated by reference herein in its entirety. The functional importance of changes in the anatomical cross-sectional area of a muscle can be seen in its contribution to total force production. See, e.g., C. I. Morse, et al., 2005. Thus, one can justify the importance of reliable measurement of anatomical cross-sectional area from skeletal muscle. Anatomical cross-sectional area is the second best predictor for torque at different speeds analyzed in isokinetic equipment. See, e.g., A. J. Blazevich, et al., 2009. Because of the relative ease of measurement of anatomical cross-sectional area compared with physiological cross-sectional area and other parameters such as muscle volume, it is the best method for estimating muscle mass.

Two different protocols are commonly used to access muscle architecture parameters using ultrasound. In one protocol, anatomical cross-sectional area and muscle thickness of the rectus femoris is measured at 15 centimeters above the superior border of the patella. See, e.g., M. G. Bembem, 2002. Analysis of other parameters of the quadriceps muscles considers the level of 50% of the length of the thigh—the distance between the greater trochanter of the femur and the articular cleft between the femur and tibia condyles—for measurement by ultrasound. See, e.g., M. Miyatani, et al., 2002; K. Kubo, et al., 2003; J. Kubo, et al., *Differences in fat-free mass and muscle thicknesses at various sites according to performance level among judo athletes,* 20 J. STRENGTH & CONDITIONING RES. 654 (2006); A. J. Blazevich, et al., 2009; each of which is incorporated by reference herein in its entirety.

The reliability of measurements of images by ultrasound involves, beyond the resolution of the instrument, the researcher's experience and accuracy in identifying anatomical sites. See, e.g., A. J. Blazevich, et al., 2006. Individual variables, such as the sufficient relaxation of the muscle to be analyzed, the time elapsed since the last session of physical activity, and the characteristics of the muscles, influence the accuracy of measurements. See, e.g., W. Hopkins, *Measures of Reliability in Sports Medicine and Science,* 30 SPORTS MEDICINE 1 (2000), incorporated by reference herein in its entirety. There are studies involving the reliability of the ultrasound in areas such as the thickness of the artery intima-media carótida, abdominal fat thickness, brachial artery diameter, patellar tendon stiffness, and measures of muscle architecture, for example muscle thickness, fascicle length, and pennation angles. See, e.g., D. Baldassarre, et al. *Reproducibility Validation Study Comparing Analog and Digital Imaging Technologies for the Measurement of Intima-Media Thckness,* 31 STROKE 1104 (2000); A. Bazzocchi, et al., *Accuracy, reproducibility and repeatability of ultrasonography in the assessment of abdominal Adiposity,* 18 ACADEMIC RADIOLOGY 1133 (2011); C. M. Meirelles, et al., *Confiabilidade da Medida da Dilatação Fluxo-Mediada da Artéria Braquial pela Ultra-Sonografia,* 89 ARQUIVOS BRASILEIROS DE CARDIOLOGIA 176 (2007); H. Liu & P. S. Weinheld, *Reliability of a Two-Scan Ultrasonography Method for Evaluating Patellar Tendon Stiffness,* 6 BULLET. APPL. MECH. 41 (2010); M. Miyatani, et al., 2002; T. D. Leeds, et al., *B-mode, real-time ultrasound for estimating carcass measures in live sheep: accuracy of ultrasound measures and their relationships with carcass yield and value,* 86 J. ANIMAL SCI. 3203 (2008); C. I. Morse, et al., 2005; S. Abellaneda, et al., *The relative lengthening of the myotendinous structures in the medial gastrocnemius during passive stretching differs among individuals,* 106 J. APPLIED PHYSIOLOGY 169 (2009); K. Legerlotz, et al., *Variation and reliability of ultrasonographic quantification of the architecture of the medial gastrocnemius muscle in young children,* 30 CLINICAL PHYSIOLOGY & FUNCTIONAL IMAGING 198 (2010); C. E. Baldwin, et al., *Diaphragm and peripheral muscle thickness on ultrasound: Intra-rater reliability and variability of a methodology using non-standard recumbent positions,* 16 RESPIROLOGY 1136 (2011); each of which is incorporated by reference herein in its entirety.

Vastus lateralis measurements were taken in the same fashion as previously stated; however, the sampling location is determined by 50% of the straight-line distance between the greater trochanter and the lateral epicondyle of the femur. See, e.g., T. Abe, et al., *Relationship between sprint performance and muscle fascicle length in female sprinters,* 20 J. PHYSIOLOGICAL ANTHROPOLOGY & APPLIED HUMAN SCI. 141 (2001), incorporated by reference herein in its entirety. Prior to image collection, participants laid supine for 5 minutes, and the probe was coated with a water-based conduction gel. See, e.g., E. Arroyo, et al., *Effects of supine rest duration on ultrasound measures of the vastus lateralis,* 38 CLINICAL PHYSIOLOGY & FUNCTIONAL IMAGING 155 (2018), incorporated by reference herein in its entirety. For measurements of MT, the probe was oriented longitudinally in the sagittal plane parallel to the muscle tissue without depressing the skin. Once images were collected, analysis was completed using Image J software (version 1.45s; National Institutes of Health, Bethesda, MD, USA). MT was determined from the still image as the distance between the inferior border of the superficial aponeurosis and the superior border of the deep aponeurosis. Intraclass correlation coefficients ("$ICC_{3,k}$") and standard error of measurements ("SEM") for the ultrasound technician were calculated for the RF MT ($ICC_{3,k}=$ 0.99, $SEM_{3,k}=0.02$, MD=0.07 cm) and VL MT ($ICC_{3,k}=$ 0.99, $SEM_{3,k}=0.05$, MD=0.14 cm) from analysis of 10 individuals separated by 24 hours.

Strength Testing

Maximal strength testing was performed on the bench press, squat, and dead lift exercises. All 1RM testing was performed using methods previously described. See, e.g., J. Hoffman, *Norms for fitness, performance, and health* (Human Kinetics 2006), incorporated by reference herein in its entirety. Prior to testing, each athlete completed a general warm-up led by the strength and conditioning coach, which included jogging and a dynamic warm-up. Each athlete performed two warm-up sets using a resistance of approximately 40-60% and 60-80% of her perceived maximum, respectively. For each exercise, 3-4 subsequent trials were performed to determine the 1-RM. A 3-5 minute rest period was provided between each trial. Trials not meeting the range of motion criteria, or where proper technique was compromised, were discarded.

Power Testing (Isometric Mid-Thigh Pull)

The isometric mid-thigh pull ("IMTP") is a time-efficient laboratory-based test designed to reliability and accurately assess peak force ("PF") production and rate of force development ("RFD") across various time domains. See, e.g., Jeremy R. Townsend, et al., *Isometric Mid-Thigh Pull Performance is Associated with Athletic Performance and Sprinting Kinetics in Division I Men and Women's Basketball Players,* 31 J. STRENGTH & CONDITIONING RES. (2017); Ran Wang, et al., *Isometric Mid-Thigh Pull Correlates With Strength, Sprint, and Agility Performance in Collegiate Rugby Union Players,* 30 J. STRENGTH & CONDITIONING RES. 3051 (2016); T. Dos'Santos, et al., *Effect of Different Onset Thresholds on Isometric Mid-Thigh Pull Force-Time Variables,* J. STRENGTH & CONDITIONING RES. (2017); each of which is incorporated by reference herein in its entirety. Values obtained from the IMTP test have been shown to correlate well to athletic abilities such as speed, agility, weightlifting, and vertical jump, along with sport-specific performance. See, e.g., G. Beckham, et al., *Relationships of isometric mid-thigh pull variables to weightlifting performance*, 53 J. SPORTS MEDICINE & PHYSICAL FITNESS 573 (2013); B. K. Leary, et al., *The relationship between isometric force-time curve characteristics and club head speed in recreational golfers*, 26 J. STRENGTH & CONDITIONING RES. 2685 (2012); G. T. Mangine, et al., *Resistance training intensity and volume affect changes in rate of force development in resistance-trained men*, 116 EUR. J. APPLIED PHYSIOLOGY 2367 (2016); M. H. Stone, et al., *Maximum strength-power-performance relationships in collegiate throwers*, 17 J. STRENGTH & CONDITIONING RES. 739 (2003); each of which is incorporated by reference herein in its entirety.

The mid-thigh position was determined for each participant before testing by marking the midpoint distance between the knee and hip joints. Each participant was instructed to assume their preferred deadlift position by self-selecting the hip and knee angles. The height of the barbell was then adjusted up or down to make sure it is in contact with the mid-thigh. An overhand grip with lifting straps was used to ensure grip strength did not limit capacity to pull maximally. The participants were instructed to pull upwards on the barbell as hard and as fast as possible, and to continue their maximal efforts for 6 seconds. The force-time curve for each trial was recorded by a force plate (PASCO, Roseville, CA) with a sample rate of 1,000 Hz, similarly to previous studies. Peak force was defined as the highest force achieved during the 6-seconds isometric test minus the participant's body weight in Newtons. The RFD was then calculated with the following equation: RFD=$\Delta$Force/$\Delta$Time. The RFD equation was applied to the predetermined time band of 0-250 ms. See, e.g., Thomas Dos'Santos, et al., 2017; G. T. Mangine, et al., 2016. This was in accordance with previous studies, which used a similar predetermined time band when RFD demonstrated high reliability.

Performance Testing

A Vertical Jump testing station (Uesaka Sport, Colorado Springs, Colorado) was used to assess vertical jump height (±0.5 in.). Prior to the test, each athlete's standing vertical reach height was determined by colored squares located along the vertical neck of the device. These squares correspond with similarly colored markings on each horizontal tab, which indicate the vertical distance from the associated square. Vertical jump height was determined by the indicated distance on the highest tab reached following 3 maximal countermovement jump ("CMJ") attempts performed from a standing position with feet shoulder-width apart.

For the pro-agility test, three cones were placed parallel, five meters apart. The athletes set up for the test in a straddle position facing the middle cone. On their ready, the athletes were instructed to pivot and accelerate as quickly as possible to a cone 5 meters away and then upon reaching the first cone, pivot again and sprint the 10-meters distance to the furthest cone. Upon reaching this cone, the athletes once again pivoted to return to the middle cone as quickly as possible. During each change in direction, the athletes were asked to touch the ground next to the cone. Trials in which the athlete failed to touch the ground were discarded. Athletes were allowed three attempts, and the fastest time measured in seconds was recorded.

Supplementation Protocol

Participants were required to consume a placebo ("PL") or a probiotic ("DE111") once a day for 10 weeks. The probiotic supplement consisted of 5 billion CFU ($5 \cdot 10^9$ CFU) *Bacillus subtilis*, DE111 (DE111®, Deerland Enzymes, Kennesaw, Georgia, United States). On training days, supplementation occurred immediately post-workout with a protein and carbohydrate recovery drink (Gatorade Recover, Gatorade Co., Chicago, Illinois) consisting of 45 grams of carbohydrates, 20 grams of protein, and 2 grams of fat. This recovery drink was chosen to maximize postprandial muscle protein synthesis and to remain within NCAA macronutrient guidelines for nutritional support. See, e.g., D. R. Moore, et al., *Ingested protein dose response of muscle and albumin protein synthesis after resistance exercise in young men*, 29 AM. J. CLINICAL NUTRITION 161 (2009), incorporated by reference herein in its entirety. On weekend or non-training days, athletes were required to consume their supplement with a normal meal.

Dietary Logs

During the training and supplement intervention, participants were asked to complete a 3-day food log (two weekdays, one weekend day) for two separate weeks. Dietary recalls were used to provide an estimate of total kilocalorie intake ("kcal") and macronutrient distributions (carbohydrate, protein, and fat) of the athlete's typical weekly diet. All dietary analysis was completed using the MyFitnessPal application (Under Armour, Inc., Baltimore, Maryland), which contains a large, detailed U.S.-branded food database.

Training Protocol

Athletes participated in a linear periodized resistance training program 3 days per week throughout the entire 10-week training period (see Table 1). The program incorporated upper and lower workouts centered on three core lifts (bench press, squats, and dead lifts), commonly referred to as the "Wendler 5/3/1." This program organizes progressions over 4-week segments (i.e., 1 week of 3 sets of 5 repetitions on each core exercise, followed by 1 week of 3 sets of 3 repetitions, then 1 week of 1×5/3/1 repetitions). This is followed by a lighter "unloading" week of 3 sets of 5 repetitions. Accessory lifts followed a higher-volume pattern (i.e., 3-4 sets, 8-12 repetitions). In addition to strength training, three days per week the athletes participated in team conditioning, agility, jumping, and sprint work. These workouts consisted of approximately 30-40 minutes of sport-specific skill development and conditioning related work. All training was performed under the supervision of a certified strength and conditioning specialist ("CSCS").

TABLE 1

| Day 1 | Set × Reps | Day 2 | Set × Reps | Day 3 | Sets × Reps |
|---|---|---|---|---|---|
| Phase 1 (Weeks 1-2) | | | | | |
| Bench Press | 4 × 3-5 | Hang Clean | 4 × 3-5 | Power Clean High Pull | 4 × 3-5 |
| Band Pull Apart Extension | 60 reps | Squat | 4 × 3-5 | Terminal Knee | 4 × 12 |

TABLE 1-continued

| Day 1 | Set × Reps | Day 2 | Set × Reps | Day 3 | Sets × Reps |
|---|---|---|---|---|---|
| Eccentric Pull-ups | 2 × 8 | Box Jump | 5 × 3 | Deadlifts | 4 × 3-8 |
| 1 Arm DB Shoulder Press | 4 × 8 | Glute Ham Raise | 3 × :45 | Incline DB Bench | 4 × 6 |
| Inverted Row | 3 × :30 | Isometric Goblet Squat | 3 × :45 | Hanging Knee to Chest | 3 × 8 |
| DB Shrugs | 3 × :30 | Barbell Glute Bridge | 3 × :45 | Keiser 1-Arm Rot. Press | 3 × 8 |
| Front Raise | 3 × :30 | Good Mornings | 3 × :45 | TGU | 3 × 8 |
| Incline DB row | 3 × :30 | | | DB Row | 3 × 8 |
| | | Phase II (Weeks 3-6) | | | |
| Bench Press | 4 × 3-5 | Hang Clean | 4 × 3-5 | Power Clean | 4 × 3-5 |
| Band Pull Apart | 3 × 20 | Squat | 4 × 3-5 | Ankle Touches | 3 × 3 |
| Band Assist Pull-ups | 3 × 8 | Hip Flexor Stretch | :15 | Deadlifts | 4 × 3-5 |
| Dumbbell Shoulder Press | 3 × 10 | Box Jump | 3 × 3 | Incline DB Bench | 3 × 8 |
| TRX Row | 3 × 10 | Swiss Ball Leg Curl | 3 × 10 | Swiss Ball Pike | 3 × 10 |
| Ext. Rotation | 3 × 10 | Single Leg Squat | 3 × 5 | 1 Arm Rot. Press | 3 × 10 |
| Lateral Raise | 3 × 10 | Vertimax Jumps | 3 × 3 | Kettle Bell Windmill | 3 × 10 |
| Keiser Pulldown | 3 × 10 | Crossover Step-ups | 3 × 8 | Landmine Row | 3 × 10 |
| Push up | 3 × 10 | | | | |
| | | Phase III (Weeks 7-10) | | | |
| Bench Press | 4 × 3-5 | Hang Clean | 4 × 3-5 | Jump Power Shrugs | 4 × 3-5 |
| Band Pull Apart Extension | 4 × 20 | Squat | 4 × 3-5 | Terminal Knee | 3 × 12 |
| Band Assisted Pull-ups | 4 × 6 | Hip Flexor Stretch | :15 | Deadlifts | 4 × 3-5 |
| DB Push Press | 3 × 6 | Box Jump | 4 × 3 | Lateral band walk | 3 × 5 |
| Keiser 1-Arm Row | 3 × 10 | Swiss Ball Leg Curl | 3 × 10 | Band Press | 3 × 5 |
| DB Shrugs | 3 × 10 | Single Leg Squat | 3 × 5 | Kettlebell Halo | 3 × 5 |
| Face Pulls | 3 × 10 | Vertimax Jumps | 3 × 3 | Unsupported Row | 3 × 5 |
| TRX Push-up | 3 × 10 | Step Up | 3 × 8 | | |

Statistical Analysis

Statistical evaluation of performance, anthropometric, and subjective data was be accomplished using a repeated measures analysis of variance ("ANOVA"). Prior to the ANOVA, all data were assed for normal distribution, homogeneity of variance, and sample independence. In the event of a significant F-ratio, LSD post-hoc tests were used for pairwise comparisons. In addition, the partial eta squared statistic was calculated for effect size for all dependent variables, and according to Green et al., 0.01, 0.06, and 0.14 were interpreted as small, medium, and large effect sizes, respectively. See, e.g., S. Green et al., *Methods for controlling type I error across multiple hypothesis tests*, 2 USING SPSS FOR WINDOWS: ANALYSING AND UNDERSTANDING DATA 395 (2000), incorporated by reference herein in its entirety. An alpha level was set at $p \leq 0.05$, and all analyses were performed using SPSS version 24.0 (SPSS, Inc., Chicago, Illinois).

Results

There were no significant differences ($p>0.05$) in baseline values for any variable (see Table 2). No significant differences in average daily caloric intake were observed between DE111 (1836.4 kcal) and PL (1804.1 kcal). In addition, no significant differences were seen in carbohydrate (238.4 g vs. 215.1 g), protein (91.0 g vs. 94.5 g), and fat (60.5 g vs. 63.1 g) intakes between DE111 and PL, respectively. Furthermore, both DE111 and PL supplements were well tolerated, and no adverse side effects were reported.

TABLE 2

| Variable | Group | Pre | Post | Time | Time × Group |
|---|---|---|---|---|---|
| Squat 1RM (kg) | DE111 | 7.3 ± 11.2 | 87.1 ± 12.6 | p < 0.000 | p = 0.394; |
| | PL | 74.1 ± 15.3 | 93.4 ± 19.0 | | $n^2 = 0.043$ |
| Deadlift 1 RM (kg) | DE111 | 85.0 ± 14.5 | 96.0 ± 11.2 | p < 0.000 | p = 0.343; |
| | PL | 75.0 ± 13.1 | 80.6 ± 16.4 | | $n^2 = 0.056$ |
| Bench Press 1 RM (kg) | DE111 | 45.3 ± 8.0 | 48.0 ± 8.5 | p < 0.000 | p = 0.633; |
| | PL | 39.5 ± 5.3 | 46.6 ± 6.3 | | $n^2 = 0.012$ |
| Vertical Jump (in) | DE111 | 20.0 ± 2.2 | 21.0 ± 2.5 | p < 0.000 | p = 0.405; |
| | PL | 19.5 ± 2.7 | 22.0 ± 3.3 | | $n^2 = 0.041$ |
| Pro-Agility (sec) | DE111 | 5.07 ± 0.23 | 5.11 ± 0.21 | p = 0.077 | p = 0.794; |
| | PL | 4.59 ± 0.17 | 4.55 ± 0.19 | | $n^2 = 0.004$ |
| IMTP PF (N) | DE111 | 1570.3 ± 303.7 | 1598.1 ± 282.6 | p = 0.150 | p = 0.351; |
| | PL | 1334.3 ± 208.7 | 1446.9 ± 221.5 | | $n^2 = 0.049$ |
| IMTP RFD 250 ms (N) | DE111 | 3450.5 ± 1833.0 | 3336.0 ± 1676.5 | p = 0.923 | p = 0.761; |
| | PL | 2740.9 ± 1340.5 | 2794.3 ± 1311.9 | | $n^2 = 0.005$ |
| Body Fat (%) | DE111 | 25.06 ± 3.98 | 23.01 ± 2.94 | p < 0.000 | p = 0.015; |
| | PL | 21.0 ± 5.36 | 20.0 ± 5.25 | | $n^2 = 0.289$ |
| Rectus Femoris Thickness (cm) | DE111 | 2.22 ± 0.29 | 2.29 ± 0.27 | p = 0.015 | p = 0.500; |
| | PL | 1.80 ± 0.31 | 1.91 ± 0.28 | | $n^2 = 0.024$ |

TABLE 2-continued

| Variable | Group | Pre | Post | Time | Time × Group |
|---|---|---|---|---|---|
| Vastus Lateralis Thickness (cm) | DE111 | 1.75 ± 0.31 | 1.71 ± 0.22 | p = 0.623 | p = 0.308; $n^2$ = 0.151 |
| | PL | 1.31 ± 0.27 | 1.36 ± 0.23 | | |

Pre- to post-changes for all variables are presented in Table 2. Results showed that 10 weeks of offseason resistance training resulted in a significant main effect for time (p<0.001) for squat 1 RM (FIG. 1A), deadlift 1 RM (FIG. 1B), bench press 1RM (FIG. 1C), and vertical jump (FIG. 1D), with improvements in performance seen from pre- to post-testing. However, there was no main effect for time for pro-agility, IMTP PF, or IMTP RFD250 ms. Additionally, no significant group by time interactions were observed for any measure of strength or athletic performance.

Figure 2:
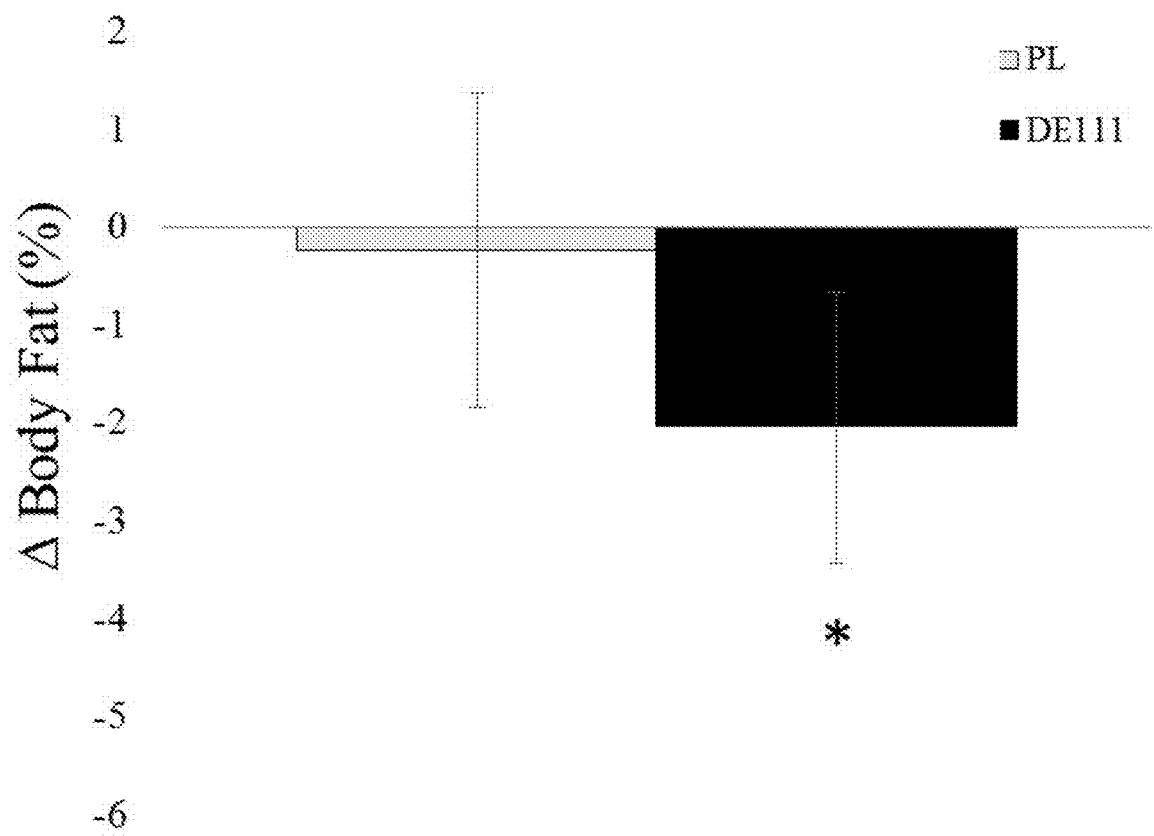
FIG. 2 depicts changes in body composition following 10 weeks of training ("*"=significantly greater change compared to placebo).

A significant main effect for time (p<0.05) was observed for BF % with both groups experiencing significant decreases in BF % from pre- to post-testing. A significant group by time interaction (p=0.015) was observed with DE111 experiencing a greater decrease in BF % compared to PL (FIG. 2). A significant main effect was observed for RF thickness (p=0.015) with both groups experiencing an increase in muscle thickness compared to pre-values. However, no main effect for time was observed for VL muscle thickness and no interactions were seen for RF or VL thickness between treatment groups.

Discussion

The major finding of this study was that probiotic supplementation resulted in superior improvements in body composition following 10 weeks of resistance training compared to a placebo. Furthermore, our data showed that 10 weeks of offseason training resulted in significant improvements in 1RM strength (bench press, squat, deadlift) and vertical jump height with probiotic supplementation providing no additional benefit compared to placebo. Additionally, we observed no difference between groups in pro-agility time, IMTP, peak force, IMTP RFD, muscle thickness. To the best of our knowledge, this is the first study to investigate the effects of probiotic supplementation on resistance training induced adaptations.

Following 10 weeks of training, both groups experienced improvements in body fat percentage with greater reduction in probiotic group (−2.1%) compared to placebo (−0.2%). Similar changes in body fat percentage (~−1.5%) following 8 weeks of offseason training and protein supplementation in female college basketball players has previously been reported. See, e.g., C. D. Wilborn, et al., *The Effects of Pre- and Post-Exercise Whey vs. Casein Protein Consumption on Body Composition and Performance Measures in Collegiate Female Athletes,* 12 J. SPORTS SCI. & MEDICINE 74 (2013), incorporated by reference herein in its entirety. Significant improvements in fat mass (−0.75 kg) in female collegiate basketball players following 8 weeks of resistance training has also been observed. See, e.g., L. W. Taylor, et al., *Eight weeks of pre- and postexercise whey protein supplementation increases lean body mass and improves performance in Division III collegiate female basketball players,* 41 APPLIED PHYSIOLOGY, NUTRITION, & METABOLISM 249 (2015), incorporated by reference herein in its entirety. Currently, there is a significant gap in the literature with regards to probiotics and body composition in healthy adults. However, a growing body of evidence suggests that in overweight and obese individuals, modulation of the gut microbiota produces favorable reductions in body mass. See, e.g., M. Sanchez, et al., *Effect of Lactobacillus rhamnosus CGMCC1.3724 supplementation on weight loss and maintenance in obese men and women,* 111 BR. J. NUTRITION 1507 (2014); J. M. Omar, et al., *Lactobacillus fermentum and Lactobacillus amylovorus as probiotics alter body adiposity and gut microflora in healthy persons,* 5 J. FUNCTIONAL FOODS 116 (2013); each of which is incorporated by reference herein in its entirety. Furthermore, it has been reported that probiotic supplementation attenuates increases in body fat mass during a prolonged high-fat diet in healthy, normal-weight adults. Furthermore, it was observed that just 3 days of hypercaloric diet (3400 kcal) altered participant gut microbiome resulting in an additional energy harvest of 150 kcal. Taken together, while the participants in our study on average did not report high average daily caloric or fat intake, it is possible that the probiotic supplement reduced energy storage following potential episodic over-feedings during the 10 weeks. Generally speaking, high-level performance is influenced by a variety of physiological factors, with excess body fat believed to hinder many performance parameters (e.g., speed, power, agility). As beneficial changes in body fat mass have reported to be modest over multiple training seasons in female athletes and negative alterations in body composition are often experienced in the offseason, the findings of the present study may prove useful to athletes seeking to improve body composition. See, e.g., P. R. Stanforth, et al., *Body composition changes among female NCAA division 1 athletes across the competitive season and over a multiyear time frame,* 28 J. STRENGTH & CONDITIONING RES. 300 (2014); M. M. Minett, et al., *Changes in body composition and bone of female collegiate soccer players through the competitive season and off-season,* 17 J. MUSCULOSKELETAL & NEURONAL INTERACTIONS 386 (2017); each of which is incorporated by reference herein in its entirety.

It is important to note that while the underlying mechanisms of probiotic-induced improvements in body composition were outside the scope of this investigation, evidence suggests that gut microbiota composition has wide-reaching effects on the human body. These microorganisms in turn modulate intestinal permeability, which may play a role in the absorption of protein post-workout after acute muscle breakdown. It has previously been reported that high-intensity interval training and resistance exercises increase markers of intestinal damage and may impair dietary protein digestion and absorption during post-exercise recovery. This impairment in absorption may lead to a reduced capacity for amino acid uptake and may blunt training adaptations. In the present study, increased protein absorption in the probiotic group may have contributed to the improvements in body composition by increased dietary protein-induced thermogenesis and altered satiety signaling. See, e.g., M. S. Westerterp-Plantenga, et al., *Satiety related to 24 h diet-induced thermogenesis during high protein/carbohydrate vs high fat diets measured in a respiration chamber,* 53 EUR. J. CLINICAL NUTRITION 495 (1999); M. Veldhorst, et al., *Protein-induced satiety: effects and mechanisms of different proteins,* 94 PHYSIOLOGY & BEHAVIOR 300 (2008); each of which is incorporated by reference herein in its entirety. On average, our athletes had a daily consumption of 1.6 g/kg of protein including the provided post-workout nutrition (20 g PRO). While the supplemental protein allowed these athletes to meet recommended range of protein intake for supporting lean muscle accretion (1.4-2.0 g/kg/d), intakes above this reference range have been suggested for additional improvements in body composition. See, e.g., R. Jäger, et al., *International Society of Sports Nutrition Position Stand: protein and exercise*, 14 J. INT'L SOC'Y SPORTS NUTRITION 20 (2017), incorporated by reference herein in its entirety. Thus, improved amino acid uptake in the probiotic group may have allowed for more efficient protein digestion, simulating the effects of a higher daily protein intake. Nevertheless, future work is needed to investigate potential underlying mechanisms for the observed improvements in body composition.

Following 10 weeks of resistance training, all participants experienced improvements in 1RM strength measurements, with no differences observed between experimental groups. These data are in agreement with previous investigations reporting similar strength adaptations following offseason resistance training. See, e.g., A. C. Fry, et al., *The Effects of an Off-season Strength and Conditioning Program*, 5 J. APPLIED SPORT SCI. RES. 174 (1991); W. J. Kraemer, et al., *Influence of resistance training volume and periodization on physiological and performance adaptations in collegiate women tennis players*, 28 AM. J. SPORTS MEDICINE 626 (2000); S. Nimphius, et al., *Changes in muscle architecture and performance during a competitive season in female softball players*, 26 J. STRENGTH CONDITIONING RES. 2655 (2012); each of which is incorporated by reference herein in its entirety. Additionally, no improvements in IMTP peak force or IMTP RFD were observed. For the IMTP, the bar is placed at a location simulating the body's position at the beginning of the second pull of the clean exercise. While our athletes were trained in the clean exercise and we accounted for a familiarization period, the IMTP was a new test for these athletes. Many studies have investigated the relationship between IMTP and athletic performance, but only one has reported improvements in IMTP performance following chronic resistance training. See, e.g., G. Beckham, et al., *Relationships of isometric mid-thigh pull variables to weightlifting performance*, 53 J. SPORTS MEDICINE & PHYSICAL FITNESS 573 (2013); C. Thomas, et al., *Relationship between isometric mid-thigh pull variables and sprint and change of direction performance in collegiate athletes*, 4 J. TRAINOLOGY 6 (2015); each of which is incorporated by reference herein in its entirety. Thus, it may be too early to implicate the IMTP as a sensitive indicator of performance improvements when used as a novel test. The athletes in our study did not experience improved pro-agility times in either group following offseason training. This is in contrast to a previous study reporting significant improvements in agility times following offseason training in female collegiate volleyball and basketball players. While our athlete participants were comprised from two separate athletic teams (i.e., volleyball and soccer) and completed matching resistance training program, sport-specific team training and agility sessions were not controlled in this study. As soccer and volleyball require unique skills for sport success, team-specific activities were not the same for all participants over the 10-week intervention. Thus, differences in sport-specific training explain why we did not observe a training effect for agility performance.

We hypothesized that the probiotic supplement would promote improved dietary protein absorption and utilization, resulting in enhanced muscular adaptations following training. Results of this study indicate there were no differences in muscle size increases between groups with a significant time effect for an increase in RF muscle thickness, with no significant increase seen in VL muscle thickness. These data are in agreement with a previous investigation reporting no change in VL thickness following 14 weeks of a periodized resistance training program in division I softball players. However, previous work has shown improvements in both RF and VL thickness following strength training programs of various lengths. See, e.g., A. J. Wells, et al., *Vastus Lateralis Exhibits Non Homogenous Adaptation to Resistance Training*, MUSCLE NERVE (2014); J. R. Hoffman, et al., *Efficacy of phosphatidic acid ingestion on lean body mass, muscle thickness and strength gains in resistance-trained men*, 9 J. INT'L SOC Y SPORTS NUTRITION 47 (2012); M. V. Franchi, et al., *Muscle thickness correlates to muscle cross sectional area in the assessment of strength training induced hypertrophy*, SCANDINAVIAN J. MEDICINE & SCI. IN SPORTS (2017); each of which is incorporated by reference herein in its entirety. The lack of growth in the VL was unexpected, as exercises chosen for the offseason training program have been reported to include substantial activation of both the RF and VL musculature. See, e.g., A. Caterisano, et al., *The effect of back squat depth on the EMG activity of 4 superficial hip and thigh muscles*, 16 J. STRENGTH & CONDITIONING RES. 428 (2002); W. P. Ebben, *Hamstring activation during lower body resistance training exercises*, 4 INT'L J. SPORTS PHYSIOLOGY & PERFORMANCE 84 (2009); each of which is incorporated by reference herein in its entirety. Interestingly, Wells and colleagues found no change in VL thickness measuring at the same site as our study (VL0), while increases in VL thickness were observed 5 cm medial (VL5) to the VL0 site. Thus, discrepancies in muscle thickness adaptations in the literature may be due to selected measurement sites.

Additional limitations consisted of the consistence of athletes being able to return to their lockers at the appropriate time each day to consume their probiotic or placebo. Also, athletes on occasion would miss workouts for school- or work-related reasons. While there were not any excessive absences from training by any athletes, there were athletes that could not work out with their respective team during each meeting because of their daily schedules. While we obtained dietary recalls, diet was not controlled, so the actual diet of each athlete cannot be known for certain.

CONCLUSION

In summary, we report for the first time that probiotic supplementation with a *Bacillus subtilis*-containing composition (DE111) may improve body composition in female collegiate athletes in conjunction with offseason resistance training. These data are of interest to a wide array of athletes attempting to optimize body composition changes in the offseason. Additionally, as acute and chronic resistance training induced stressors have the potential to negatively impact immune, neuroendocrine, and gut health, promoting an optimal microbiota could benefit athletes. Nevertheless, further research is needed to investigate the potential benefits of probiotics in relation to protein absorption, acute exercise recovery, body composition, and training induced muscular adaptation in athletes.

The use of the terms "a," "an," "the," and similar referents in the context of describing the present invention (especially in the context of the claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Use of the term "about" is intended to describe values either above or below the stated value in a range of approximately ±10%; in other embodiments, the values may range in value above or below the stated value in a range of approximately ±5%; in other embodiments, the values may range in value above or below the stated value in a range of approximately ±2%; in other embodiments, the values may range in value above or below the stated value in a range of approximately ±1%. The preceding ranges are intended to be made clear by context, and no further limitation is implied. All methods described herein can be performed in any suitable order unless otherwise indicated here in or otherwise clearly contradicted by context. The use of any and all examples, or exemplary language (e.g., "such as") provided herein, is intended merely to better illuminate the invention and does not pose a limitation on the scope of the invention unless otherwise stated. No language in the specification should be construed as indicating any non-claimed element as essential to the practice of the invention.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entireties. The present invention may be embodied in other specific forms without departing from the spirit or essential attributes thereof, and, accordingly, reference should be made to the appended claims, rather than to the foregoing specification, as indicating the scope of the invention.

We claim:

1. A method of improving body composition in a female human individual, comprising the step of:
    (a) administering orally to the female human individual a composition consisting essentially of an isolated strain of *Bacillus subtilis* subspecies inaquosorum having accession number NRRL B-67989 in a dose of from about $1 \times 10^8$ CFU per day to about $1 \times 10^{11}$ CFU per day for at least 70 days, wherein the body fat percentage of the female human individual is reduced when said individual is submitted to a resistance and/or conditioning training program for at least 70 days.

2. The method of claim 1, wherein the dose is from about $1 \times 10^9$ CFU per day to about $1 \times 10^{10}$ CFU per day.

3. The method of claim 1, wherein the dose is about $5 \times 10^9$ CFU per day.

4. The method of claim 1, wherein the administering step is performed for at least 90 days.

5. The method of claim 4, further comprising the step of:
    (b) submitting the female human individual to the resistance training program 3 days per week throughout the entire at least 90 days.

6. The method of claim 5, further comprising the step of:
    (c) submitting the female human individual to the conditioning training program 3 days per week throughout the entire at least 90 days.

7. The method of claim 1, further comprising the step of:
    (b) submitting the female human individual to the resistance training program 3 days per week throughout the entire at least 70 days.

8. The method of claim 7, further comprising the step of:
    (c) submitting the female human individual to the conditioning training program 3 days per week throughout the entire at least 70 days.

9. The method of claim 1, wherein the body fat percentage of the female human individual is reduced by at least 1%.

10. The method of claim 1, wherein the body fat percentage of the female human individual is reduced by at least 2%.

11. The method of claim 1, wherein said female human individual is an adult.

* * * * *